United States Patent [19]

Soldin

[11] Patent Number: 5,780,307
[45] Date of Patent: Jul. 14, 1998

[54] IMMUNOSUPPRESSIVE DRUG BINDING PROTEINS AND USE

[76] Inventor: Steven J. Soldin, 6335 31st St., NW., Washington, D.C. 20015

[21] Appl. No.: 686,759

[22] Filed: Jul. 26, 1996

Related U.S. Application Data

[63] Continuation of Ser. No. 200,404, Feb. 23, 1994, abandoned, and a division of Ser. No. 224,868, Apr. 8, 1994, which is a continuation of Ser. No. 200,404, which is a continuation-in-part of Ser. No. 782,761, Oct. 22, 1991, abandoned, and Ser. No. 841,792, Feb. 26, 1992, abandoned, which is a continuation-in-part of Ser. No. 521,074, May 9, 1990, abandoned, said Ser. No. 782,761, is a continuation-in-part of Ser. No. 487,115, Mar. 2, 1990, abandoned, which is a continuation-in-part of Ser. No. 279,176, Dec. 2, 1988, abandoned.

[51] Int. Cl.$^6$ ............................................. G01N 33/567
[52] U.S. Cl. .......................... 436/503; 436/518; 435/7.1; 530/328; 530/350; 530/827
[58] Field of Search .................. 435/7.1, 7.4, 7.8, 435/7.9, 7.92, 7.93, 7.95, 975; 530/328, 350, 827; 436/503, 518

[56] References Cited

U.S. PATENT DOCUMENTS

| | | | |
|---|---|---|---|
| 4,094,963 | 6/1978 | Safena . | |
| 4,668,640 | 5/1987 | Wang et al. | 436/536 |
| 4,722,999 | 2/1988 | Handschumacher et al. | 530/412 |
| 4,727,035 | 2/1988 | Mahoney | 435/518 |
| 5,047,512 | 9/1991 | Handschumacher et al. | 530/402 |
| 5,109,112 | 4/1992 | Siekierka et al. | 530/350 |
| 5,196,352 | 3/1993 | Siekierka et al. . | |

FOREIGN PATENT DOCUMENTS

| | | |
|---|---|---|
| 0 285 603 | 10/1988 | European Pat. Off. . |
| 8 602 080 | 4/1988 | WIPO . |

OTHER PUBLICATIONS

Ziegler et al., "Identification of Cyclosporin Binding Sites in Rat Liver Plasma Membranes, Isolated Hepatocytes, and Hepatoma Cells by Photoaffinity Labeling Using [3H]Cyclosporin–Diaziridine", Biochimica et Biophysica Acta, vol. 855, No. 1 (13 Feb. 1986), pp. 147–156. QD1B5.
Harding et al. *J. Biol. Chem.*, 261:8547 (1986).
Agarwal et al. *Transplantation*, 42:627 (1986).
Takahashi et al. *Nature*, 337:473 (1989).
Steiner et al. *FASEB J.*, 2:9025A, pp. 1850, (1988).
Merker et al. *J. Immunol.*, 132:3064 (1984).
Donnelly et al. *Ther. Drug Monitor*, 11:696 (1989).
Quesniaux et al. *Clin. Chem.*, 33:1, pp. 32–37, (1987).
Rosborough et al. *Transplant Proc.*, 23:2890 (1991).
Tai et al. *Biochem.*, 25:5269 (1986).
Fretz et al. *J. Am. Chem. Soc.*, 113:1409 (1991).
Koletsky et al. *J. Immunol.*, 137:3, pp. 1054–1059, (1986).
Siekierka et al. *Nature*, 341:755 (1989).
Harding et al. *Nature*, 341:758 (1989).
Palaszynski et al. *Clin. Biochem.*, 24:63 (1991).
Russell et al. *Ther. Drug Monitor*, 13:32 (1991).
Donnelly et al. *Clin. Biochem.*, 24:71 (1991).
Donnelly et al. *Transplant. Proc.*, 23:2886 (1991).

*Primary Examiner*—Jeffrey Stucker

[57] ABSTRACT

Purified immunosuppressive drug binding protein (immunophilin) of molecular weight 34–37 kDa and pI of about 6.5 is described. The 34–37 kDa immunophilin specifically binds FK-506, rapamycin and CsA with high affinity. This novel immunophilin can be used as a reagent for capturing, detecting and quantifying immunosuppressive drugs and their biologically active metabolites, derivatives and analogues in tissue or fluid samples, and for the capturing potential immunosuppressive drugs from microbial extracts or culture media.

18 Claims, 34 Drawing Sheets

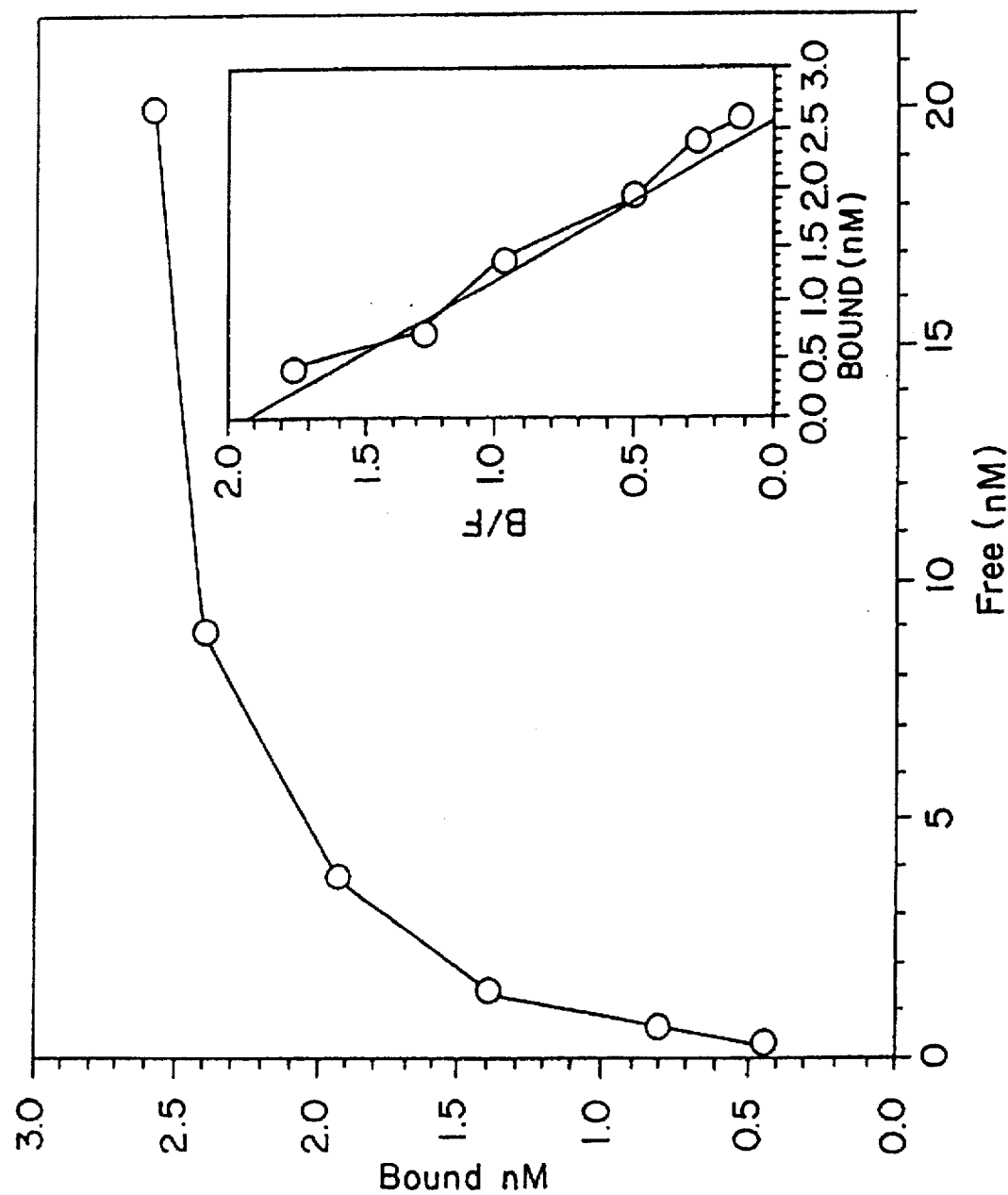

IMMUNOSUPPRESSIVE DRUG BINDING PROTEINS AND USE

This is a divisional of U.S. Ser. No. 08/224,868 filed Apr. 8, 1994, which is a continuation of U.S. Ser. No. 08/200,404, filed Feb. 23, 1994, now abandoned which is a continuation in part of U.S. Ser. No. 07/782,761, filed Oct. 22, 1991, now abandoned which is a continuation in part of U.S. Ser. No. 07/487,115, filed Mar. 2, 1990, now abandoned, which is a continuation in part of U.S. Ser. No. 07/279,176, filed Dec. 2, 1988, now abandoned. This is also a continuation of U.S. Ser. No. 08/200,404, filed Feb. 23, 1994, now abandoned which is a continuation in part of U.S. Ser. No. 07/841,792, filed Feb. 26, 1992, now abandoned which is a continuation in part of U.S. Ser. No. 05/521,074, filed May 9, 1990, abandoned.

BACKGROUND OF THE INVENTION

This invention relates to immunosuppressive drug binding proteins and their use in methods for the quantitation of and isolation from such drugs in biological fluids. More particularly, this invention relates to purified cytosolic, non-immunoglobulin binding proteins that specifically bind carbocyclic lactone-lactam macrolides, macrocyclic and cyclic peptide immunosuppressive drugs, and their uses.

DESCRIPTION OF THE BACKGROUND ART

Cyclosporine is a generic name for a group of neutral, highly hydrophobic cyclic undecapeptides of fungal origin (see sketch I for the structure of Cyclosporin A ("CsA"), an immunosuppressive drug currently in clinical use). CsA is in widespread use as an immunosuppressant for recipients of solid organ grafts, and is effective in preventing graft-vs.-host reaction after allogeneic bone marrow transplantation.

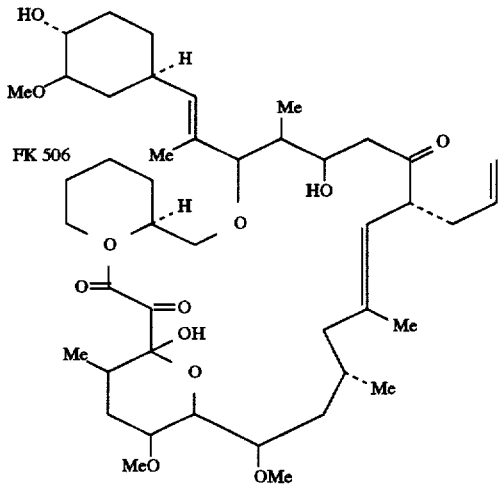

I

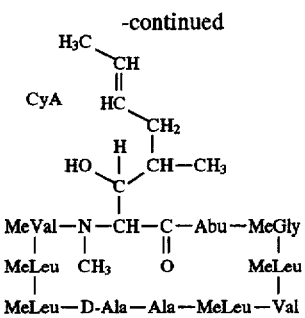

-continued

See, in general, Cohen et al., *Ann. Intern. Med.* 101:667 (1984). CsA is also being investigated as a possible treatment for autoimmune diseases such as Type 1 diabetes mellitus (Assan et al., *The Lancet*, 67 (Jan 12, 1985)), psoriasis (Ellis et al., *J. Amer. Med. Assoc.*, 256:3110 (1986) and vernal keratoconjunctivitis (Ben Ezra et al., *Transplant. Proc.*, 20:644 (1986)).

All of the metabolites characterized to date have retained the cyclic aspect of the molecule, and, as with the parent CsA, the metabolites are extensively bound to target tissues. Ryffel et al., *Transplant. Proc.*, 20:575 (1988).

The immunosuppressive cyclosporines and their metabolites are known to interfere with T-lymphocyte helper and effector cell proliferation, and CsA selectively inhibits lymphokine production by stimulated T cells. Nonetheless, the mechanism of action of cyclosporines remains unclear. See, generally, Drugge et al., *Transplant. Proc.*, 20:301 (1988), a review.

In view of the fact that all known regulatory biochemicals interact with a macromolecular receptor, typically a protein or glycoprotein, as an initial step in their mechanism of action, such receptors for cyclosporines have been sought. Although several candidate receptors have been identified, it is not yet settled which, if any, of these putative receptors are directly related to the mechanism(s) of action of cyclosporines. Candidate pharmacological receptors for CsA include: (1) cyclophilin, a 17,628 dal. protein isolated from the soluble cytoplasmic fraction of lymphocytes, hepatocytes, thyrocytes, and other cell types [Handschumacher et al., *Science*, 226:544 (1984); Harding et al., *J. Biol. Chem.*, 261:8547 (1986); Handschumacher et al., U.S. Pat. No. 4,722,999, issued Feb.2, 1988; Harding et al., Adv. *Inflamm. Res.*, 12:283 (1988)]; (2) calmodulin, a 16,680 dal. intracellular protein that mediates the effects of $Ca^{2+}$-requiring enzymes [see, in general, Hess et al., *Transplant Proc.*, 18:219 (1986)]; and (3) prolactin receptors on the surface T and B lymphocytes (Russell, et al., *Immunol.*, 134:3027 (1985)).

Cyclosporine undergoes extensive metabolism in the liver, primarily through demethylation, hydroxylation and intramolecular cyclization. Some 21 metabolites of CsA are presently known, with the metabolites being designated $M_1-M_{21}$; $M_1$, $M_{16}$ and $M_{17}$ are the primary metabolites of CsA. Cyclosporins A through Z are now known [Kobel et al., *Eur. J. Appl. Microbiol. Technol.*, 14:237 (1982)], as are a wide variety of synthetic analogues and derivatives [Rosenthaler et al., PCT application W086/02080, published Apr. 10, 1986].

At the dosages necessary to prevent organ rejection in patients, CsA and certain of its biologically active metabolites exhibit serious toxic side effects, such as nephrotoxicity, epigastric pain, transient paraesthesia, mild hypertrichosis, gum hyperplasia, and infections. Thus, the clinical use of cyclosporine for transplantation is complicated by the narrow therapeutic "window" between the inadequate immunosuppression that occurs at low doses and the toxic effects that result from over-administration. Ryffel et al., *Arch. Toxicol.*, 53:107 (1983), Myers et al., *N. Eng. J. Med.*, 311:699 (1984).

As a result of the aforementioned clinical problems with CsA, there is an ongoing search for substitute immunosuppressive drugs that are at least as efficacious as CsA but at dosages sufficiently low so as to avoid toxic side effects. One such drug is the macrolide antibiotic produced by fungi and referred to as tacrolimus or FK-506 (for the structure, see sketch I). Although of a chemical structure very different than that of CsA, FK-506 exhibits similar anti-lymphocytic activities and an immunosuppressive potency said to exceed that of CsA by 100-fold. Thomson, *Immunol. Today*, 10: 6 (1989); ibid. 11:35 (1990). FK-506 has performed well in clinical trials, particularly with liver transplant patients (see, in general, *Transplant. Proc.* 22: 5–113 (1990), although reports of toxic side effects at dosages required to prevent organ rejection have appeared (see, *Transplant. Proc.*, 1990, above). Thus, the therapeutic window for this drug is also narrow.

Like CsA, FK506 is also metabolized primarily by enzymes present in membranes of the endoplasmic reticulum of liver cells. Metabolites thus far identified include C13, C15 and C31 O-demethyl, C19 hydroxymethyl, C12 monohydroxylate, and C36 isomerized hydroxylate compounds. See, e.g., Lhoest et al, *Drug Metabolism and Disposition*, 31:850 (1993); Iwasaki et al, ibid., 971; Perotti et al, ibid. 55. The O-demethyl compounds are biologically active, although not as active as the parent drug.

Sirolimus (also known as rapamycin ("RAP")), a fungal macrolide with a structure similar to that of FK-506, is also an immunosuppressive drug, and its effects, at least in experimental animals, are similar to those of FK-506. Martel, *Can. J. Physiol. Pharmacol.* 55:48 (1977); Metcalf et al, *Transplant.* 49:798 (1990).

As the result of the need to balance the anti-rejection dosage requirements with the avoidance of toxic side effects, dosages and plasma concentrations of the drugs must be carefully monitored throughout the life of the organ recipient.

Currently, CsA, FK-506 and RAP and their metabolites are being assayed by high pressure liquid chromatography ("HPLC"), radioimmunoassay ("RIA") using $^3$H or 125I as tracers, and fluorescence polarization immunoassay ("FPIA").

Solid phase extraction of CsA and metabolites from patient samples, coupled with HPLC, have been used to separate and identify CsA and its metabolites. Christians et al., *Clin. Chem.*, 34:34 (1988); Lensmyer, et al., *Transplant. Proc.*, 20:614 (1988); Charles et al., *Therap. Drug Monitor,* 10:97 (1988). Not only are such methods time consuming for clinical laboratory personnel, expensive to perform, and generally too slow in producing data, but they are limited to separating and estimating the immunosuppressive drug and its metabolites, and are not capable of distinguishing between those that are biologically active from those that are inert. HPLC therefore, appears to be suitable only for measurements of unmetabolized drug. Felder, et al., *Clin. Chem.*, 32:1378 (1986).

Immunoassays for these drugs are known. The various immunoassay methods all involve the basic step of a competitive reaction between tracer labeled (e.g., $^3$H, $^{125}$I, or a fluorescent molecule) drug and the drug analyte for binding sites on an antibody specific to these compounds. As the result of the competitive reaction, antibody-bound labeled drug will be reduced in amount by the unlabeled analyte in the sample. See, generally, Mahoney, U.S. Pat. No. 4,727, 035, Feb. 23, 1988; Quesniaux et al., *Immunol. Lett.*, 9:99 (1985); Rosenthaler, PCT application W086/12080, published Apr. 10, 1986; Tamura et al, *Transplant. Proc.* 19:23 (1987); Cadoff et al, *Transplant. Proc.* 22: 50 (1990). Immunoassays using a polyclonal or monoclonal antibody measures the sum of the parent compound and only those of its metabolites that possess the requisite immuno-determinants (estimated as from 7 to 32% cross reactivity, Felder et al., supra), only some of which may be active as immunosuppressants or toxins. Furthermore, immunoassay values using $^{125}$I-CsA as the tracer give discrepant results compared to those assays using $^3$H-CsA, for reasons not yet understood. Felder, R. A., et al., supra.

Immunoassays for cyclosporines and metabolites using monoclonal antibodies are known. Quesniaux [Quesniaux et al., *Clin. Chem.*, 33:32 (1987)] developed two types of monoclonal antibodies (mAb)—one specific to CsA and another, a non-specific mAb that binds both to CsA and its metabolites. A comparison of immunoassays using polyclonal antibodies and the two mAb preparations, employing both radiolabels (RIA) and fluorescent labels (FPIA), with HPLC methods, concluded that polyclonal antibodies and non-specific mAb's (whether in an RIA or FPIA), estimate both CsA and a range of its metabolites, whereas the specific mAb and HPLC measure the CsA parent compound. Gibbons, et al., *Transplant Proc.* 20:339 (1988). Others have found that the RIA for CsA is extremely non-specific, and overestimates HPLC-determined levels of total Cs, as liver function deteriorates in liver transplantation patients. Blyden, *Clin. Pharm. Therap.*, 37:182 (1985); Holt et al., *Clin. Chem.*, 34:1091 (1988). Similarly, the immunoassays for FK506 developed by Tamura et al and Cadoff et al cannot distinguish between the parent drug and those of its metabolites that are immunologically, but not biologically, active. Furthermore, it is known that there is a lack of correlation between dosage and plasma correlation of FK506 determined by the aforementioned immunoassay. Cadoff et al, above. Similarly, the RIA for CsA is reported to be extremely non-specific, and overestimates HPLC-determined levels of total cyclosporine. Holt et al. supra.

Because of the uncertain biologic significance of the differences among drug and drug metabolite assays and between the cross reactivity spectra of the various tests, large correlation studies are now required in order to determine which method and matrix offers the best technique for therapeutic drug monitoring so that adverse chemical events after therapy may be predicted and avoided.

Thus, there persists an important need for a rapid, simple and inexpensive assay for FK-506 and rapamycin and their analogues, derivatives and metabolites that not only quantifies accurately and reproducibly the concentrations of these molecules in fluid samples, but also is capable of discriminating between those species that are pharmacologically active and those that are not.

Soldin, U.S. Ser. No. 07/279,176, filed Dec. 2, 1988, described a family of immunosuppressive drug specific binding proteins in the cytosols of target tissues of immunosuppressive drug action. Several of these proteins, including a 34–37 kDa protein and a 50–54 kDa protein exhibited specific binding to CsA. In U.S. Ser. No. 07/521,074, filed May 9, 1990, as well as in the abovementioned '176 application, Soldin et al. described a novel 50–54 kDa protein that bound FK-506 in addition to CsA, and another protein that specifically bound CsA (an about 17–18 kDa protein, but not FK-506. Contrariwise, an about 10–12 kDa protein binds RAP and FK-506, but not CsA. More recently, in U.S. Ser. No. 07/682,067, filed Apr. 7, 1991 (U.S. Pat. No. 5,322,772, issued Jun. 21, 1994) Soldin showed that RAP, a macrocyclic triene immunosuppressive drug in the chemical class of FK-506, specifically binds, not only to all proteins to which FK-506 specifically binds (10–12 kDa and 34–37 kDa proteins), but also to the about 50–54 kDa protein to which RAP, FK-506 and CsA specifically bind. Finally, in U.S. Ser. No. 08/050,576, filed Apr. 21, 1993, (U.S. Pat. No. 5,345,845, issued Oct. 11,1994) Soldin described a novel 14.6 kDa protein that specifically binds both FK-506 and rapamycin, but not CsA. In all instances, the proteins identified and purified were used to develop binding protein assays with the required specificities. As will be detailed below, with the purification to homogeneity of individual members of a family of immunosuppressive drug binding proteins (hereinafter, "immunophilins") with a variety of drug binding specificities it is now feasible to tailor protein binding assays to particular classes of immunosuppressive drugs, as well as to use the different purified immunophilins for a variety of useful purposes, as will be described below.

SUMMARY OF THE INVENTION

This invention relates to immunophilin proteins purified from the cytosols of normal or transformed mammalian lymphoid tissues or cells or recombinantly-made, "immunophilins" being defined herein as cytosolic proteins that bind specifically (see definition of "specific binding" below) biologically active immunosuppressive drugs of the chemical classes of the cyclosporines, FK-506 and rapamycins, or analogues, derivatives or metabolites thereof. This invention also relates to methods for the quantification of such immunosuppressive drugs in fluid samples using the aforementioned purified proteins as reagents in protein binding assays. The invention also relates to the use of such protein reagents for other purposes, such as the identification in, and isolation from, a mixture of natural products novel immunosuppressive drugs.

In one aspect of the invention, there is provided compositions, and methods of producing same, representing purified immunophilins of molecular mass ranges 2.4–3.0 kDa, 4.5 kDa, 10–12 kDa, 34–37 kDa, 50–54 kDa, 80–100 kDa, and greater than about 120 kDa.

A homogeneous 10–12 kDa immunophilin that specifically binds compounds of the class of FK506 and rapamycin, but not CsA, has a pI of about 8.5–9.0, a dissociation constant of about 1–2 nM and a specific binding activity of about 0.5 nmol/mg for FK-506.

A homogeneous 50–54 kDa protein unexpectedly binds CsA, as well as FK-506 and RAP, and exhibits the following physical and chemical characteristics: pI 6.5–6.8; dissociation constant 1–10 nM and specific binding activity of about 0.3 nmoles/mg for FK-506; dissociation constant of about 60–65 nM and specific binding activity of about 3–4 nmoles/mg for CsA; dissociation constant of about 0.1–0.2 for rapamycin; approximate amino acid composition (mole %): ASX 11.66, GLX 12.82, SER 7.79, HIS 0.99, GLY 11.31, THR 5.30, ALA, 6.34, ARG 3.96, TYR 4.66, VAL 4.97, MET 1.46, PHE 4.17, ILE 5.95, LEU 8.97, LYS 4.71 and PRO 4.94 (CYS and TRP not determined); minimum molecular weight from amino acid analysis, 52,172; C-terminus amino acid sequence (SEQ ID NO:1) ASP-GLN-ILE-VAL-GLU-LEU-THR-VAL-GLY-ASN-ASN-ASN-. This protein, unlike the 10–12 kDa immunophilin, also inhibits the activity of cAMP-dependent protein kinase, but not of tyrosine protein kinase or protein kinase C. This protein, unlike the 10–12 kDa immunophilin, exhibits no rotamase activity with substrates and under conditions under which the 10–12 kDa protein does (Soldin, U.S. patent application No. 08/224,868, allowed).

In another aspect, a novel, homogeneous 34–37 kDa protein is described that, like the 50–54 kDa immunophillin, specifically binds FK-506, RAP and CsA.

In yet another aspect of the invention, there are provided methods of use of the aforementioned purified immunophilins as free or immobilized reagents in quantitative assays for the presence and amounts of the aforementioned and related immunosuppressive drugs in fluid samples.

In another aspect of the invention, immunophilins and their ligands are assembled into mercantile kits.

In still another aspect of the invention, the immunophilins of the invention are used as capture reagents to isolate from mixtures of natural products such as microbial extracts or culture media novel immunosuppressive drugs, or to isolate metabolites of immunosuppressive drugs from body fluids.

These and other features and advantages of the invention will be apparent from the following description of the preferred embodiments thereof, and from the appended claims.

DETAILED DESCRIPTION OF THE DRAWINGS

Figure 31:
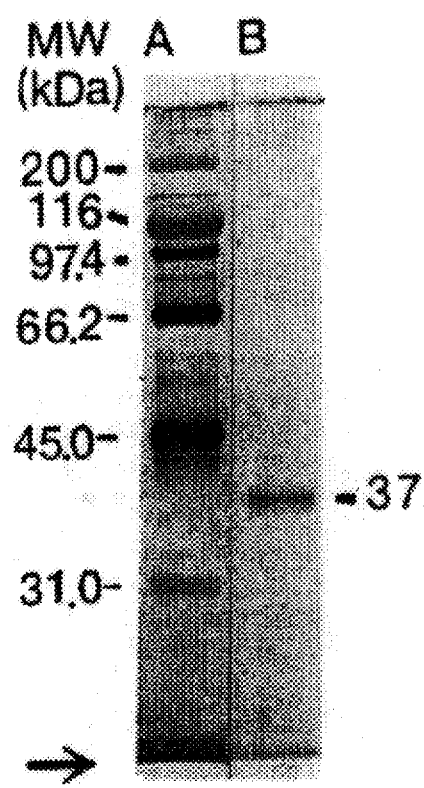

FIG. 31 shows SDS-Polyacrylamide gel electrophoresis of the 34–37 kDa immunophilin. Lane A: Bio-Rad protein markers. Lane B: 37 kDa protein. Arrow: Dye front.

Figure 32:
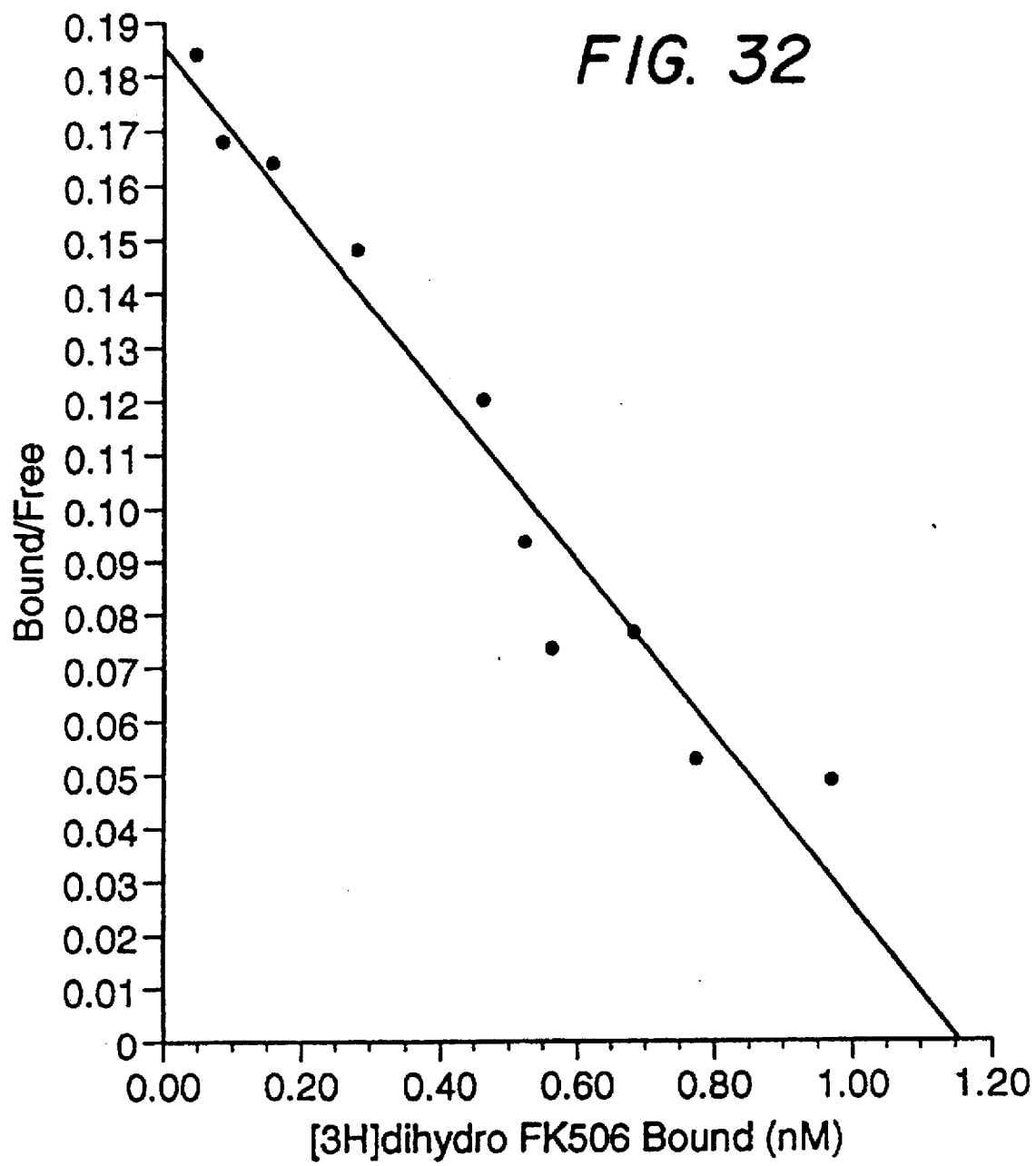

FIG. 32 shows Scatchard plot of [$^3$H]dihydro FK506 binding with the purified 34–37 kDa immunophilin. The Scatchard experiments were carried out as described in Example 28 using [$^3$H]dihydro FK-506 (0.25–20 nM). Curves are computer-determined best fits using a linear curve fitting program.

Figure 33:
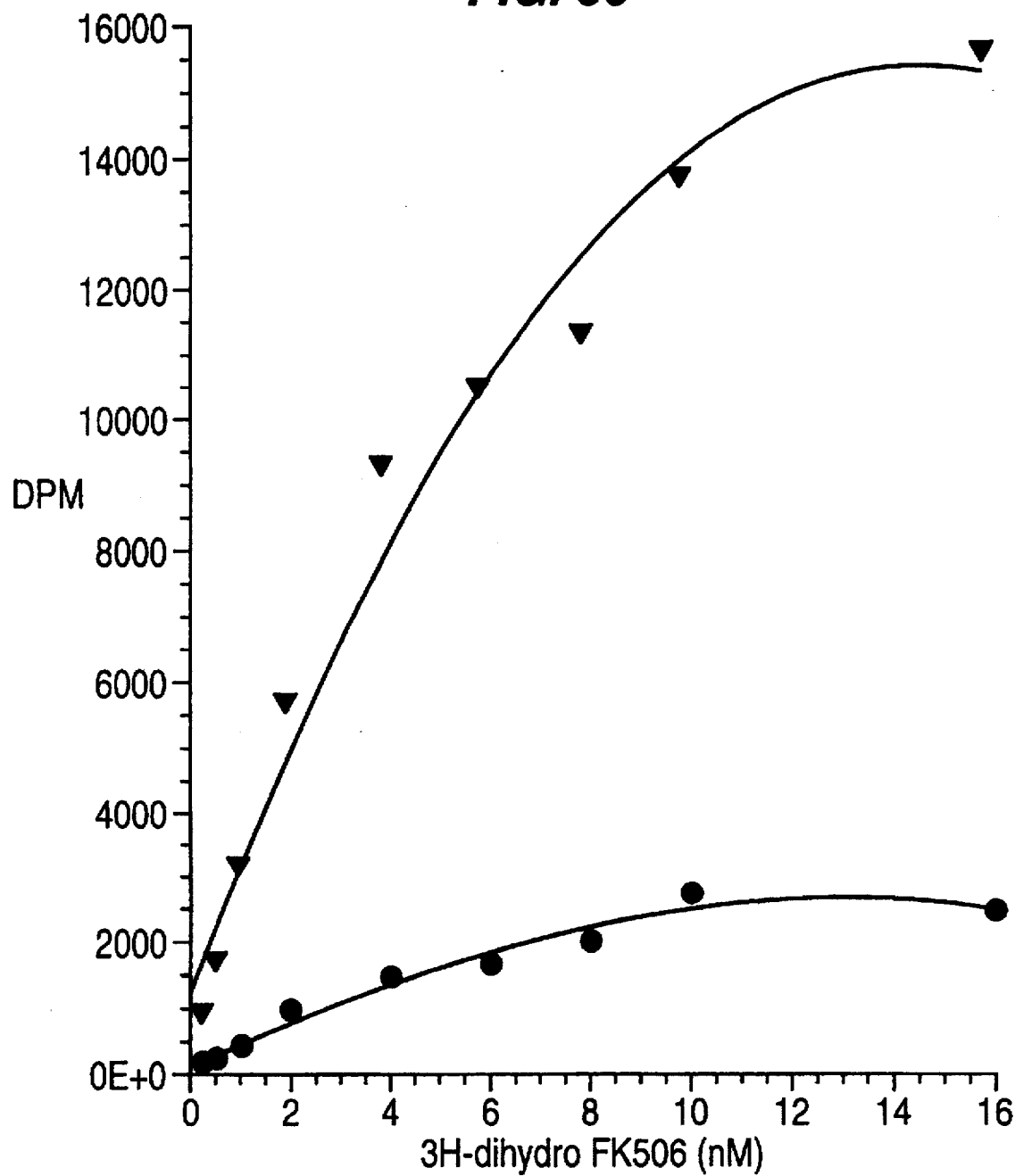

FIG. 33 shows the saturation isotherm of [$^3$H]dihydro FK506 binding with the purified 34–37 kDa immunophilin fraction. (P—P): Specific binding of [$^3$H]dihydro FK506 (DPM); (J—J): Nonspecific binding of [$^3$H]dihydro FK506.

DETAILED DESCRIPTION OF THE PREFERRED EMBODIMENTS

There is general agreement that the term "receptor" refers to a macromolecule capable of recognizing and selectively binding with some ligand, and which, after binding the ligand, is capable of generating some chemical or physical signal that initiates the chain of events leading to the biological response. Blecher, M., et al., "Receptors and Human Disease", Williams & Wilkins, Baltimore, 1981, Chapter 1. It is thus an important aspect of this invention that the water-soluble cytosolic, non-immunoglobulin immunosuppressive drug binding proteins ("immunophilins") described herein and used in the protein binding assays of the invention exhibit at least one of the key characteristics of a natural receptor protein, namely, specific, high affinity and reversible binding of the drug ligand. It is neither known nor germane to this invention whether or not the cytosolic drug binding proteins described herein are the "physiological" receptors for drugs of the cyclosporine, FK506 and rapamycin classes that lead to their pharmacological effects.

Water-soluble specific binding proteins suitable for use in assays carried out in accordance with the invention are prepared from cytosolic extracts of target tissues of immunosuppressive drug action, namely, mammalian lymphoid tissue or cells such as human peripheral blood lymphocytes, monocytes or leukemia cells, bovine thymus gland, human or calf spleen cells, and human or animal thymoma or lymphoma cell lines. Preferred are lymphocytes, either from solid organs or from tissue culture lines. Most preferred organs are spleen and thymus. Most preferred established cell lines are normal or tumor human mononuclear leukocytes. It should be emphasized that the particular cell source of the binding proteins of the invention are not important from the perspective of binding assays; the purified protein need only exhibit the desirable binding properties mentioned above and to be described in greater detail below.

The cytoplasm is defined in the art as the non-particulate, non-membranous portion of a cell. The soluble cytoplasm (i.e., cytosol) is defined operationally in this art and herein as that fraction of a cell extract that remains in the supernatant fluid following centrifugation at high g-forces, i.e., greater than 20,000×g, for at least 15 minutes, preferably greater than about 40,000×g for 30 minutes, most preferably greater than about 100,000×g for 60 minutes. The immunophilins of the invention are found in such ssupernatant fluids. It should be emphasized that the term "immunophilin" as used herein is not intended to include immunoglobulin proteins such as IgG, IgM or the like raised against immunosuppressive drug antigens.

The following art-recognized techniques for disrupting cells and isolating a cytosolic macromolecule are suitable in practicing this invention. Generally, isolated cells are disrupted by one or more methods such as: (1) one or more freeze-thaw cycles at low temperatures in buffered hypotonic solution, followed by gentle homogenization in a glass/glass or Teflon/glass homogenization tube; (2) brief sonication at high intensities at low temperature; (3) hypotonic lysis at a low temperature, followed by repetitive forcing of the lysate through a narrow orifice (e.g., a 26 gauge hypodermic needle); or (4) direct homogenization in hypotonic solution. Most preferred for isolated cells is a method wherein a pellet of white cells is frozen at a low temperature in a hypotonic salt solution, then thawed abruptly to lyse the cells, and the lysate gently homogenized in a Teflon/glass homogenizer or briefly sonicated. Solid tissues such as spleen or thymus glands can be homogenized at 4° C. using a Polytron Tissue Homogenizer and/or a Potter-Elvejhem type Teflon/glass homogenizer in at least 3 volumes of a hypotonic buffer such as a phosphate buffer at pH 7 containing a heavy metal chelator (typically EDTA or EGTA), a disulfide bond protector such a 2-mercaptoethanol, and an inhibitor of proteolysis such as PMSF.

The thus-disrupted cell preparations are fractionated by art-recognized methods to isolate cytosolic proteins. In a preferred technique, the cell homogenate is made up in sucrose (0.25–0.32M sucrose final concentration), then centrifuged at 20,000–40,000×g for 30–90 minutes at 4° C. in vacuo; the immunophilins are in the supernatant fluid, and can be stored frozen (e.g., at −70° C.) until ready for use. In another preferred technique, cells are disrupted by brief sonication while in an isotonic buffer (e.g., 0.15M KCl, 20 mM Tris.HCl buffer, pH 7.2, 5 mM 2-mercaptoethanol), the cytosol is recovered by centrifugation at 100,000×g at 4° in vacuo; the immunophilins are in the cytosol, which can be frozen until use. In yet another useful technique, cell debris, after adjusting the mixture to isotonicity, is removed from homogenates by a preliminary centrifugation at 500–1000×g for 10–20 minutes, and the cytosol is obtained by centrifugation of the supernatant fluid at 100,000–150,000×g for 30–90 minutes at 4° C. in vacuo; the immunophilins are in the supernatant fluid. It is clear that, whatever the cell fractionation method, the immunophilin proteins will be located in the water-soluble cytosolic portion of the disrupted cell preparation.

Although the cytosol can be used as such in protein binding assays carried out in accordance with the invention, it is highly preferred that immunophilins be purified and concentrated prior to use. Ultrafiltration with Centricon (™) Microcontrators (Amicon, Beverly, Mass.) can be used to preliminarily fractionate immunophilins from cytosols. For example, Centriprep-50 (™) produces a fraction containing proteins of molecular masses of 10 to 30 kDa. Sequential combinations of conventional size exclusion, HPLC, affinity, ion exchange and hydrophobic interaction chromatographic techniques, and isoelectric focusing and electrophoretic techniques can be used to purify immunophilins to homogeneity, as will be described in detail in the examples below. Such fractionation techniques are disclosed, inter alia, in Handschumacher et al., 1988 above; Koletsky et al., *J. Immunol.*, 137:1054 (1986); Harding et al., 1986 above; and Agarwal et al., *Transplantation*, 42:627 (1986), which are incorporated by reference to the extent that they disclose soluble cell protein fractionation methods. Molecular sieves for fractionating proteins in the 3,000–150,000 molecular weight range include Sephadex G-75 and G-100 (Pharmacia Fine Chemicals, Piscataway, N.J.) and Bio-Gel P-100 (Bio-Rad, Richmond, Calif.). A preferred affinity column is Matrex Gel Blue A (Amicon Corp., Denvers, Mass.) on which immunophilins can be readily fractionated with salt gradients. For HPLC, instruments made by Beckman Instruments Co. and using a Bio-Rad BioSil SEC 125 column are preferred. For isoelectric focusing and the determination of pI values, the ROTOFOR instrument of Bio-Rad is preferred. For cation exchange chromatography, a weak cation exchange matrix (Beckman's TSK CM-25W Spherogel) is preferred. Hydrophobic interaction matrices can also be used to fractionate proteins. Purity of isolated proteins can be assessed by SDS-PAGE chromatography. Any sequence or combination of the aforementioned methods can be used according to this invention as long as proteins of suitable purity are obtained; these combinations are exemplified below in the Examples. For the purposes of this invention, a protein is deemed to be "purified" if it produces a single, sharp chromatographic peak or single, narrow SDS-PAGE band.

Analytical data on purified immunophilins may be obtained conventionally. Association constants, specific binding activities, and numbers and types of binding sites can be obtained from Scatchard and Hill plots, using EBDA and LIGAND software. Isoelectric points ("pI") can be obtained by isofocussing techniques. To obtain amino acid composition data, samples can be hydrolyzed by HCl gas in the presence of internal standards (e.g., norvaline and sarcosine), the products derivatized with a fluorescent reagent, and the derivatized amino acids separated on a Hewlett-Packard Amino Quant Analyzer. To sequence protein chains, a sample of the protein is reduced and pyridinylated (to protect cysteine residues), freed of reductant and salts, then cleaved by controlled tryptic digestion. Tryptic peptides can be resolved by RP-HPLC and sequenced by standard methods. N-terminus and C-terminus amino acid sequences mar be obtained by art-recognized techniques, including Edman degradation.

Immunophilins can also be synthesized by art-recognized recombinant DNA techniques (Olds et al., Principles of Gene Manipulation, 3d. ed., Blackwell, Boston, 1985, Ch. 1–12; Sambrook et al., Molecular Cloning: A Laboratory Manual, Cold Spring Harbor Laboratory, N.Y., 1989). In brief, immunophilin cDNA may be cloned from purified mRNA or from a cDNA cloning library using oligomers of a sequence deduced from tryptic peptides of at least 7 amino acids in length (see Example 19 below), to produce large amounts of the protein. An expression vector may be constructed containing the immunophilin cDNA, promoter and gene regulation sequences, and then inserted into transformed eukaryotic or prokaryotic expression systems. The immunophilin can be isolated from growth media by the methods according to the invention.

To determine effects of immunophilins on enzyme activities, the following protocols can be employed. For detection of effects of a immunophilin on a cyclic AMP ("cAMP")-dependent protein kinase, mixtures containing enzyme, protein substrate (e.g., a histone or a partially dephosphorylated casein), phosphorylating reagent $\gamma$-$^{32}$P-ATP, activator cAMP, cofactor $Mg^{2+}$, and an immunophilin in a phosphate buffer at pH 6.8 are incubated for an appropriate period, and reaction ended by adding a heavy metal chelator reagent and maintaining the mixture at 100° C. for a brief period (e.g., 2 minutes). Radio-labeled substrate protein may be detected by radioautography of the gel after SDS-PAGE separation of the reactants and products. Autoradiograms may be quantified by a densitometer using transmittance scanning at 600 nm. Immunosuppressive drugs (e.g. 60–600 nM) may be added to incubation mixtures to determine their effect, if any, on the immunophilin effect.

Autophosphorylation of lck tyrosine-specific protein kinase, which is activated by the CD 4/CD 8 receptor early in T-cell activation, in the presence of immunophilins may be tested according to the procedure of Veillette et al., *J. Exp. Med.*, 170:1671 (1989); Veillette et al., *Nature*, 338:257 (1988).

Protein kinase C activity may be analyzed using the rat brain enzyme and a procedure developed by Amersham Corp. Briefly, the enzyme catalyzes the transfer of the $\gamma$-phosphate from $\gamma$-$^{32}$P-ATP to a threonine-containing peptide substrate in the presence of an enzyme activator such as phorbol 12-myristate 13-acetate, cofactors $Mg^{2+}$ and $Ca^{2+}$, and a mixed micellular suspension containing L-$\alpha$-phosphatidyl-L-serine and the phorbol. Phosphorylated peptide is separated on binding paper, washed with dilute weak acid, and the phosphorylation of the peptide substrate detected and quantified by scintillation counting. To test for effects of immunophilins on this reaction, the immunophilin±immunosuppressive drug is present during the incubation.

Rotamase activity (cis-trans peptidyl-prolyl isomerase activity) may be assayed in purified immunophilins using the methods of Fischer et al., *Nature*, 337:476 (1989) and Lange et al., *Nature* 4 331:453 (1988), which are incorporated herein by reference. Short peptide substrates containing proline used as substrates are shown in Table 8, Experiment 18, below.

For the purpose of a protein binding assay according to this invention, an immunophilin is deemed acceptable if: (1) the protein binds labeled immunosuppressive drug to a statistically significant extent (as this expression is understood in the ligand binding protein art, based upon the method of detection, i.e., radioactivity, fluorescence polarization, chemiluminescence and the like; (2) unlabeled drug and biologically active analogues, derivatives and metabolites thereof reversibly compete with labeled drug for specific binding sites on the protein; and (3) the signal-to-noise ratio, i.e., the ratio of total binding of labeled drug to nonspecific binding of this molecule (as these terms are defined in *Principles of Competitive Protein Binding Assays* infra) is at least 1.1, preferably at least 1.2.

Labeled Drugs

For the protein binding assays in accordance with the invention, labeled immunosuppressive drugs are required. Cyclosporines labeled with $^3H$, $^{125}I$ or fluorescein are available commercially. [$^3H$] CsA (label positions : 95% [Abu-$^3$H]-cyclosporine and 5% ([N-methyl-$^3$H]-Sar) cyclosporine is available from Sandoz Pharmaceuticals, Hanover, N.J. or Sandoz Ltd. Basel, Switzerland (SANDIMMUNE®). [$^3H$]-Dihydro CsA is prepared by catalytic reduction of the MeBut double bond in CsA by the Wilzbach procedure with $^3H_2$ (New England Nuclear Corp., Boston, Mass.). [$^{125}I$]-CsA is sold by Immuno Nuclear Corp., Stillwater, Minn., 55082 as part of their INCSTAR kit as CYCLOTRAC®. MeBut-β-[$^3H$]-CsA, specific activity 5–20 Ci/mmol, is available from the Amersham Corp., Arlington Heights, Ill. For fluorescent polarization detection methods, CsA-fluorescein tracer, suitable for use with the TDX instrument, is available from Abbott Laboratories, Abbott Park, Ill. CsA can also be labeled with fluorescein by reaction with fluorescein isothiocyanate according to Mahoney, W. C., et al., U.S. Pat. No. 4,427,035. $^{125}I$-labeled-histamine-CsC can be prepared according to the method of Wong et al., *Clin. Chem.*, 32:492 (1986)]. CsA, CsB, CsC and CsD and CsA metabolites for use as standards are available from Sandoz Pharmaceuticals, Hanover, N.J.

[$^3H$]-Dihydro FK-506 can be prepared by exposure of native FK-506 (Fujisawa Pharm. Co., Osaka, Japan) to $^3H_2$ in the presence of a reducing agent (e.g., Tris-(triphenyl phosphine) rhodium I chloride), followed by purification by normal and reverse phase chromatography (Amersham Corp.). Purification can be assessed by TLC. One preparation of [$^3H$]-dihydro FK-506 was 98+% pure by three different TLC systems, and had a specific activity of 51 Ci/mmol (63.2 mCi/mg). $^{125}I$-FK-506 can be prepared by brief reduction by chloramine-T in the presence of $Na^{125}I$. $^{125}I$-labeled histamine-FK-506 can be produced according to Wong et al. 1986 above. FK-506 may be labeled with a fluorophore by art-recognized methods (Mahoney, W. C. et al., above).

Native rapamycin (Wyeth-Ayerst Pharm. Co., Princeton, N.J.) is labeled with $^3H$ by art-recognized methods such as exposure of native rapamycin to tritium gas in the presence of a reducing agent, followed by purification by normal and/or reverse phase chromatography. Purification can be assessed by TLC. One preparation of [$^3H$]-rapamycin, which was 98+% pure as determined by TLC, had a specific activity of 13.6 Ci/mmol.

Chemiluminescent labels such as water soluble 1,2-dioxetanes that are activated by cleavage by alkaline phosphatase or α- or β-galactosidases have been described by Bronstein et al., *J. Biolumin. Chemilumin.* 2:186 (1988)] and Voyta et al. *Clin. Chem.* 34:157 (1988)], and can be purchased from Tropix, Inc. Bedford, Mass. 01730 (cat. no. ED-010).

Protein Binding Assays Using an Immunophilin

A protein binding assay ("PBA") carried out in accordance with this invention can be performed by solution phase or solid phase methods. The basic principle underlying each method is the same. Briefly, in a competitive PBA, a competition equilibrium is set up between a tracer amount of unlabeled drug and the corresponding drug in unknown samples containing the drug or biologically-active metabolites for binding to specific binding sites on an immunophilin. Following attainment of equilibrium, the amount of labeled drug bound to the immunophilin is determined. The amount of labeled drug bound will be reduced in proportion to the amount of analyte in a biological sample being analyzed. The quantitative relationship between the reduction of immunophilin-bound labeled drug and the concentration of the analyte in the unknown sample is determined by reference to a standard calibration curve. To generate such a curve, a fixed amount of binding protein is contacted with a fixed tracer amount of the labeled drug in the presence of zero-to-supersaturating concentrations of standard drug. It is preferred that this supersaturating concentration be several orders of magnitude greater than the association constant, $K_a$, of specific binding, and this fraction, which is termed "nonspecific binding" ("NSB"), is assumed to be the same for all ligand concentrations, as NSB is assumed to be a linear function of ligand concentration. The amount of NSB binding is subtracted from each data point in order to obtain "specific binding". The amount of labeled drug bound to an immunophilin need not be determined directly; it may be determined by subtracting from the total amount of label added remaining unbound in the solution at equilibrium.

Solutions of Immunosuppressive Drugs

Standard solutions of immunosuppressive drugs for use in the assays according to the invention are prepared as follows. Stock solutions of drugs (typically containing 10–20 μg/mL, but other concentrations may be appropriate) may be prepared in a polar solvent miscible with water (e.g., 50% ethanol). For use in producing a calibration curve, aliquots of this stock standard solution may be delivered to assay tubes and the solvent removed (stream of $N_2$ or in vacuo), or the stock solution may be appropriately diluted in drug-free whole blood, plasma or serum, to produce a working standard. Further dilutions in drug-free whole blood, plasma or serum are made to produce a series of diluted standard solutions with immunosuppressive drug concentrations ranging from 0 to 2000 ng/mL. The concentration of solvent remaining in the working standard solutions are not critical as long as they are without influence on the binding reactions. Standard working solutions of drugs at the highest level can be stored at 4° C., but should be used within 24 hours of its preparation. Alcohol is a preferred solvent and is selected from among $C_1$ to $C_8$ primary, secondary or tertiary alkanols. Acetonitrile is also suitable as a solvent for stock solutions of cyclosporines. Most preferred in 50–70% aqueous ethanol.

Extraction of Drugs from Fluid Samples Prior to Assay

Immunosuppressive drugs and their metabolites, analogues and derivatives ("analytes") in patient samples such as whole blood, serum or plasma must be placed in a form suitable for assay, in particular to separate the drug from interfering chemicals such as other therapeutic drugs. By "metabolite" is meant a product of the in vivo metabolism of an immunosuppressive drug (see Background section). By "analogue" is meant an immunosuppressive drug in which a naturally occurring atom (other than a H atom) is replaced by a non-natural atom, such as dihydro CsA or FK506. By "derivative" is meant an immunosuppressive drug to which a foreign chemical structure has been attached, such as the C32 amines, acylesters, ethers and the like of FK506.

Separation of analytes from interfering chemicals can be accomplished by extraction procedures. For example, analyte-containing fluid samples are extracted with about 20 volumes of an amphipathic solvent, and the precipitated proteins sedimented by centrifugation. By "amphipathic organic solvent" is meant a liquid organic compound having both hydrophilic and hydrophobic moieties. Preferred amphipathic alcohols are lower alkanols (e.g., $C_1$–$C_6$ straight or branched chain, primary, secondary or tertiary alcohol) or acetonitrile. It is also suitable to extract an aliquot of whole blood with an amphipathic surfactant solution. For example, 5–10 volumes of 20 mm Tris buffer, pH 8.5, containing 0.03% (v/v) Tween 20 polyoxyethylene (20 sorbitan monolaurate) is a suitable extractant (Felder, R. A., supra). Drugs and their metabolites can also be extracted from serum-containing samples by the method of Yee et al., *Clin. Chem.*, 28:2269 (1982), using a Baker 10 extraction system (SPE, J. T. Baker, Phillipsburg, N.J.) and small cyano disposable extraction columns (3 mL capacity, 40 mm diam.). In another technique suitable for whole blood, which may also contain other drugs that may produce spurious results, a sample of whole blood is extracted with an amphipathic solvent, e.g., 2 volumes of methanol and one volume of water, the precipitated proteins are removed by centrifugation, and the supernatant fluid containing the drug either filtered through Sep-Pak $C_{18}$ sample preparation cartridges (Waters Chromatography Division, Milford, Mass.) according to the method of Charles et al., *Therap. Drug Monitor*, 10:97 (1988), or through a reversed phase hydrophobic adsorbent matrix such as the BOND ELUT® sorbent minicolumns (Varian Assoc., Harbor City, Calif.). The latter column of the cyclohexyl type separates FK-506 from CsA, as well as from immunosuppressive drugs such as prednisolone. The BOND ELUT® column, in conjunction with the above-described extraction step, produces background levels of <1 µg/L, the minimum detectable concentration in the assay methods according to the invention. Void volumes from these columns are taken to dryness, and analyte drugs assayed as described above and below.

In a method highly prepared for the extraction of CsA from whole blood, 300 µL of a blood diluted with 100 µL of water are extracted with 750 µL of a 9:1 mixture of acetonitrile and methanol. Precipitated proteins are removed by centrifugation (5,000×g for 15 mins.), and the supernatant fluid is passed through a preconditioned C18 column (Analytical Bond Elute (C18) sorbent column, Varian above. The C18 sorbent column (500 mg, 3 mL capacity) is preconditioned by two washes with 2 mL of a 3:1 mixture of ethyl acetate and isopropanol and with 2 mL of 70% aq. methanol. After passing the supernatant fluid through the column, the column is washed with 2 mL of 70% methanol and 2 mL of a 1:99 mixture of acetone and hexane. CsA is then elected from the column with 3 mL of a 3:1 mixture of ethyl acetate and isopropanol. The eluate is aliquoted into three 1 mL portions, and each aliquot is used for a binding assay after evaporating the solvents.

Solution Phase Assay Procedure

1. Binding Step

Aliquots of extracts containing unknown analyte or standards or labeled analyte (the sizes of these aliquots are dependent upon the label, but typically range from 0 µL to about 1000 µL when using $^3$H- or $^{125}$I-labeling), are added to reaction tubes and the solvent removed at a slightly elevated temperature using a gentle stream of an inert gas, typically 40° C. and $N_2$ gas, or in vacuo. To each reaction tube is added a fixed tracer amount (e.g., 0.5 nM, 50–100, 000 CPM) of labeled drug in a small volume (typically 50 µL) of solvent.

Thereafter, an aliquot of an appropriate dilution of the immunophilin preparation in binding buffer (e.g., 100–200 µL) is added to the reaction tubes, and the mixture is incubated with shaking to allow the analyte preparation to reach equilibrium binding with the protein. An aliquot of labeled drug is added to the test tube and mixed. The tubes are then incubated for a period suitable for reaching equilibrium binding, ranging from 0 hour (control) to 16 hours, preferably 30–90 minutes, at a slightly elevated temperature, typically, 30°–40° C. Nonspecific binding tubes are also prepared by adding immunosuppressive drug-free extract to the volume of buffer equal to the volume of the binding protein aliquot, and adding a supersaturating concentration (e.g., 200-fold molar excess) of standard drug in a small volume (e.g., 50 µL). The composition of the binding reaction buffer is not critical. A preferred binding buffer is 20 mM Tris buffer, pH 7.2, containing 5 mM β-mercaptoethanol, 0.05% $NaN_3$ as preservative, and about 7.5% (w/v) fetal calf serum to reduce nonspecific binding.

2. Separation Step

When using any detection methods other than fluorescence polarization methods (which can distinguish protein-bound fluorescein-labeled drug from unbound fluorescein-labeled drug when both are together in solution, see infra), it is necessary to separate the protein-bound labeled drug from free labeled drug.

Among the separation methods useable for this purpose are:

Method A: The contents of the binding reaction mixture are diluted with ice-cold buffer, preferably about pH 7.4, the contents filtered through a glass fiber filter such as Whatman GF/B filters (Whatman Paper, Maidstone, England), then washed with ice-cold buffers; the membrane retains the protein-bound labeled drug.

Method B: This method is the same as Method A, except that filtration is carried out using a microporous filter, e.g., a nitrocellulose 0.22 µm filter (Millipore Corp., Bedford, Mass.) prewashed with a solution of carrier bovine serum albumin or γ-globulin to block nonspecific binding sites; protein-bound drug is retained by the membrane.

Method C: Following dilution of the binding reaction mixture with ice-cold buffer, a suspension of charcoal particles coated with a carrier protein (albumin or γ-globulin) to block nonspecific binding is added to the tube, the mixture vortexed, then centrifuged in the cold to sediment the charcoal particles. The supernatant fluid contains the protein-bound labeled drug.

Method D: Following dilution of the binding reaction mixture with ice-cold buffer, a suspension of polyethylene glycol particles (M. W. 15,000–20,000), e.g., 1.0 mL of a 30 mg/mL suspension, plus a solution of a carrier protein, preferably about 1.0 mg of serum albumin or γ-globulin, are added, and the resulting suspension is mixed. The sediment is collected by centrifugation and the supernatant fluid discarded. The pellet contains the protein-bound labeled drug.

Method E: Following dilution of the binding mixture with ice-cold buffer, carrier albumin or γ-globulin is added to the tube, and trichloroacetic acid added to a final concentration of about 5–10% at 0°–4° C. to precipitate all proteins. The precipitate is centrifuged and the supernatant fluid discarded. The pellet contains the protein-bound labeled drug.

Method F: Protein-bound labeled drug is separated from the unbound species in the binding mixture using minicolumns of a molecular sieve matrix, such as LH-20 Sephadex (Pharmacia Fine Chemicals, Piscataway, N.J.).

Washing the column with a small volume (e.g., 0.5 mL) of phosphate-buffered saline, preferably about pH 7.4, will elute, in the void volume the protein-bound labeled drug.

Sephadex LH-20 is a weakly hydrophobic matrix, and free labeled CsA, FK-506 or rapamycin will be retarded in such a matrix.

When $^3$H is the tracer in Methods A and B, the filters are placed in liquid scintillation counting (LSC) vials, and an aliquot of an aqueous-organic solvent phase combining scintillation system (e.g., PCSS, Amersham) is added. The vials are vortexed, and the amount of radioactivity quantified by liquid scintillation spectrometry (LSS). When using Method C, an aliquot of the supernatant fluid is added to LSC vials, diluted with, e.g. PCSS, vortexed, then counted by LSS. When using Methods D and E, the pellet is resuspended in PCSS, or dissolved in NaOH and diluted in PCSS, added to LSC vials, then counted by LSS. When using Method F, an aliquot of the void volume is diluted in PCSS and added to LSC vials, then counted by LSS.

When $^{125}$I is the tracer, the filters from Methods A and B, the supernatant fluid in Method C, the pellets from Methods D and E, or the void volume from Method F, are placed in a tube, and the radioactivity is quantified in a gamma counter.

When chemiluminescent labels are employed, in separation Methods A and B supra, the filters are placed on a sheet of Whatman blotting paper. The filter is then soaked with a solution (500–1,000 μg) of 3-(2'-spiroadamantane)-4-methoxy-4-(3''-phosphoryloxy)phenyl-1,2-dioxetane, disodium salt (AMPPD, Tropix, Inc., Bedford, Mass.) in an alkaline buffer containing MgCl$_2$. The filters are transferred to a piece of Mylar polyester film, and then to a black box containing instant film, such as Type 612 Polaroid film. After exposure of the film to the light for an appropriate period, the dark image is digitized using, for example, a black and white RBP Densitometer, Tobias Assoc., Inc., Ivyland, Pa.

In separation Method E, the pelleted suspensions are washed with pH 7.4 buffer, and once with an alkaline buffer (pH 7–10) containing MgCl$_2$. The pellets are then reacted with AMPPD in an alkaline buffer (pH 7–10) containing MgCl$_2$ until maximum luminescence is attained, typically in 15 to 30 minutes at 30° C. Thereafter, the luminescence from each tube is read in a luminometer, e.g., Turner 20E Luminometer or Berthold Clinilumat Luminescence Analyzer.

In separation Methods C and F, the supernatant fluid or the void volume respectively, are reacted with AMPPD at an alkaline pH (pH 7–10) in the presence of MgCl$_2$. After maximum chemiluminescence has been attained, typically in 15 to 30 minutes at 30° C., the luminescence is estimated in a luminometer.

Where the drug is conjugated to an α- or β-galactosidase, 3-(2'-spiroadamantane)-4-(3''-O-galactopyranoside)phenyl-1,2-dioxetane will be the substrate.

The principle underlying fluorescence polarization-based assays is described by Robbins et al., *J. Clin. Lab. Anal.*, 2:62 (1988) and in Abbott Laboratories 55TDX Instruction Manual. Displacement experiments using $^3$H-labeled CsA and fluorescein-labeled CsA have demonstrated that both molecules compete for the CsA binding sites on a cytosolic cyclosporine binding protein. This observation provides the basis for using fluorescence polarization measurements to determine the amount of immunosuppressive drugs bound to their immunophilin. In brief, in this assay, a beam of plane polarized light is used to excite the fluorophore (e.g., fluorescein), and the resulting polarized fluorescent signal is measured. The assay depends on the principle that molecules in solution randomly move and rotate at a rate that is inversely proportional to their size. Small molecules (e.g., CsA-fluorescein) rotate freely and rapidly, whereas large molecules (e.g., protein-bound CsA-fluorescein) will not rotate freely, or as freely.

In the fluorescence polarization binding protein-based assay carried out in accordance with this invention, fluorescein-labeled CsA, FK-506 or rapamycin will not produce polarized fluorescent signal as these molecules rotate freely, whereas the same molecules bound by the cyclosporine binding protein will give a polarized fluorescent signal as they are not free to rotate. That is, polarization increases as molecular size increases.

The assay system thus involves a standard competitive protein binding assay with incubation of a sample containing immunosuppressive drug analyte, fluorescent-labeled drug (e.g., CsA-fluorescein), and a purified immunophilin. The intensity of the polarized fluorescent signal is inversely related to analyte concentration. Dadliker et al., *Methods Enzymol.* 48:380 (1978). Therefore, if a sample contains a low concentration of drug analyte, after the competitive binding reaction reaches equilibrium there will be a high concentration of bound tracer (e.g., CsA-fluorescein) in the reaction mixture, and polarization will be high. Conversely, if there is a high concentration of drug analyte in the patient sample, after the competitive binding reaction attains equilibrium, there will be a low concentration of bound tracer in the reaction mixture and polarization will be low. This method is most useful for measurement of small molecules, which produce the greatest change in polarized fluorescence when the labeled molecule is bound to a receptor.

For the purposes of competitive PBA carried out in accordance with this invention, it is an important feature of the fluorescence polarization technique that protein-bound and unbound cyclosporine analyte can be distinguished in a single reaction mixture, i.e., without the need to separate the two components.

Abbott Laboratories has adapted the fluorescence polarization system to assays of multiple therapeutic drugs in its TDX System. The TDX system for the immunoassay of cyclosporine contains, in addition to the automated TDX instrument, a metabolite reagent pack containing, in separate vials, a buffer-surfactant solution, a solution of anti-CsA antibody containing a protein stabilizer, and CsA-fluorescein in a solution containing a surfactant and protein stabilizer. This TDX system is adaptable for a competitive protein binding assay carried out in accordance with this invention for immunosuppressive drugs by replacing the antibody vial with one containing a purified immunophilin according to the invention, and a protein stabilizer.

Drug standards, controls, and patient samples are placed in individual cartridges of the Abbott TDX instrument. The metabolite reagent pack is placed in the instrument. Thereafter, in an automated series of steps, standards, controls and patient samples are mixed with water-soluble binding protein and fluorescein-labeled drug, the mixtures are incubated at the preset temperature for a selected period until binding steady state is reached. The mixtures are transferred to glass cuvettes, and the fluorescent polarization signal measured. As noted above, the intensity of this signal is inversely related to the concentration of the analytes.

The fluorescent signals from patient samples are converted to $B/B_o$ ratios and these ratios are read off of a standard curve obtained by analyzing by fluorescence polarization a series of drug standards (see supra), wherein the ordinates for the standard curve are:

$[B_{(std)}/B_{(Ostd)}]100$ vs. log [Drug]

and $B_{(std)}$ is the fluorescence polarization of a bound standard CsA-fluorescein complex, $B_{(Ostd)}$ is that of a control sample and [Drug] is the concentration of immunosuppressive drug at each point.

Assay for CsA in Blood

In a highly preferred assay for CsA in whole blood, CsA is extracted from blood by the Bond Elute (C18) column procedure described above. To the solvent-free dried residue containing CsA is added 50 μL $^3$H-CsA (300,000 DPM in ethanol), 100 μL of binding protein solution and 100 μL of buffered 0.2% Tween-20. The mixture is mixed briefly (e.g., 10 secs.), then incubated with shaking for 20 mins. at 25° C. The procedure results in a quantitative recovery of CsA from the dried residue. A portion (200 μL) of this solution is added to a LH-20 Sephadex column (1.8 μL bed volume) equilibrated with 20 mM Tris buffer pH 7.2 containing 5 mM 2-mercaptoethanol and 0.05% sodium azide. Elution of the column with 1.25 mL of column buffer in 250 μL portions completely separates free from bound ligand CsA; bound ligand appears in the eluate. The bound radioactivity in the 1.25 mL column eluate is measured in 10 mL Optima Gold Scintillation Cocktail (Packard Chemicals, Meriden, Conn.) by liquid scintillation spectrometry. Non-specific binding is estimated using a 1 mg/mL concentration of unlabeled CsA; at this concentration, the unlabeled CsA displaces at least 95% of bound radiolabeled ligand from CsA binding sites and thus binding is used to define non-specific binding.

Solid Phase Assays

To immobilize an immunophilin, a supporting matrix, e.g., the bottoms of wells of a microtitre plate, the walls of a plastic tube, or polymeric beads, is coated with an immunophilin binding protein and nonspecific binding sites are blocked by brief exposure to a protein such as serum albumin or drug-free serum. A solution of labeled drug is contacted with the coated surface, incubated with gentle shaking, the solid surface washed with cold buffer (e.g., PBS), and the wash fluids aspirated to waste. Thereafter, in a displacement-type reaction an aliquot of fluid sample extract containing analyte drug is contacted with the immobilized immunophilin, and incubated with gentle shaking for a suitable period ranging from 0 hours (control) to 16 hours (analyte). The incubation fluid is aspirated to waste, and the solid surface is washed gently with cold buffer. Protein-bound labeled drug is extracted from the solid surface by surfactant or an amphipathic organic solvent, as described above for extraction of analyte drugs from fluid samples. The precipitated proteins are removed by brief centrifugation, and the amount of label in the supernatant fluid quantified as described above.

Although methods of use of the immunophilins according to the invention are described above in terms of a competitive or sequential PBA involving only a single protein species, it is within the scope of the invention to use such binding proteins in other types of binding assays for immunosuppressive drugs. For example, immunophilins of the invention can be used in simple or cassette-type "double receptor" specific binding assays. "Receptor" in this context refers to any specific binding protein and, in this context alone, also includes antibodies.

Double receptor binding assays have as their salient feature a first receptor specific for a second receptor, the second receptor ordinarily also capable of binding a ligand, generally the analyte (see, e.g., Litt, U.S. Pat. No. 4,092,408, which is incorporated herein by reference). In the present invention, the first receptor, which is advantageously immobilized, is a specific antibody directed to the purified immunophilin, the second receptor is the purified immunophilin itself, and the analyte ligand is an immunosuppressive drug. The binding assay with this system can be either of the direct competitive or sequential displacement types described above. In the latter type, in a first step the second receptor binds labeled drug and in a second step unlabeled drug displaces a portion of the protein-bound label, the degree of displacement being proportional to the amount of analyte present.

Alternate to the double receptor binding assays described above is a modification wherein the immunophilin second receptor is covalently bound to a small organic compound hapten, and the first receptor is an antibody directed against the hapten (see, e.g., Bunting, U.S. Pat. No. 4,271,140, which is incorporated herein by reference). In this system, the second receptor is an immunophilin and the hapten is an organic compound of a molecular weight of less than about 1,000; preferred are haptens such a fluorescein, acridine, dinitrobenzene, or naphthylamine. No more than 20, ordinarily 1 to 5, haptens per mole will be conjugated to an immunophilin.

Double receptor binding assays of either type improve accessibility of the analyte ligand to binding sites on the second receptor. The advantage of the modified double receptor binding assay is that binding affinities between the antibody and the hapten attached to an immunophilin will generally be greater than that between the two proteins without conjugated hapten. This advantage permits the use of insoluble double receptors in automated rechargeable binding assay systems.

For the convenience of the practitioner of the invention, it is within the scope of this invention to provide mercantile kits containing, in separate containers, in solution or immobilized on a solid support, one or more of the purified immunophilins proteins, standards, and labeled drugs.

The high affinities of the class of proteins of the invention for immunosuppressive drugs and their biologically-active metabolites, and the cross-reactivities of certain members of the class for compounds as similar in structure as the macrolide FK-506 and rapamycin or as dissimilar to the former as the cyclicundecapeptide cyclosporines, indicates that the proteins of the invention may be useful as affinity adsorbents for screening candidate compounds for potential therapeutic or diagnostic usefulness. For example, it is an embodiment of the invention to use the purified proteins of the invention as affinity adsorbents in the methods for screening extracts of fermentation broths of microorganism strains similar to those that produce cyclosporines, FK-506 and rapamycin for the presence of novel compounds of related structures. For rapid screens, the extract or broth is contacted with one or more binding proteins, preferably immobilized on a solid support, to form a protein-compound complex, the complex is washed to remove contaminating substances, the complex is dissociated, and the compound of interest isolated. Solid supports for such immobilization include polymeric (e.g., latex) beads or plastic surfaces. In another embodiment, such affinity adsorbents may be used for preparative-scale isolation of compounds identified by the aforementioned preliminary screen. For such purposes, the immobilized affinity adsorbent may be used in preparative column chromatography, in a batch mode, or in a continuous mode in which the adsorbent is first coated on the inner surface of plastic tubing as a reactor. Alternate to the use of binding proteins themselves as affinity adsorbents, binding proteins may be used to raise polyclonal and/or monoclonal antibodies (the latter increasing specificity), and the antibodies used as immunoaffinity adsorbents in the same manner as described above.

As mentioned above, identification and isolation from body fluids of metabolites of immunosuppressive drugs, particularly biologically active metabolites, is important for studies assessing the contributions of such metabolites to assay values. The purified binding proteins of the invention, particularly in immobilized form, can be used to capture metabolites of CsA, FK506 and rapamycin from body fluids in a manner similar to that described above for fermentation broths.

CsA, FK506 and rapamycin are produced by microorganisms. No counterpart mammalian compounds are yet known. In order to isolate and identify natural, mammalians immunosuppressive "drugs," the purified binding proteins of the invention, particularly in immobilized form, can be used to capture material ligands from mammalian body fluids and tissues by methods similar to those described above for the capture of drugs from fermentation broths and drug metabolites from body fluids.

Those skilled in the art of affinity adsorption will undoubtedly conceived of additional uses of the proteins of the invention that fall within the scope of this invention.

The above discussion of this invention is directed primarily to a general description of preferred embodiments and practices thereof. It will be readily apparent to those skilled in the art that further changes and modifications in the actual implementation of the concepts described herein can easily be made without departing from the spirit and scope of the invention as defined by the following claims. In order that those skilled in the art can more-fully understand this invention, the following examples are set forth. These examples are given solely for illustrative purposes, and should not be considered as expressing limitations unless so set forth in the appended claims.

EXAMPLE 1

Isolation of Cytosolic Cyclosporine Binding Protein

Leukopacks (obtained from the Blood Bank, Children's National Medical Center, Washington, D.C.) with a plasma-buffy coat volume of about 100 mL were diluted 3:5 (v/v) with phosphate-buffered saline, pH 7.4, (PBS) at 37° C. Diluted cells were layered over Histopaque-1077 (Sigma Diagnostics, St. Louis, Mo.) 3:8 (v/v) and centrifuged at 400×g for 30 minutes at 25° C. The upper layer of diluted plasma was aspirated to waste, and the white cell layer of mononuclear leukocytes at the Hypaque-plasma interface was carefully aspirated and retained. The button of erythrocytes and granulocytes was discarded.

The white cells were frozen at −70° C. and thawed to lyse the cells. Further cellular disruption was accomplished by gentle homogenization with a Teflon pestle in a glass tube at 5 strokes per minute for 2 minutes. The homogenate was made to 0.32M with sucrose, then centrifuged at 20,000×g for 40 minutes at 0°–4° C. The supernatant fluid, which contained cytosolic binding proteins for cyclosporine, was stored at −70° C. until needed.

Protein concentrations of the cytosol, as determined by using bicinchoninic acid protein assay reagent (Pierce, Rockford, Ill.), ranged from 2.1 to 4.2 mg/mL.

EXAMPLE 2

Competitive Protein Binding Assay for Cyclosporine Using the Cytosol From Example 1

1. Standard CsA solution

A 1.6 µg/mL standard was prepared by adding 0.1 mL of 160 µg/mL CsA stock solution in 70% aq. EtOH to 9.9 mL of whole blood, plasma or serum. The 1.6 µg/mL standard solution was doubly diluted in whole blood, plasma or serum to produce standards of 25, 50, 100, 200, 400, 800 and 1600 ng/mL. As controls, drug-free whole blood, plasma or serum were subjected to the same double dilutions.

2. Extraction of standards, controls or patient samples

Aliquots (50 µL) of CsA standards in whole blood, serum or plasma, controls, and patient samples were added to 950 µL of methanol, the capped tubes were mixed by vortexing for 30 seconds, and the mixture centrifuged at 2000×g for 5 minutes to remove precipitated proteins. Cyclosporine-free whole blood was extracted as above and used as the zero standard.

3. Assay procedures

Aliquots (50 µL to 850 µL of the ethanolic extracts of step 1 were added to glass test tubes, and the solvent removed at 40° C. under a gentle stream of $N_2$.

To the dried samples was added cytosolic binding protein (from Example 1) and the tube contents mixed by vortexing. An aliquot of an appropriate dilution of tracer $[^{125}I]$-CsA or $[^3H]$-dihydro CsA was added to each tube, and the solutions mixed by vortexing. The binding mixtures were incubated at 37° C. for 12 hours. Non-specific binding tubes (NSB) were prepared by adding CsA-free extract to a volume of buffer equal to the volume of the receptor aliquot.

After the incubation period, tubes were immersed in an ice-water bath and 3.0 mL of Tris-HCl buffer (pH 7.4, 4° C.) was added as a diluent. The contents of the tubes were then filtered through Whatman GF/B glass filters, and the filters washed once with 6.0 mL of ice-cold buffer. The filters were then sucked dry over a vacuum manifold.

When $^3H$ was the tracer, the filters were separately placed in LSC vials and an aliquot of PCSS added. The vials were vortexed, allowed to set for 2 hours, and the radioactivity quantified by LSS. When 125I was the tracer, the filters were separately placed in glass tubes, and the radioactivity quantified by a gamma counter. The times of counting were selected so as to accumulate statistically significant numbers of counts.

Standard curves were prepared by plotting $[B_{(std)}$-NSB/$B_{(O_{std})}$-NSB]100% against the concentrations of CsA in ng/mL.

Figure 1:
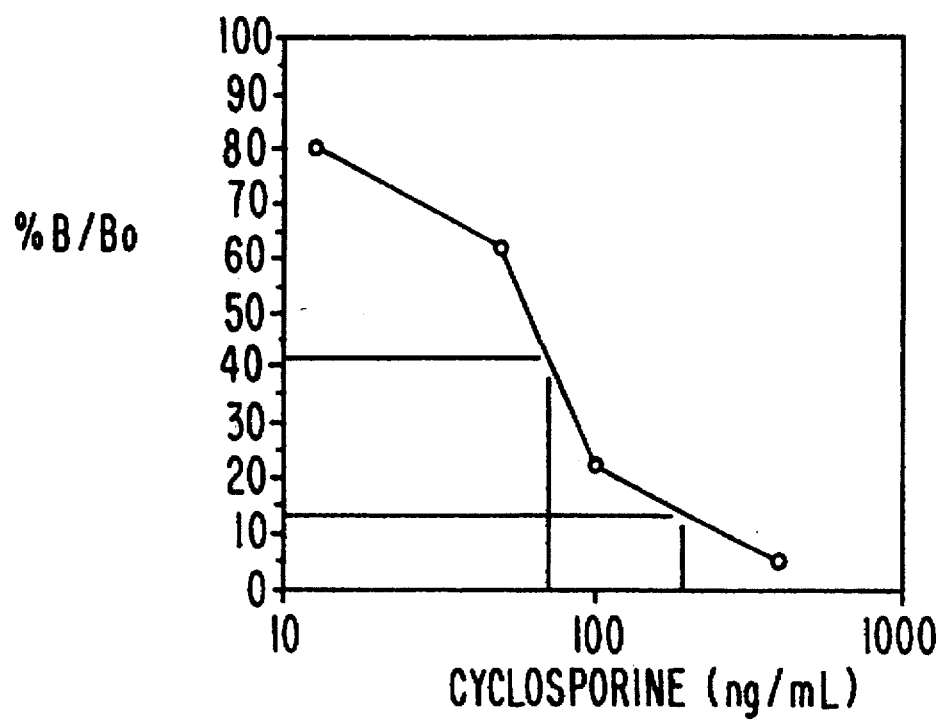
FIG. 1 shows a standard curve obtained from the competitive protein binding assay of the invention using [$^3$H]-dihydro CsA as the tracer and an extract (420 µg protein) of human mononuclear leukocytes as the cytosolic binding protein reagent.

The curve of FIG. 1 was generated by a competitive protein binding assay at a fixed concentration of cytosolic receptor protein and $[^3H]$-dihydro CsA, and doubling concentrations of CsA. The standard curve was useful between about 10 ng/mL and 400 ng/mL of the cyclosporine.

Figure 2:
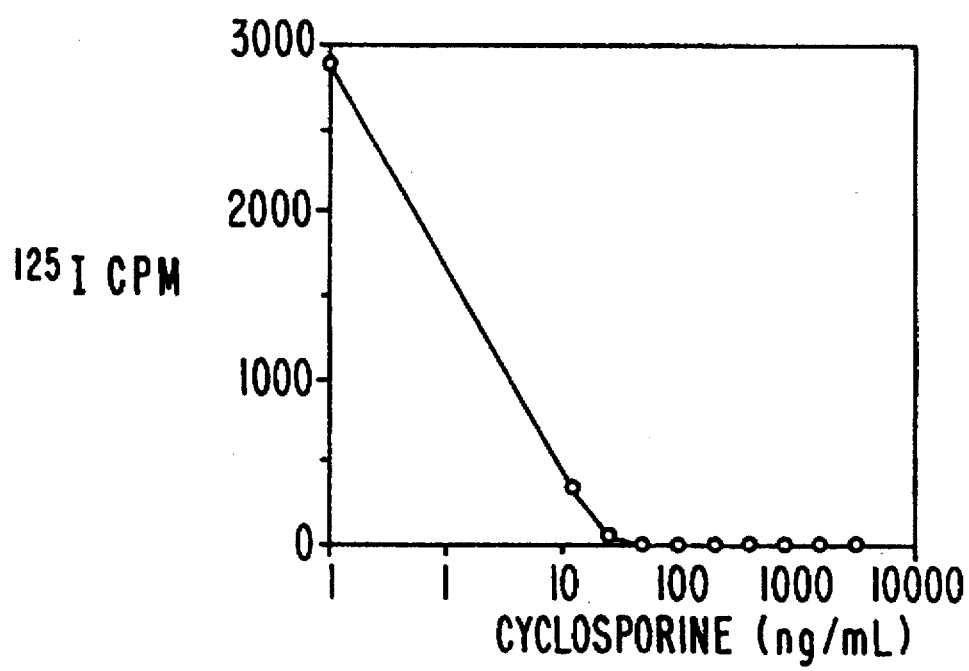
FIG. 2 is the same as FIG. 1, but using [$^{125}$I]-CsA as the tracer.

The curve of FIG. 2 was generated by a competitive protein binding assay carried out in the same manner as that from which FIG. 1 was generated, but using 125I as the tracer and plotting bound radioactivity against concentration. The CsA standard which represented 12 ng/mL in whole blood had a bound value of 12%. The CsA standard which represented 25 ng/mL in whole blood had a bound value of 2%. The striking difference between FIG. 1 and 2 indicates a greater affinity to the receptor sites for the $^{125}$I-CsA compared to [$^3$H]-dihydro CsA, and a consequently greater sensitivity. Concentrations of cyclosporine activity in whole blood equivalent to as little as about 5 ng/mL CsA can be quantified by this method when using the $^{125}$I tracer.

EXAMPLE 3

Competitive Protein Binding Assay for CyclosPorine

The following assay was performed as in Example 2, but using the modifications described herein below.

The volume of CsA methanolic extract of standards controls and patient samples was 800 μL. The volume of cytosolic binding protein was 200 μL of a 1:5 (v/v) dilution in buffer (0.6 mg/mL). The radioligand was [$^3$H]-dihydro CsA (25 μL). The incubation period was 12 hours. The reaction was stopped by adding 2 mL of ice-cold buffer to each reaction tube, and tubes were maintained in an ice bath for 5 minutes. Protein-bound [$^3$H]-dihydro CsA was separated from the free ligand by the glass filter method. Filters were counted in 10 mL of PCSS scintillant, and a standard curve was prepared as previously described for $^3$H tracers.

Figure 3:
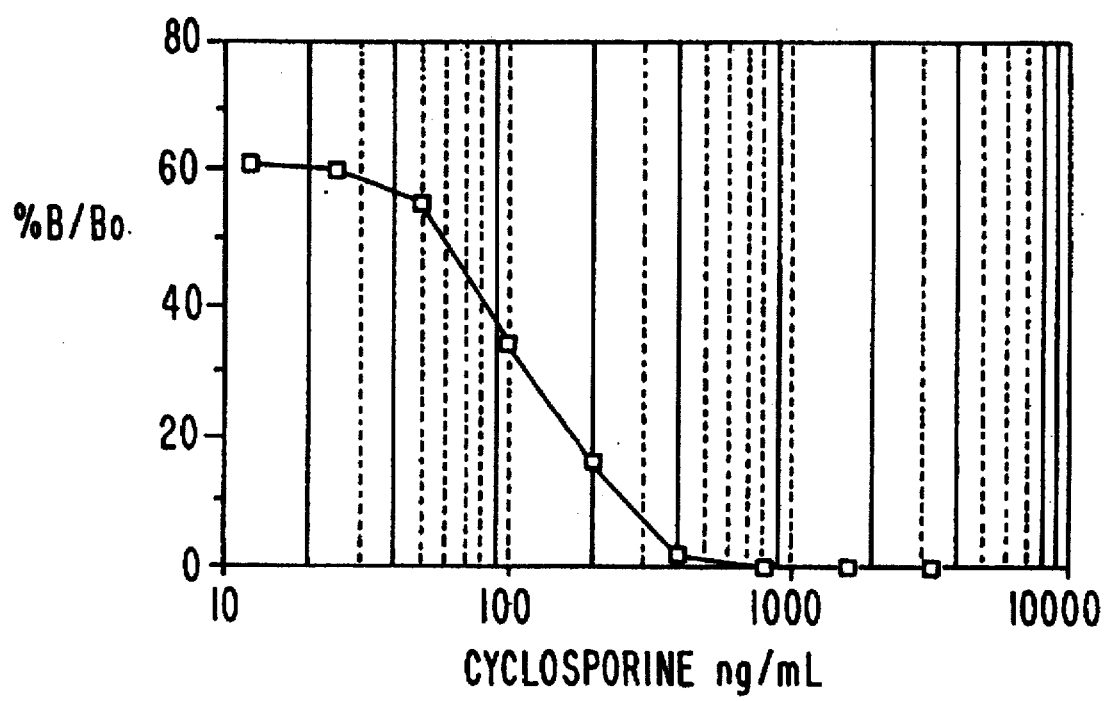
FIG. 3 is the same as FIG. 1, but using 120 µg of cytosolic binding protein.

As shown in FIG. 3, a classical sigmoid relationship was obtained when % $B/B_o$, was plotted against the log of CsA in ng/mL. This is within the range of cyclosporine concentration in patients as determined by radioimmunoassay (Mahoney, W. C., U.S. Pat. No. 4,727,035).

EXAMPLE 4

Fractionation of Human Mononuclear Leucocyte Cytosolic Proteins

Figure 4:
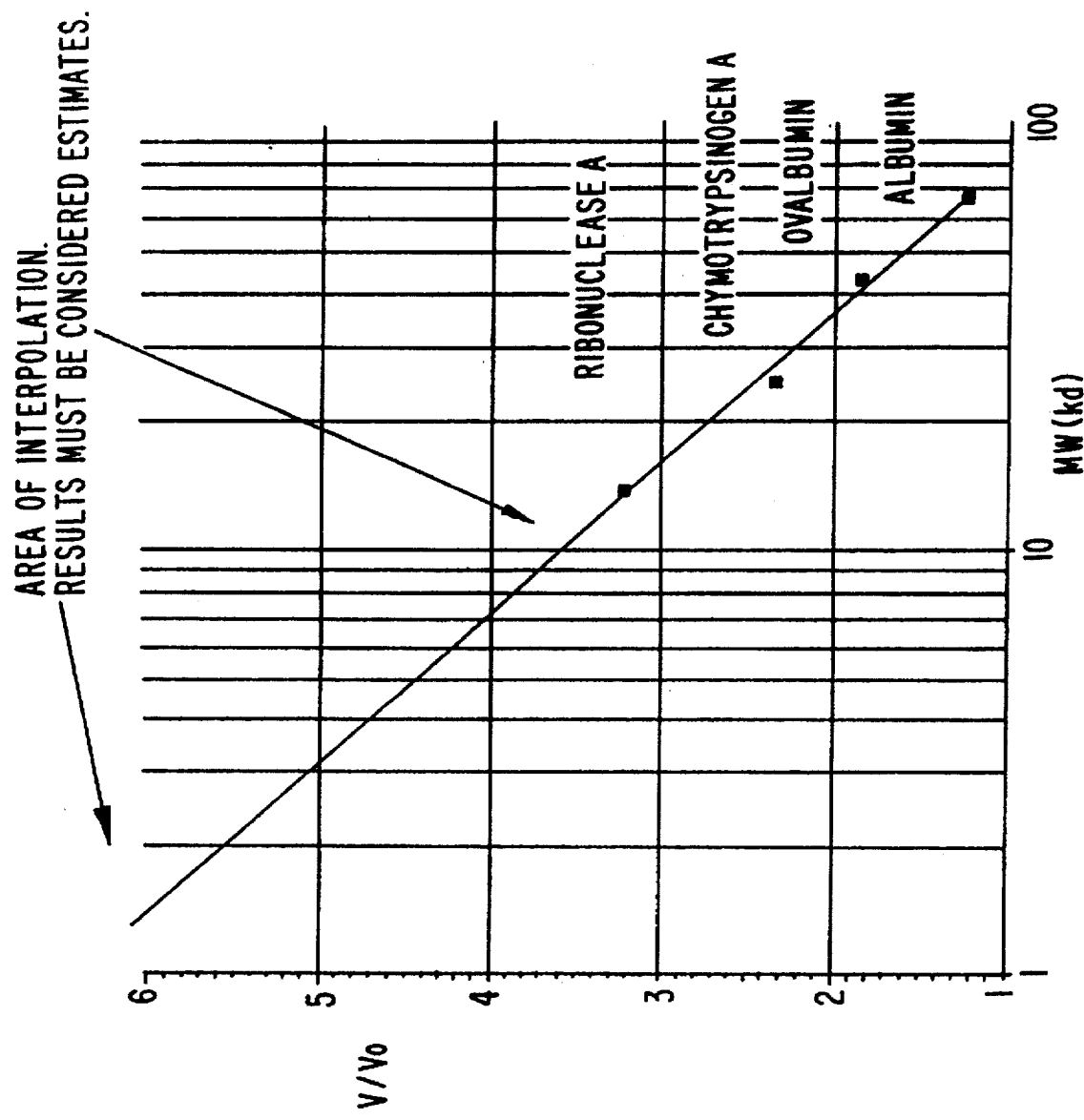
FIG. 4 shows the calibration of a Bio-Gel P-100 molecular sieve column with molecular weight markers.

A 1 m×2 cm I.D. column of Bio-Rad's Bio-Gel P-100 molecular weight exclusion gel (fractionation range approximately 5,000–100,000 dal.) was equilibrated with 50 mM Tris. HCl buffer, pH 7.4, with 0.4 mM $CaCl_2$, 0.5 mM EDTA and 80 mM NaCl for 24 hours. The column was standardized (FIG. 4) using Pharmacia's molecular weight standards ranging between 15,000 and 66,000 dal.

A 2 mL aliquot (2.2 mg protein) of the cytosol from Example 1 was passed through the column and fractionated with the aforementioned column buffer. Fractions (4 mL.) were collected using an ISCO (Lincoln, Nebr.) fraction collector. Samples were assayed for protein by monitoring A280 nm. Sixteen pools of the 4 mL fractions were lyophilized, and then reconstituted in 2 mL. of deionized water, except for fraction 7 which was reconstituted with 15 mL. of water to facilitate dissolution.

Binding assays on each fraction were carried out as follows. To 0.5 mL of each fraction (Tube no. 1) was added 25 μL of [$^3$H]-dihydrocyclosporine. To an identical sample (Tube no. 2) was added the same amount of tracer, plus 64 ng of unlabeled cyclosporine. After incubating the binding mixtures for 12 hours at 37° C., bound and free tracers were separated by the procedure described in Example 2. Specific binding was calculated as described above for both samples.

Figure 5:
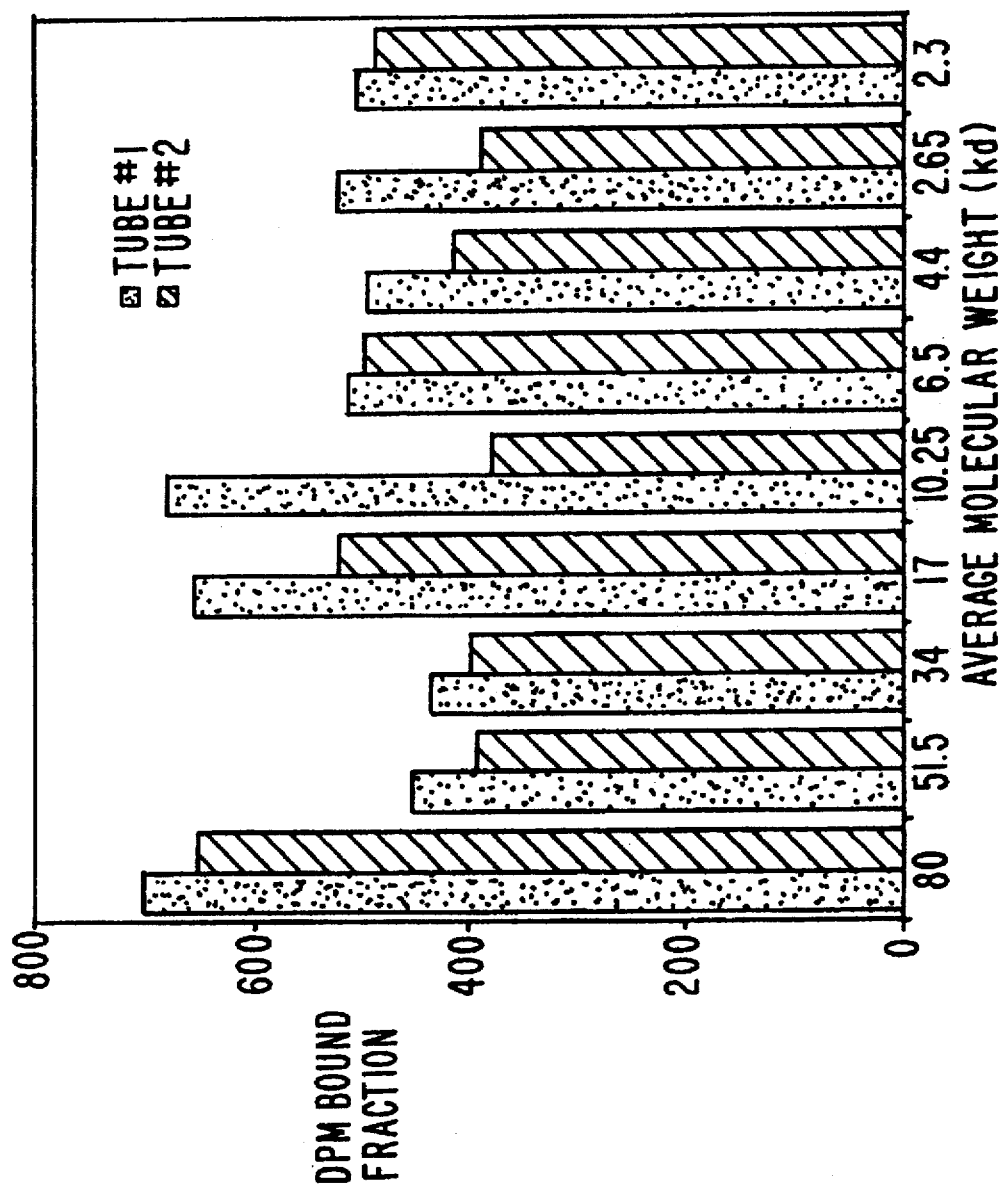
FIG. 5 shows the results of the application of the competitive protein binding assay of the invention to cytosolic protein fractions eluting from a Bio-Gel P-100 column.

In the histogram of FIG. 5 (Graph A) is plotted the amount of radioactive [$^3$H]-dihydrocyclosporine bound to protein, in the absence (Tube no. 1) and presence (Tube no. 2) of competing unlabeled cyclosporine as a function of the average molecular weight of each of the column fractions. The differences between Tubes 1 and 2, which reflect binding competition, for each column fraction are plotted as a function of the average molecular weight of each column fraction in FIG. 6. It is clear that a cytosolic fraction representing one or more proteins of range average molecular weight of approximately 10,250 dal. was most active in the competitive protein binding assay of the invention, and that the 17 kDa. and 2.65 kDa fractions also exhibited acceptable competitive CsA binding activity.

EXAMPLE 5

Analysis of CyclosPorine in Patient Blood Samples: Comparison of Competitive Protein Binding Assay with HPLC Analysis Sixteen blood samples from transplantation patients receiving CsA were analyzed in duplicate by a competitive protein binding assay carried out in accordance with this invention and by an HPLC procedure.

For the binding assay, the procedures of Example 3 were followed, using [$^3$H]-dihydrocyclosporine as the tracer, but using a 1.5 hr. incubation period.

HPLC analysis was carried out according to the procedure of Giesbrecht et al., Therap. Drug Monitoring, in press 1988]. Briefly, a protein-free filtrate of patient blood was prepared by extracting 250 μL of whole blood with 750 μL of acetonitrile:methanol (9:1) containing the internal standard CsD. After centrifuging the mixture, the supernatant fluid was passed through cartridges of C18 and Silica Bond Elut to remove impurities. Eluates were dried, reconstituted in acetonitrile:water (1:1), then extracted with haptene to remove late-eluting peaks. HPLC was performed at 75° C. using a Supelcosil C18 column (10 cm×4.6 mm) with 3 μpacking (Supelco, Inc.) using a Waters Scientific Co. HPLC system. The mobile phase of acetonitrile: phosphate buffer, pH 2.5 (77:23) was run at a flow rate of 0.6 mL/min. Absorbency of the eluted fractions was estimated at 214 nm. Recovery for CsA was 92–104%, at a lower sensitivity of 15 μg/L. The method was linear to 500 μg CsA/L. Peak height measurements were compared to CsA external standards of 150 and 400 μ/g/L.

Figure 7:
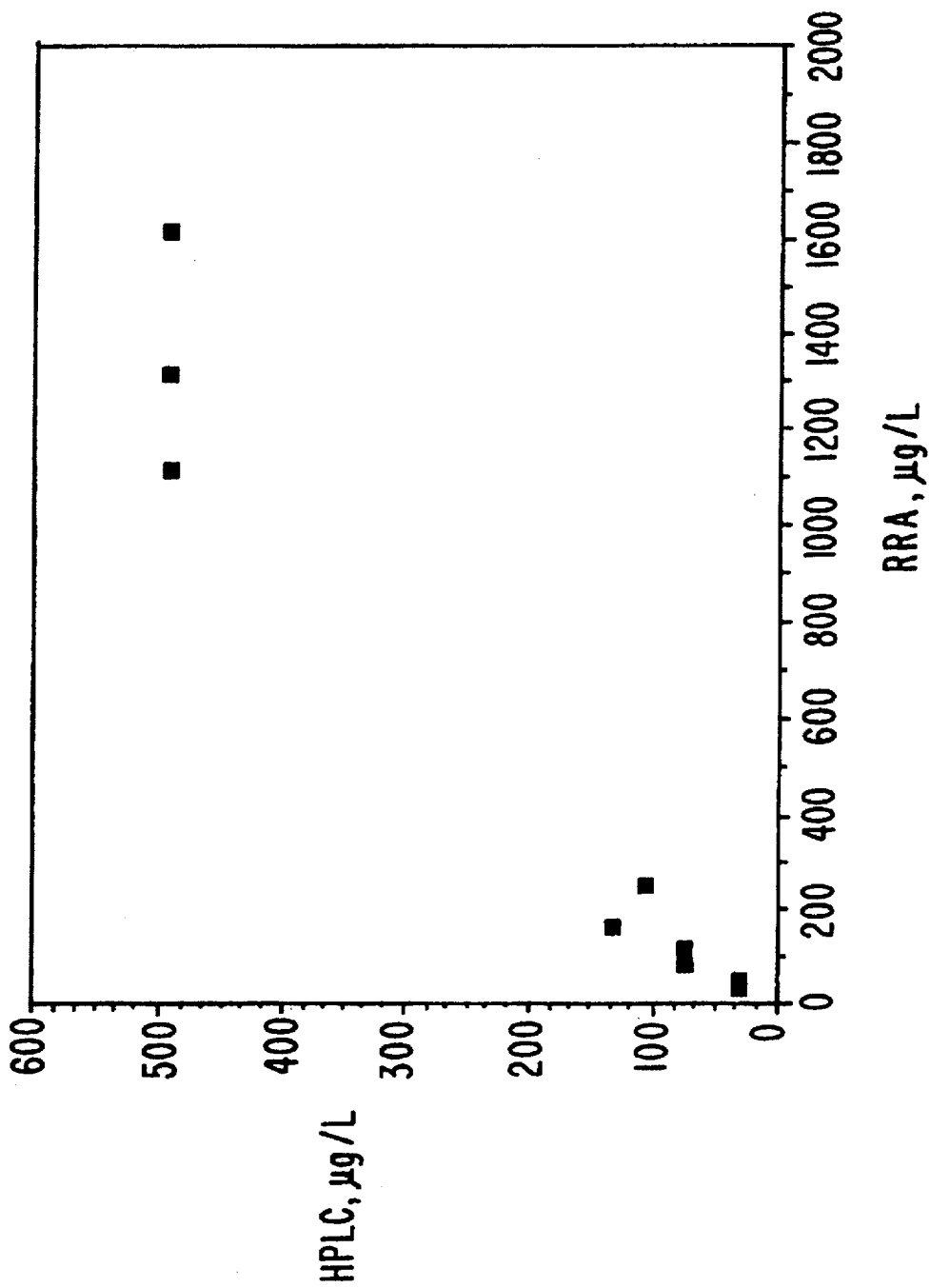
FIG. 7 shows a comparison of the results of analyzing human patient blood for cyclosporines by HPLC with a binding assay carried out in accordance with the invention.

The results are shown in FIG. 7, wherein the results of HPLC assays for CsA (in μg/L) are plotted against the result for the same sample obtained by the competitive protein binding assay of the invention (RRA, μg/L). Different scales were required as HPLC yielded values substantially lower than did the RRA. For example, patient samples that were approximately 500 μg/L by HPLC ranged from 1100 to 1600 μg/L by the RRA. Such results indicate that the RRA estimated not only the parent CsA, but immunophilin-binding metabolites as well. The fact that these metabolites reacted with an immunophilin suggests that the former molecules are biologically active, and suggests further that the binding assay of the invention is capable of estimating all pharmacologically active species of cyclosporine.

EXAMPLE 6

Fractionation of Human Transformed T-helper Lymphocytes (CEM) Cytosol by HPLC The CEM cell line was obtained from Dr. Maria Chan, Director of Immunology, Department of Laboratory Medicine, Children's Hospital, Washington, D.C. 20010.

Figure 8:
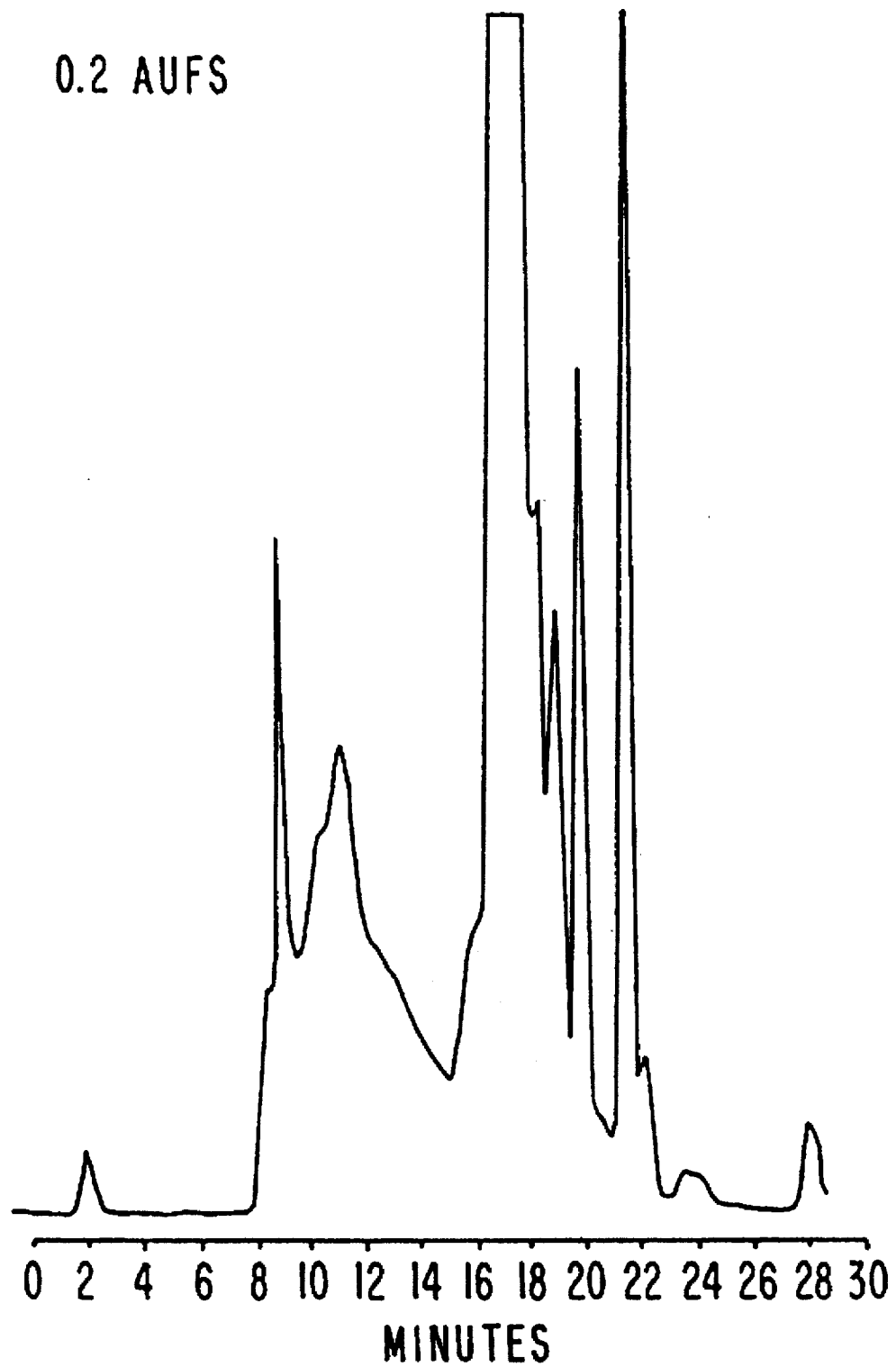
FIG. 8 shows the protein elution profile of CEM lymphocyte cytosol chromatographed on a Bio-Sil 125 column.

CEM cells were disrupted, and the cytosol isolated, as described in Example 1. The CEM cytosol was then fractionated by HPLC on a column of Bio-Sil 125 in phosphate-buffered saline, pH 6.8, at a rate of 1.0 mL/min. Eluted protein was monitored by $A_{280nm}$; the protein fractionation profile is shown in FIG. 8.

Figure 9:
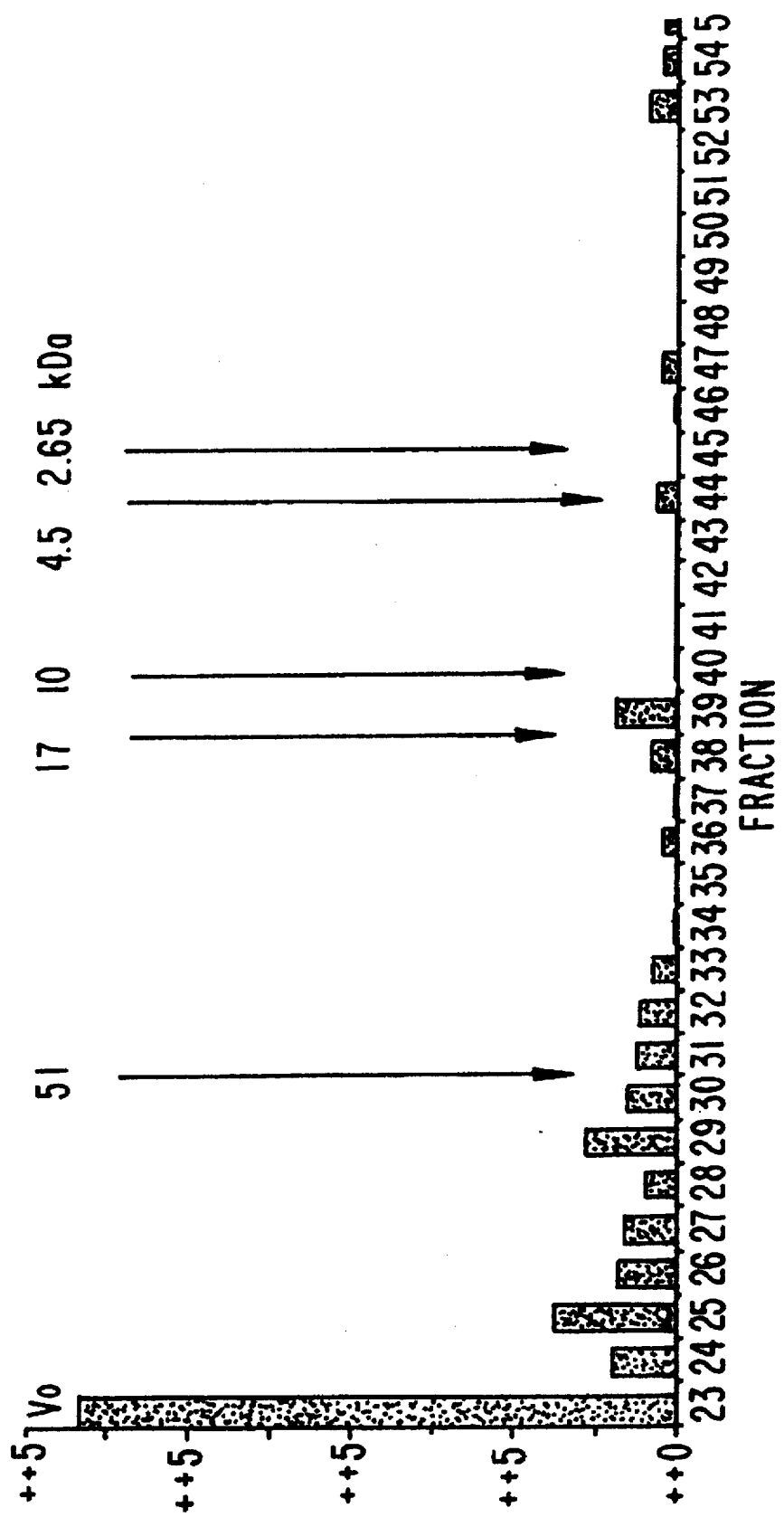
FIG. 9 shows the CsA binding specific activities of the column fractions from FIG. 8.

Each CEM cytosol fraction was tested for CsA binding specific activity as in Example 5; the binding data are shown in the histogram of FIG. 9. Major specific binding was found at molecular mass ranges of about 43–64 kDa, 10–17 kDa and about 4.5 kDa.

The 43–64 kDa fractions were combined and analyzed by SDS-PAGE (Laemlli 10% polyacrylamide gel, no reducing agent) and proteins visualized with Bio-Rad's silver stain. As shown in Table 1, only 3 peptides were present. When the electrophoresis was run on 20% polyacrylamide with β-mercaptoethanol as reducing agent (which splits peptide subunits linked by disulfide bonds), four peptides were observed within the range 43–64 kDa range.

TABLE 1

Peptide Bands from SDS-PAGE of 43–64 kDa Protein Fraction*

| 10% gel, no reducing agent | | 20% gel, 2-ME | |
|---|---|---|---|
| Rf | kDa | Rf | kDa |
| 0.15 | 71.9 | 0.07 | 57.5 |
| 0.19 | 62.3 | 0.11 | 51.0 |
| 0.24 | 52.2 | 0.14 | 46.6 |
| 0.26 | 48.6 | 0.16 | 43.9 |
| 0.46 | 23.9 | 0.20 | 38.9 |
| 0.48 | 22.3 | 0.23 | 35.6 |
| 0.51 | 20.0 | 0.25 | 33.5 |
| 0.62 | 13.5 | 0.29 | 29.7 |
| 0.65 | 12.2 | 0.31 | 28.0 |
| | | 0.34 | 25.6 |
| | | 0.37 | 23.4 |
| | | 0.39 | 22.0 |
| | | 0.41 | 20.7 |
| | | 0.43 | 19.5 |
| | | 0.46 | 17.8 |
| | | 0.49 | 16.3 |
| | | 0.51 | 15.3 |
| | | 0.61 | 11.4 |
| | | 0.62 | 9.8 |

*11.3 μg protein applied to a lane

EXAMPLE 7

Cyclosporine Binding Proteins of JURKAT Lymphocytes

JURKAT lymphocytes, a IL-2 producing cell line, was obtained from Dr. Maria Chan, Director of Immunology, Department of Laboratory Medicine, Children's Hospital, Washington, D.C. 20010. A JURKAT cytosol was prepared from these cells as in Example 1. A sample of cytosol was equilibrated with 56 pmol of $^3$H-CSA, then chromatographed on a Bio-Sil 125 column at 1.0 mL/min. Fractions (0.425 ml) were collected and counted in Packard Gold scintillation fluid.

Figure 10:
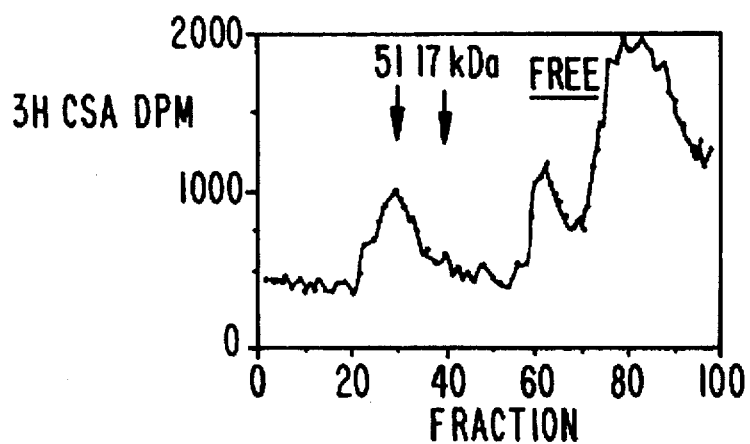
FIG. 10 shows a direct binding profile of $^3$H-CsA in protein fractions of a cytosol from JURKAT cells.

The direct binding profile is shown in FIG. 10. The major CsA binding protein was located at a range average molecular mass of about 51.5 kDa. Relatively minor binding was exhibited at about 17 kDa (shoulder on 51.5 kDa peak). Another binding activity was observed in the molecular mass range of about 2.4–3.0 kDa.

EXAMPLE 8

Comparison of Five Different Assays for Cyclosporine

Whole blood specimens from the clinical laboratory were analyzed for cyclosporine and metabolites according to the competitive protein binding method of the invention and compared against an HPLC method (Giesbrecht et al., supra), Sandoz SANDIMMUNE® specific and non-specific mAb RIA (Sandoz Pharmaceuticals, Hanover, N.J.), CYCLOTRAC® RIA (Incstar, Stillwater, Minn.), and Abbott TDx® Fluorescence Polarization Immunoassay (Abbott Labs., Chicago, Ill.).

TABLE 2

Regression Analysis and Correlation of Whole Blood CsA Concentrations From Five Competitive Assays Compared With HPLC

| Assay | Slope | Correlation Coefficient Intercept | Sample Size (r) | (n) |
|---|---|---|---|---|
| Incstar | 1.08 | −35.70 | 0.96 | 31 |
| Abbott TDx$^R$ | 1.79 | +98.27 | 0.83 | 31 |
| Sandoz Specific | 1.17 | −43.45 | 0.89 | 22 |
| Sandoz Nonspecific | 2.75 | +204.57 | 0.71 | 31 |
| RRA | 1.09 | +365.67 | 0.12 | 26 |

Comparing the results from the two nonspecific assays and RRA yields two regression lines: RRA=0.309 Sandoz SANDIMMUNE® Non-specific mAb+336.33(r=0.46, n=25), and CPA=0.62 Abbott TDx=311.27 (r=0.47, n=25).

Overall, CPA results tended to produce higher results than obtained by Abbott TDx, likely because the former also estimates biologically active CsA metabolites. CPA results tended to produce lower results than obtained by the Sandoz SANDIMMUNE Nonspecific Mab assay, likely because the former is more specific.

The ratio of mean cyclosporine concentrations from the five competitive assays compared to HPLC were 0.86 15(Incstar), 0.99 (Sandoz Specific), 3.93 (Sandoz non-specific), 2.36 (Abbott TDx) and 3.02 (CBA). Sandoz non-specific maA had a higher cross-reactivity to CsA metabolites than did Abbott TDx. The mean ratio of the CBPA results lies between the two nonspecific assays. This further illustrates the lack of correlation of nonspecific measurements to the cytosolic binding proteins.

The low correlation coefficient of the CBA method according to this invention compared to the other methods currently in use suggests strongly that the present method is measuring both the parent cyclosporine and its biologically-active metabolites, rather than merely parent cyclosporine or immunologically active, but not necessarily biologically-active, metabolites.

EXAMPLE 9

Binding of CsA to CEM Binding Proteins

CEM cytosol, prepared as in Example 1, was fractionated on a Bio-Rad TSK SEC-125 HPLC column at a flow rate of 1 mL/min. of 20 mM sodium phosphate buffer, pH 6.8. The column had previously been standardized with molecular weight markers. Samples to be separated were filtered and injected using either a 250 μL or 500 μL loop, and a Beckman HPLC instrument.

Figure 11:
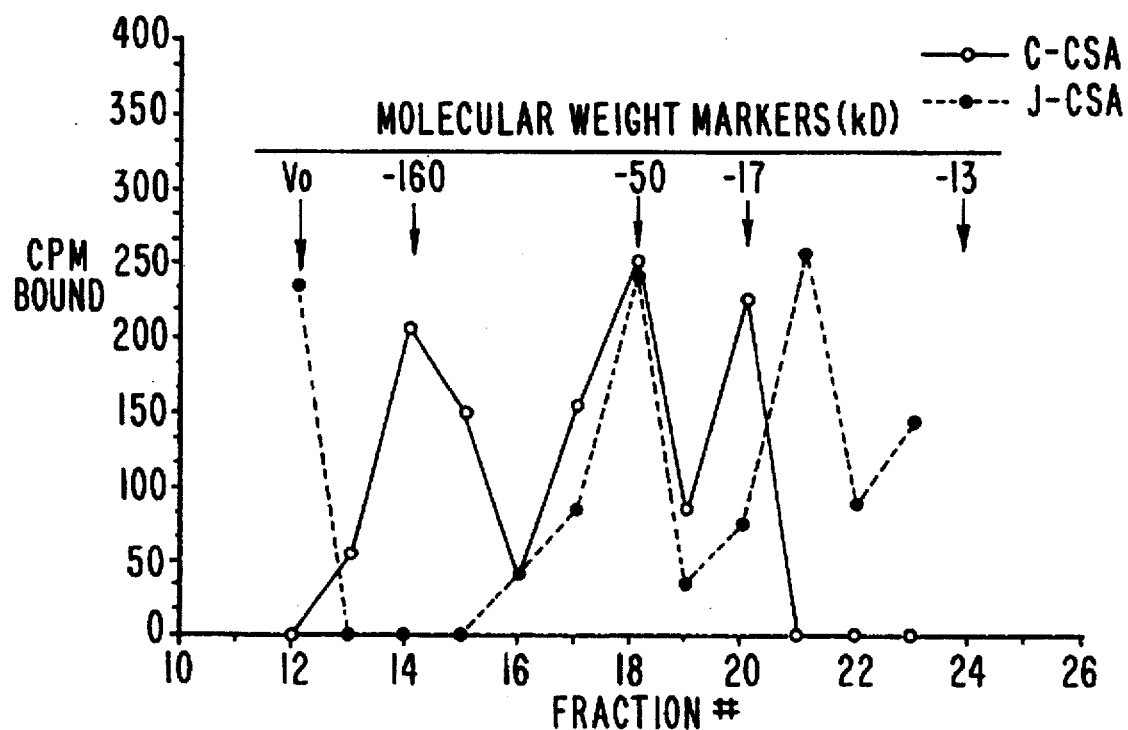
FIG. 11 shows CsA binding proteins in protein fractions derived from a CEM cell cytosol (C-CsA) and JURKAT cell cytosol (J-CsA).

Collected column fractions were assayed for binding to $^3$H-CSA (shown as C-CSA in FIG. 11). CsA was found to bind proteins in three regions, i.e., in regions wherein peak binding was to proteins with range average molecular mass of about 160 kDa, 51.5 kDa and 17 kDa, (FIG. 11).

The contents of the tubes representing the three binding regions from FIG. 11 were pooled, concentrated in a rotary evaporator, and reassayed for binding of $^3$H-CsA. The results appear in Table 3.

TABLE 3

| Binding of ³H-CsA State of Purification | cpm/µg protein |
| --- | --- |
| Crude cytosol | 36 |
| Fractionated and concentrated | |
| I (160 kDa average region) | 371 |
| II (51.5 kDa average region) | 670 |
| III (17 kDa average region) | 3430 |

The specific binding activity of CsA was enriched in I by 10-fold, in II by 20-fold, in III by 100-fold, compared to the crude cytosol.

EXAMPLE 10

Binding of CsA to Proteins Derived from Jurkat Cell Cytosol

A Jurkat cell cytosol, prepared as in Example 7, was fractionated on a calibrated TSK SEC-125 column as in Example 9. Protein fractions were assayed for binding to ³H-CSA (shown as J-CsA in FIG. 11).

CsA bound primarily to proteins in only two regions, namely, range average molecular masses of the 51.5 kDa and 17 kDa regions; binding to a protein in the 160 kDa region, as was observed with CEM cells (cf., FIG. 11), was not present in Jurkat cell extracts.

EXAMPLE 11

Purification of 50–54 kDa Immunophilin To Homogeneity from Human Spleen

The binding protein referred to above in Examples 4, 6, 7, 9 and 10 as the binding protein of range average molecular mass of about 51.5 kDa (actual range by chromatographic methods, 43–64 kDa) was purified to homogeneity from human spleen as follows.

Human spleen tissue (180 g) was homogenized at 4° C. in 4 volumes of ice-cold homogenization buffer ("HB", 5 mM sodium phosphate buffer, pH 6.8, containing 1 mM PMSF, 10 mM EDTA, 10 mM EGTA, and 5 mM β-mercaptoethanol) using first a Polytron tissue disrupter at high speed, then a Teflon/glass homogenizer. Cellular debris was removed by centrifugation at 4,000×g at 4° C. The pellet was resuspended in HB, and centrifuged as above. Pooled supernatant fluids were centrifuged for 1 hour at 100,000×g at 40° C. to produce a cytosol supernatant fluid ("S100" fraction).

The S100 fraction was fractionated by isoelectric focusing at 40° C. using a RotoforTM (Bio-Rad, Richmond, Calif.) which contained a prefocused solution of ampholytes (0.73% solids/vol. of pH 4–6, PH 6–8, and 0.37% solids/vol. of pH 8–10; total vol. 50 mL). The cathode contained 0.1M H₃PO₄ and the anode 0.1M HCl. Constant power (12 w) was supplied by a Pharmacia 3000/150 power supply (Pharmacia, Piscataway, N.J.). The unit was electrofocused until constant voltage (450 V) was achieved. S100 was separated into 20 fractions, which were immediately measured for pH and specific binding to 3H-CsA and 3H-dihydro FK506 using the LH-20 assay described above.

Fractions between pH 5 and 7 were collected and concentrated using 10 kDa Centriprep filtration units. Concentrates were passed through a gel permeation BioSil-125 HPLC column at a flow rate of 1.0 mL/min. in 10 mM phosphate buffer, pH 6.8. Fractions binding to ³H-CSA or ³H-dihydro-FK-506 (tritiation by Amersham Corp., Arlington, Ill., of native FK-506 obtained from Fujisawa Pharmaceutical Co., Osaka, Japan) or both were passed through a weak cation exchange CM 250×4.6mm cartridge (Altech, Lansing, Mich.) preequilibrated with 5 mM potassium phosphate buffer, pH 6.8, under the following conditions: 5 minutes at 5 mM buffer, 5 mM to 200 mM buffer over 15 minutes, 200 mM buffer for 5 minutes, and 200 mM to 500 mM buffer over 15 minutes, at a flow rate of 0.5 mL/minute. The binding fraction, i.e., a single peak at 200 mM buffer, was obtained.

Figure 12:
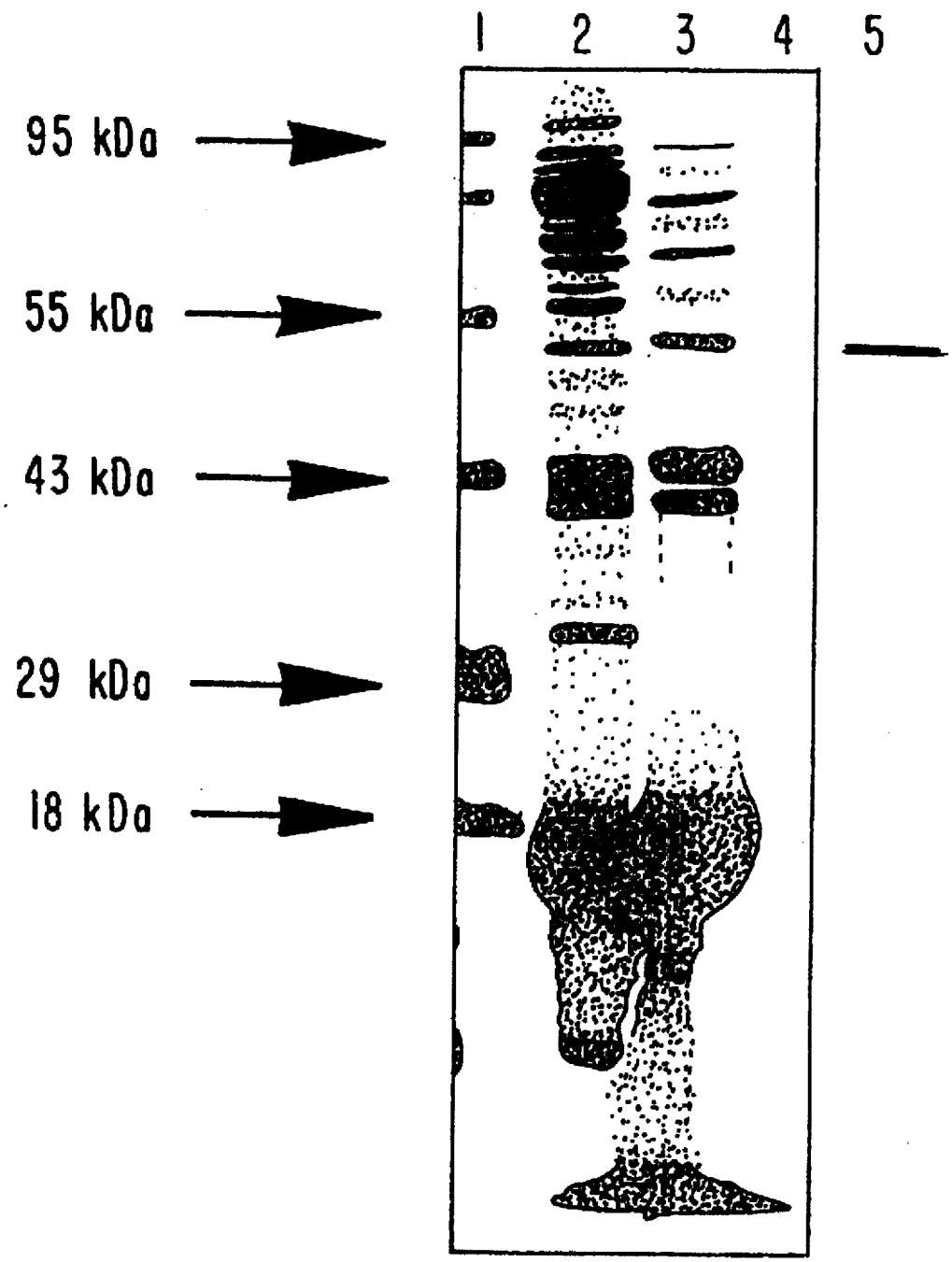
FIG. 12 shows the SDS-PAGE patterns of the human spleen cytosolic 50–54 kDa immunophilin at various stages of purification.

SDS-PAGE was performed on material from this peak according to Laemmli, Nature, 227:680–5 (1970); the separation pattern is shown in FIG. 12. In FIG. 12, Lane 1 consists of molecular weight markers (17 to 95 kDa); Lane 2 is the S100 cytosol; Lane 3 is the isoelectric focusing fraction; Lane 4 is the gel permeation fraction, and Lane 5 is the weak cation exchange fraction. Homogeneity of the Lane 5 binding protein was confirmed by 2-D electrophoresis.

Data on the purification of the 50–54 kDa binding protein is shown in Table 4. In a 4-step process, the protein was purified upwards of 8700 fold, and the final protein appeared homogeneous by-SDS-PAGE.

TABLE 4

| Step | Total Protein (mg) | Total volume (mL) | Binding (DPM/mg) | Purif. (fold) | Yield (%) |
| --- | --- | --- | --- | --- | --- |
| S100 | 2195 | 35 | 477 | 1 | 100 |
| Rotofor (6.3–6.6) | 721 | 10 | 1143 | 2.4 | 32.8 |
| BioSil-125 | 2.4 | 4 | 82,367 | 173 | 0.11 |
| CM 100/500 mM phosphate | 0.14 | 4 | 4,153,015 | 8,707 | 0.006 |

Remarkable purification was unexpectedly obtained in the final, cation exchange step.

EXAMPLE 12

Purification of a 50–54 kDa Immunophilin Protein from JURKAT Cells

The binding protein referred to above in Examples 4, 6, 7, 9 and 10 as the binding protein of average molecular mass of about 51.5 kDa (peak elution range 42–64 kDa) protein was purified further from JURKAT cells as follows.

JURKAT T-cell leukemia cells ($1.5 \times 10^9$) were cultured in complete media (CM) containing RPMI 1640 commercial medium supplemented with L-glutamine, 50 U/ml penicillin, 50 µg/ml streptomycin, and 2–10% fetal calf serum (FCS, MA Bioproducts, Walkersville, Md., or GIBCO-BRL, Gaithersburg, Md.) and insulin, transferrin, sodium selenate extender (Boehringer Mannheim, Indianapolis, Ind.) at 37° C. in 5% $CO_2$.

Cells were harvested weekly, and the S100 cytosol fraction was produced by pelleting the cells at low speed centrifugation, washing cells with RPMI 1640, washing cells with 10 mM phosphate buffer, pH 6.8, containing 1 mM PMSF (Sigma Chem., St. Louis, Mo.); disrupting cells by 4 rapid freeze-thaw cycles at −80° C. and 40° C., respectively; homogenizing the disrupted cells with a Teflon/glass homogenizer at high speed; and, centrifuging the homogenate for 1 hour at 100,000×g at 40° C. to produce the S100 supernatant fluid.

S100 (from $14 \times 10^9$ cells, 10 mL) was centrifuged (2500× g) for 1 hour at 4° C. in a 30 kDa cutoff Centriprep™ concentrator. The resulting concentrate (1 mL) was diluted with 15 mL of 10 mM phosphate buffer, pH 6.8, and centrifuged through the concentrator until the volume was reduced to 5 mL. This step facilitated the removal of a significant portion of the 17 kDa and 10–12 kDa binding proteins from S100.

The product (protein molecular mass>30 kDa) was separated by isoelectric focusing as described in Example 11. The fraction (pH 6–6.8) which demonstrated binding to both $^3$H-CSA and $^3$H-dihydro-FK-506 was then refocused under the same conditions using only the ampholytes contained in the 2.7 mL fraction (diluted to 55 mL with deionized water); focusing was complete when a constant voltage of 2200 V was achieved.

The 20 fractions obtained by focusing were screened for competitive binding to CsA and to FK506 by the LH-20 binding assay described above. At pH 6.29, binding of [$^3$H]-CSA was inhibited by FK-506. This fraction (3.02 mg in 2.7 mL) was then passed through a BioSil-125 HPLC column at a flow rate of 1.0 mL/minute of 10 mM phosphate buffer, pH 6.8. Those fractions around the expected molecular weight (around 50 kDa) were tested for binding to [$^3$H] CsA and [$^3$H-dihydro]FK-506 as described above.

Binding fractions were pooled, then passed through a Beckman TSK CM-2SW Spherogel weak cation exchange HPLC column (26×4.6 mm) at a flow rate of 0.5 mL/minute of 10 mM phosphate buffer, pH 7.2. Fractions containing the 50–54 kDa binding protein were pooled and used for binding assays.

Figure 13A:
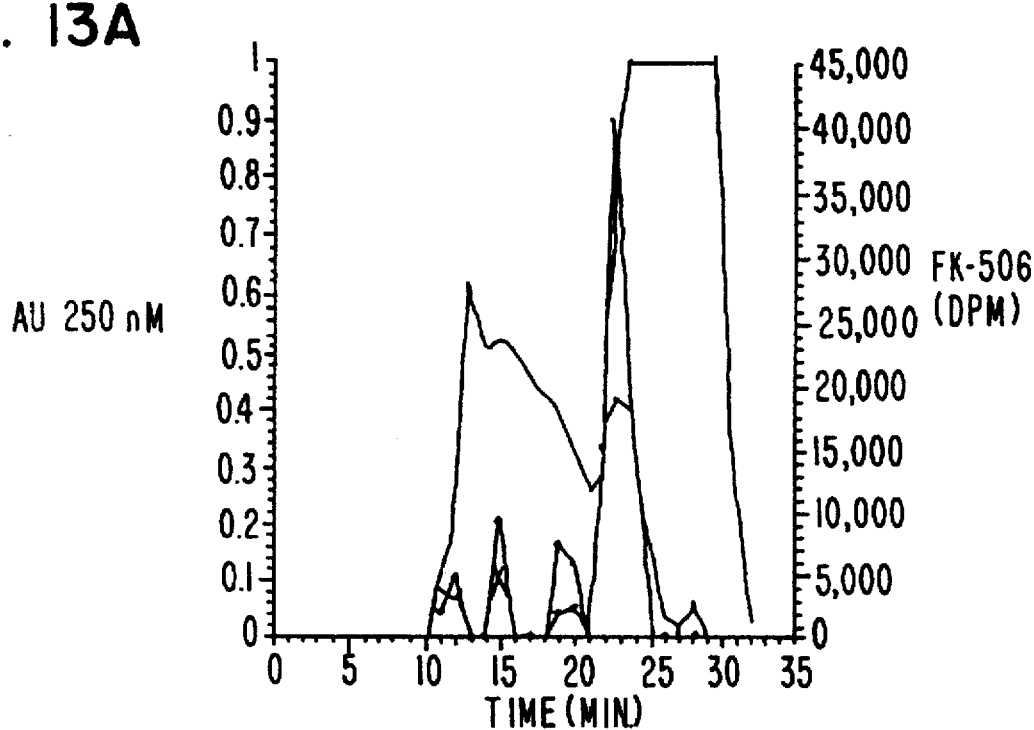
FIGS. 13(a-c) show specific binding to a purified JURKAT cell 50–54 kDa immunophilin of CsA (A), FK-506 (B) and rapamycin (C).
Figure 13B:
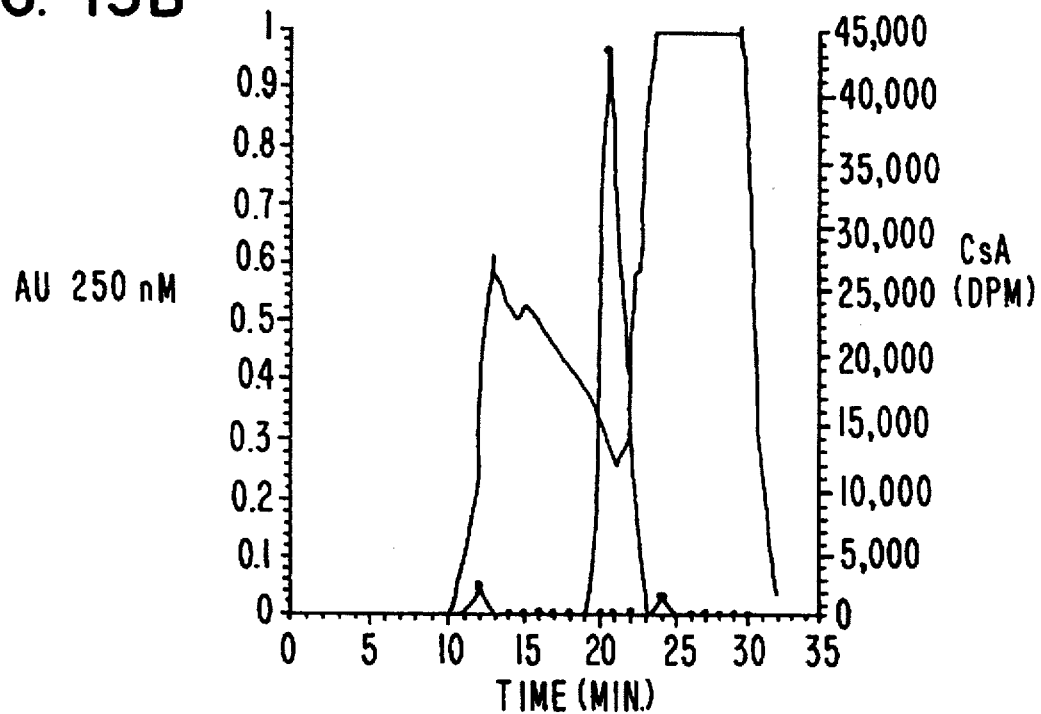
Figure 13C:
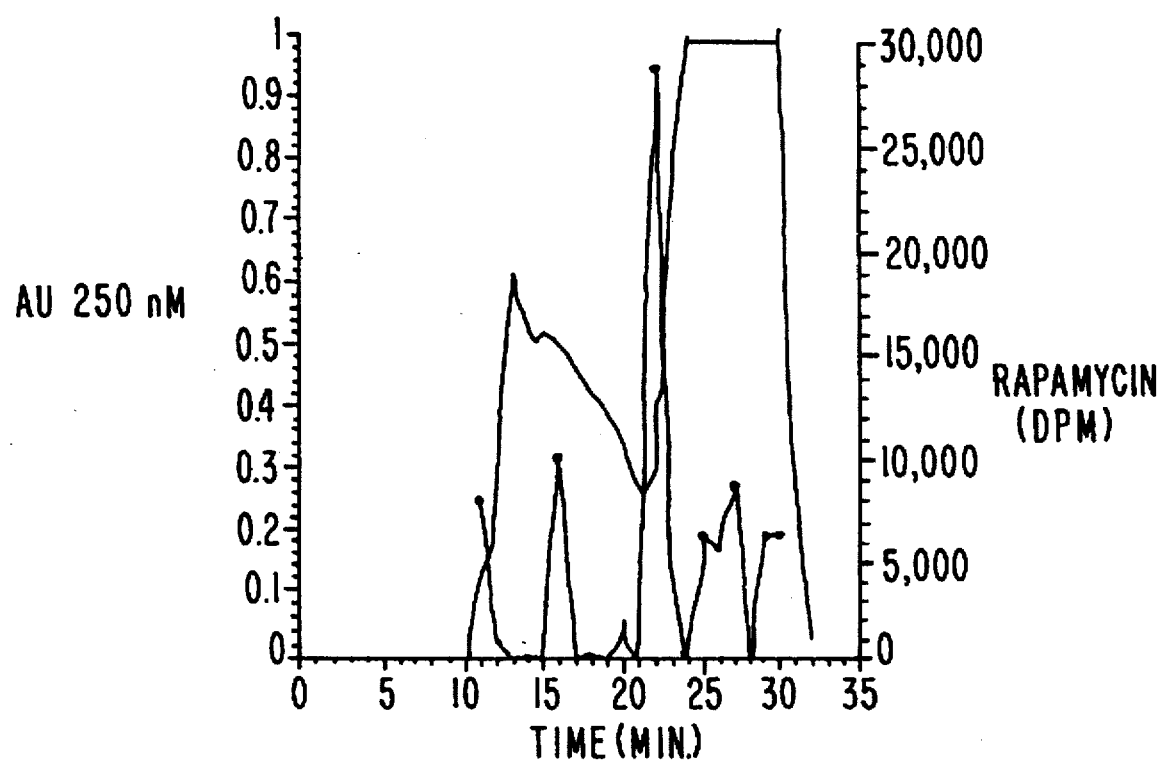

Purified 50–54 kDa binding protein was incubated for 15 minutes at 25° C. with varying concentrations of the FK-506 or rapamycin and either 1.8 pmol of [$^3$H-dihydro]-FK-506 or 2.25 pmol of [$^3$H]-CSA in 20 mM Tris buffer, pH 7.4, containing 5 mM β-mercaptoethanol. Bound and free ligand were separated using the above-described LH-20 system. CsA, FK-506 and rapamycin all bound to this protein. (FIG. 13 A-C). Although the major (in terms of abundance) binding protein for FK-506 was found in the 10–12 kDa fraction (referred to in Example 4 above as the binding protein of range average molecular mass of 10.25 kDa), specific binding was also detected in several other proteins, including proteins of about 50–54 kDa, about 80–100 kDa, as well as proteins of even greater mass (greater than about 120 kDa) (FIG. 13 A). Rapamycin (0.7 mM) inhibited the binding of [$^3$H-dihydro]-FK-506 in all fractions. Although the major (in terms of abundance) specific binding protein for CsA was found in the 16–18 kDa fraction (referred to in Examples 4, 5, 7, 9 and 10 as the binding protein of average molecular mass of 17 kDa), the binding profile for CsA revealed specific binding to the 50–54 kDa fraction (FIG. 13 B); rapamycin (70 mM) did not compete for binding to either protein. Specific binding of [$^3$H]-rapamycin overlapped FK-506 and CsA specific binding (FIG. 13 C); no binding proteins unique for rapamycin were found.

Figure 14:
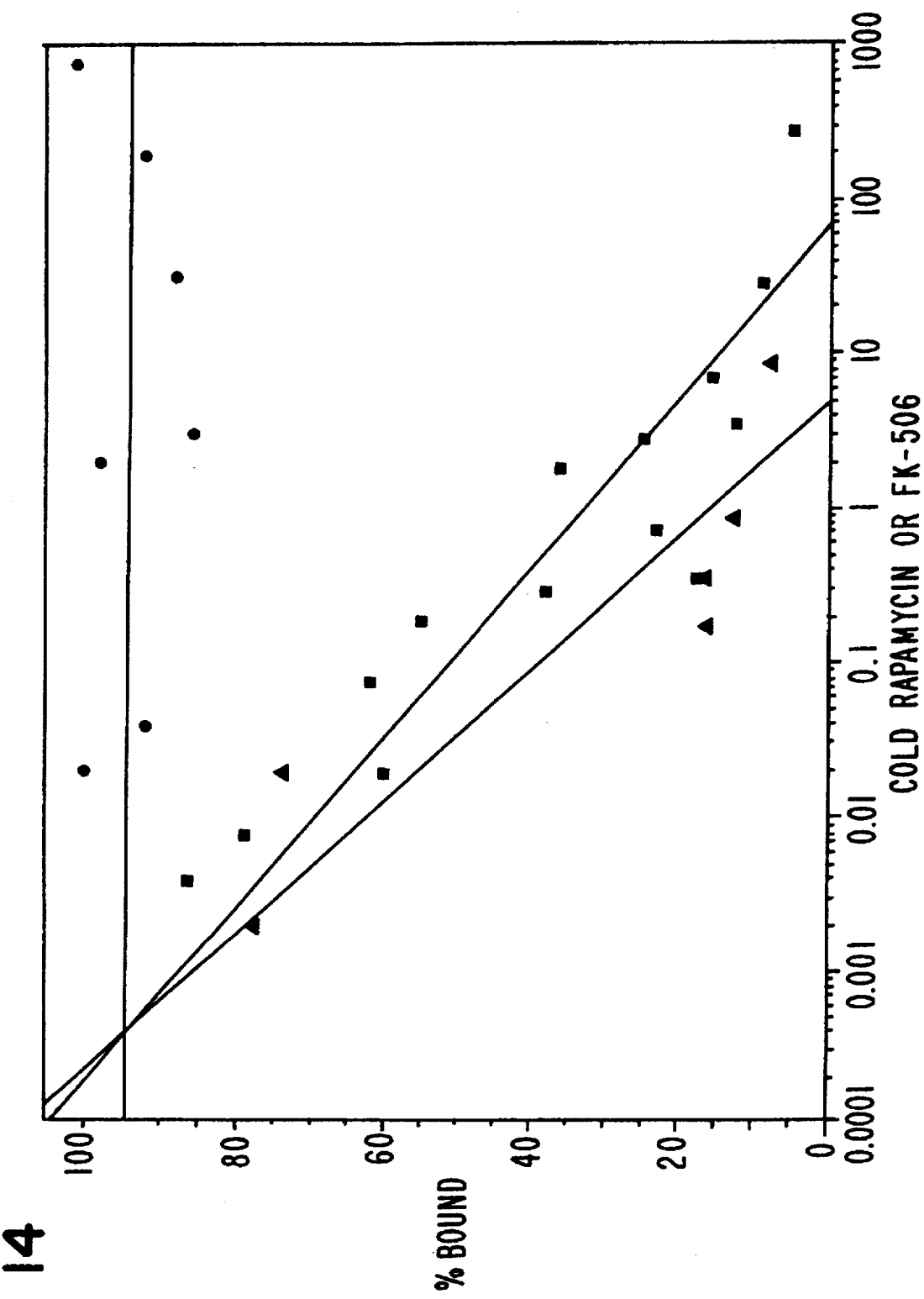
FIG. 14 shows binding competition curves between CsA and FK-506 or rapamycin with a purified JURKAT cell 50–54 kDa immunophilin.

Binding competition curves for CsA, FK-506 and rapamycin were generated using the purified 50–54 kDa binding protein (FIG. 14). Binding of [$^3$H-dihydro]-FK506 to this protein was inhibited in a dose-dependent manner by rapamycin (B$_{50}$=0.1 nM), whereas binding of [$^3$H]-CSA to this protein was not affected by rapamycin at concentrations as high as 300 nM. FK-506 inhibited the binding of [$^3$H]-CsA to the 50–54 kDa protein at all concentrations tested.

These results indicate that the binding sites for FK-506 and CsA on the purified 50–54 kDa protein are closely related, that the binding sites on this protein for CsA and rapamycin are distinct, and overlap or interaction of the CsA and FK-506 binding sites occur.

EXAMPLE 13

Purification of the 10–12 and 50–54 kDa Immunophilins from JURKAT Cells

Figure 15:
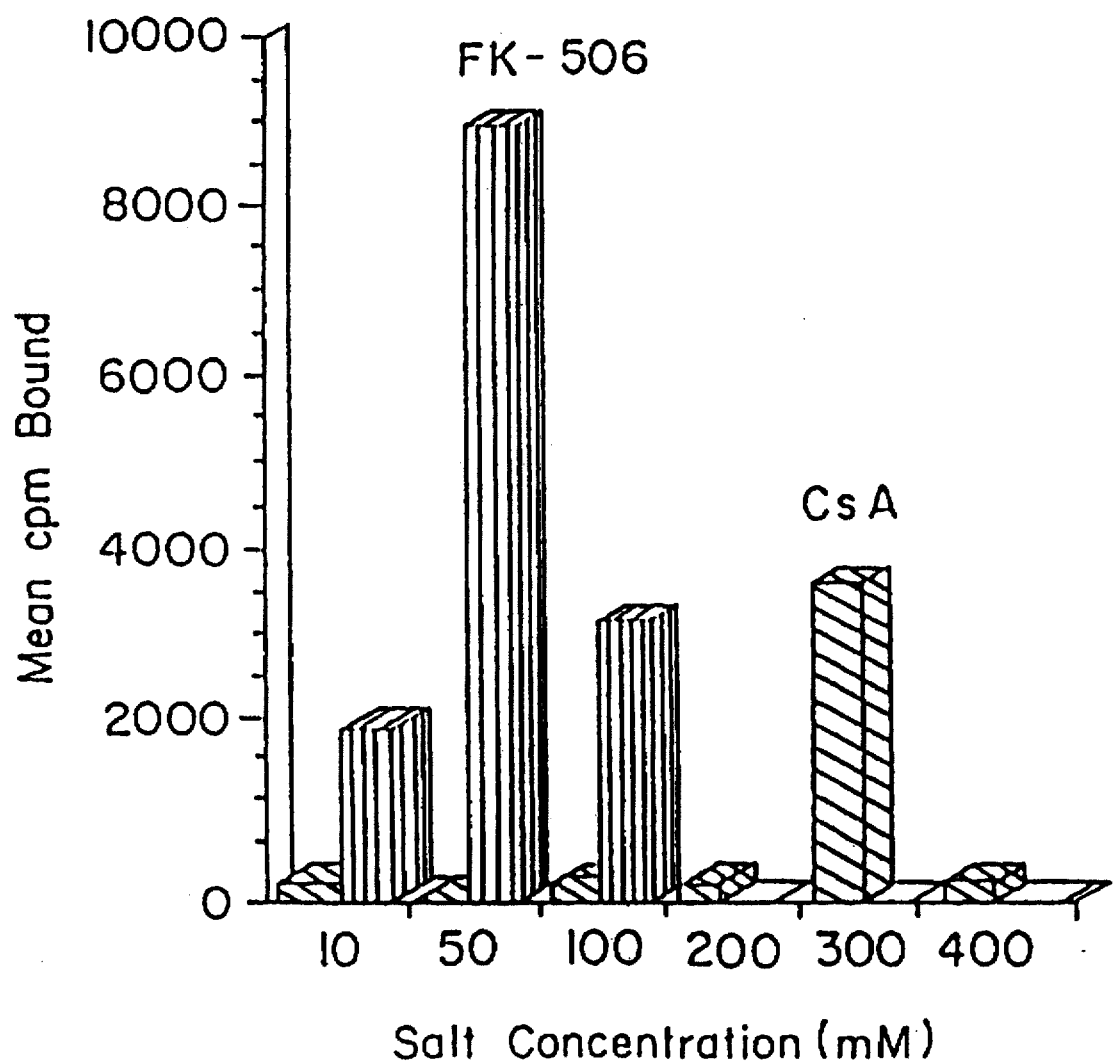
FIG. 15 shows the elution profile of JURKAT lymphocyte CsA and FK-506 binding immunophilins from a Matrex Gel Blue A column as a function of salt concentration.

The 10–12 kDa binding protein disclosed in Examples 4, 6, 11 and 12 above, and the 50–54 kDa binding protein disclosed in Examples 4, 6, 7, 9 and 10 were also purified from JURKAT T-cells by the following scheme. One mL of S100 (40–55 mg/mL, from Example 12) was passed through a Matrex Gel Blue A (Amicon Corp., Denvers, Mass.) affinity column (7×0.8 cm, 3 mL bed volume) equilibrated with 10 mM phosphate buffer, pH 6.8. Blue A is equivalent to Cibacron Blue dye. The dye is bound through a $C_{12}$ spacer arm onto an agarose base matrix. Proteins were fractionated with a step gradient of phosphate buffer at 10, 50, 100, 200, 300 and 400 mM, pH 6.8. These fractions were assayed for binding of immunosuppressive drugs, concentrated by rotary evaporation, and dialyzed against 20 mm sodium phosphate buffer, pH 6.8. The bulk of the FK506/rapamycin binding 10–12 kDa binding protein eluted at 50 mM buffer; the CsA binding 16–18 kDa binding protein eluted at about 300 mM buffer (FIG. 15).

The 50–54 kDa binding protein was also separated using the Matrex Gel Blue A affinity column. As it was unexpectedly found that this protein did not bind to this matrix, the matrix was used in a negative selection adaptation. Therefore, in an alternate purification scheme for this protein, pools of size-excluded S100 (see above) containing this protein were concentrated with a 30 kDa cutoff filter (Centricon™), adjusted to 80 mM sodium phosphate, pH 6.8, mixed with 0.5 mL of Matrex Gel Blue A for 15 minutes at 25° C., centrifuged in a Beckman Microfuge, and the supernatant fluid containing the 50–54 kDa protein collected.

Concentrated fractions from Matrex Blue A chromatography (5–10 mg protein/mL) enriched for either the 10–12 kDa, 16–18 kDa and 50–54 kDa binding proteins were clarified by microfiltration (0.45 µg filter), and 500 µl samples injected into a BioSil SEC-125 HPLC column (600×7.5 mm, BioRad, Richmond, Calif.) that was part of a Beckman System Gold Programmable Solvent Module No. 126 HPLC system, using as solvent 20 MM 30 sodium phosphate buffer, pH 6.8, at a flow rate of 1 mL/minute. Elution of proteins was monitored by a Beckman Model 160 Absorbance Detector and Model 427 Integrator. Collected fractions were tested for binding, pooled, concentrated by rotary evaporation, and dialyzed against 5 mM potassium phosphate, pH 6.8.

Figure 16:
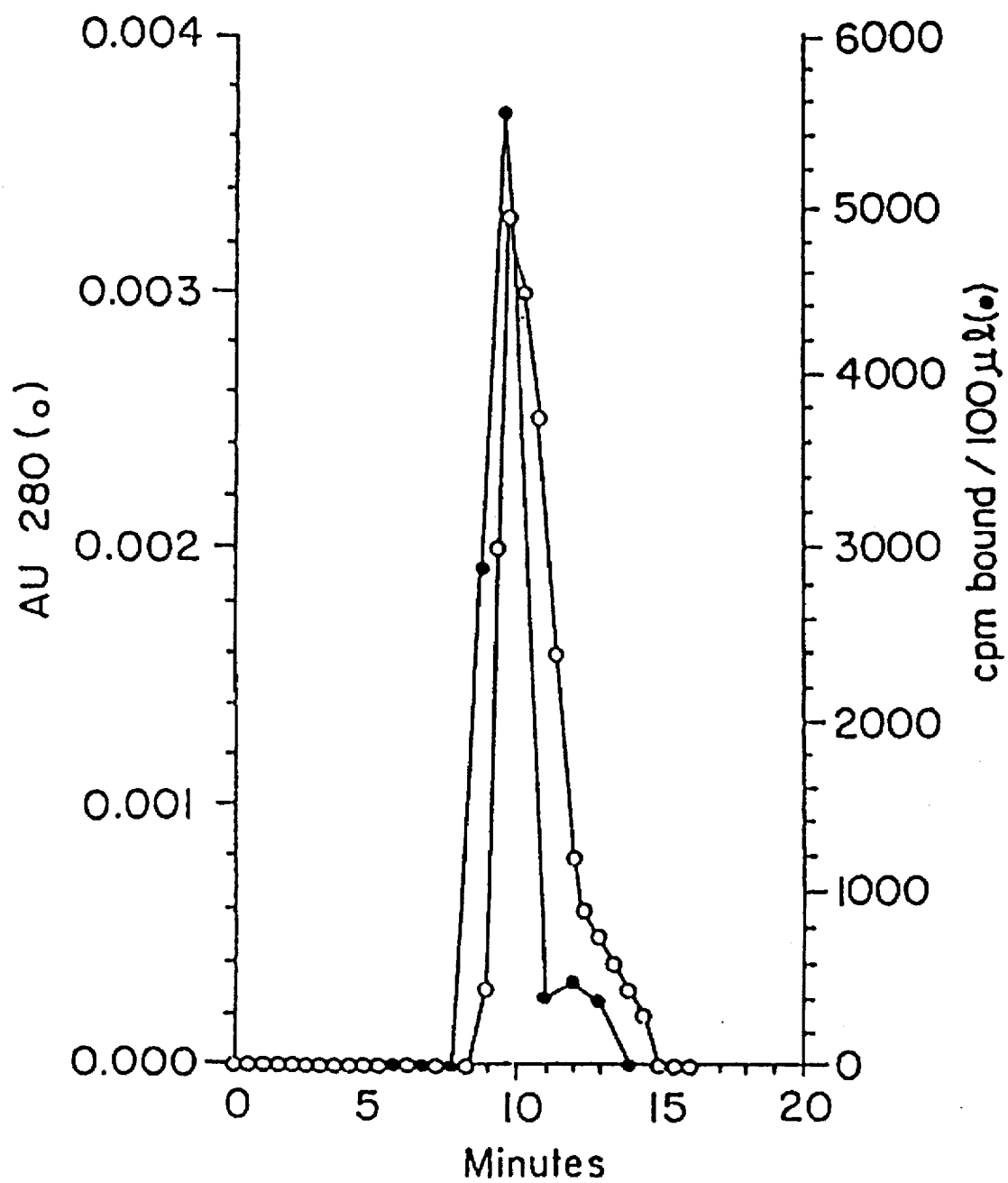
FIG. 16 shows specific binding of CsA to a purified JURKAT cell 17–19 kDa immunophilin.
Figure 17:
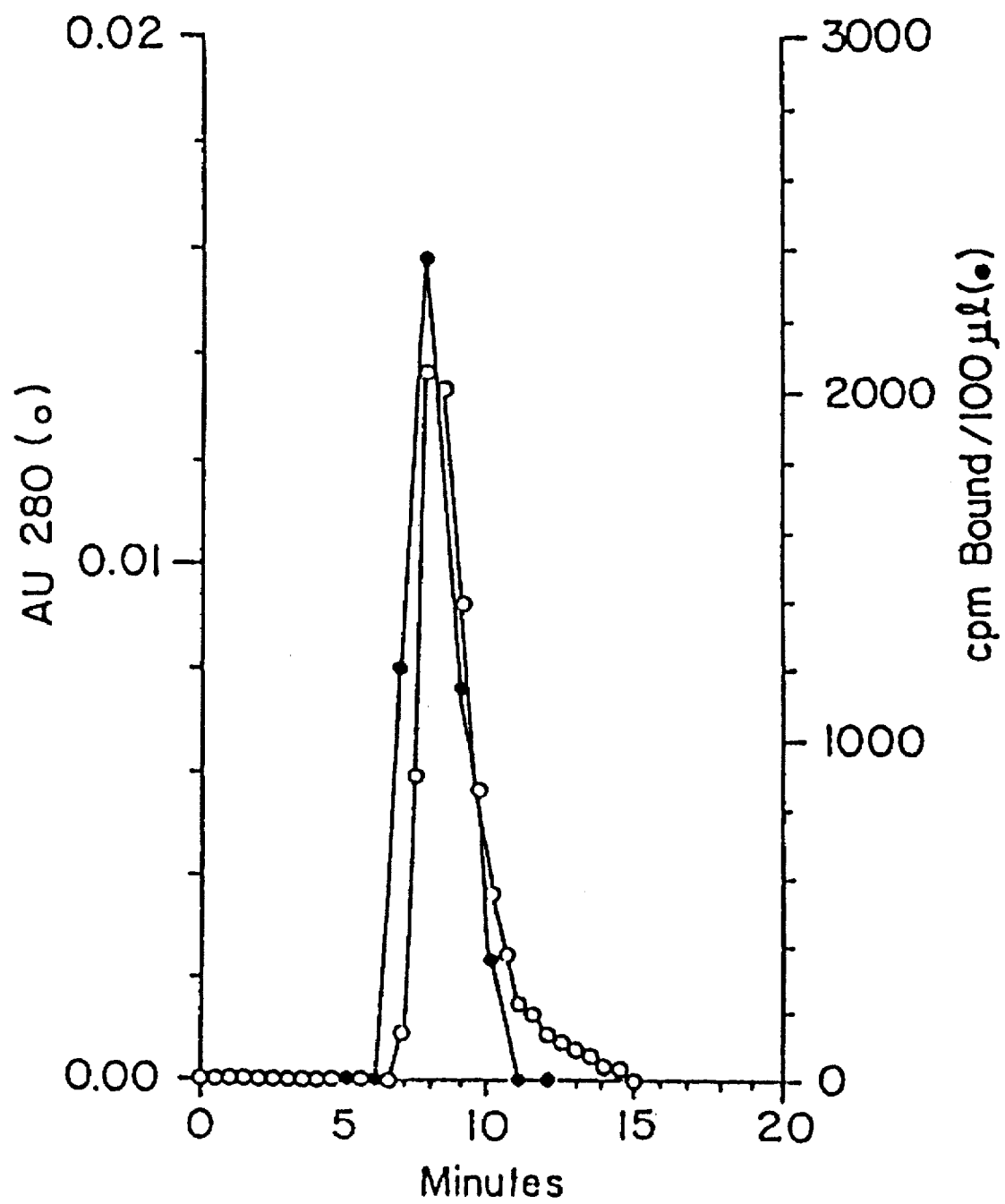
FIG. 17 shows specific binding of FK-506 to a purified JURKAT cell 10–12 kDa immunophilin.
Figure 18:
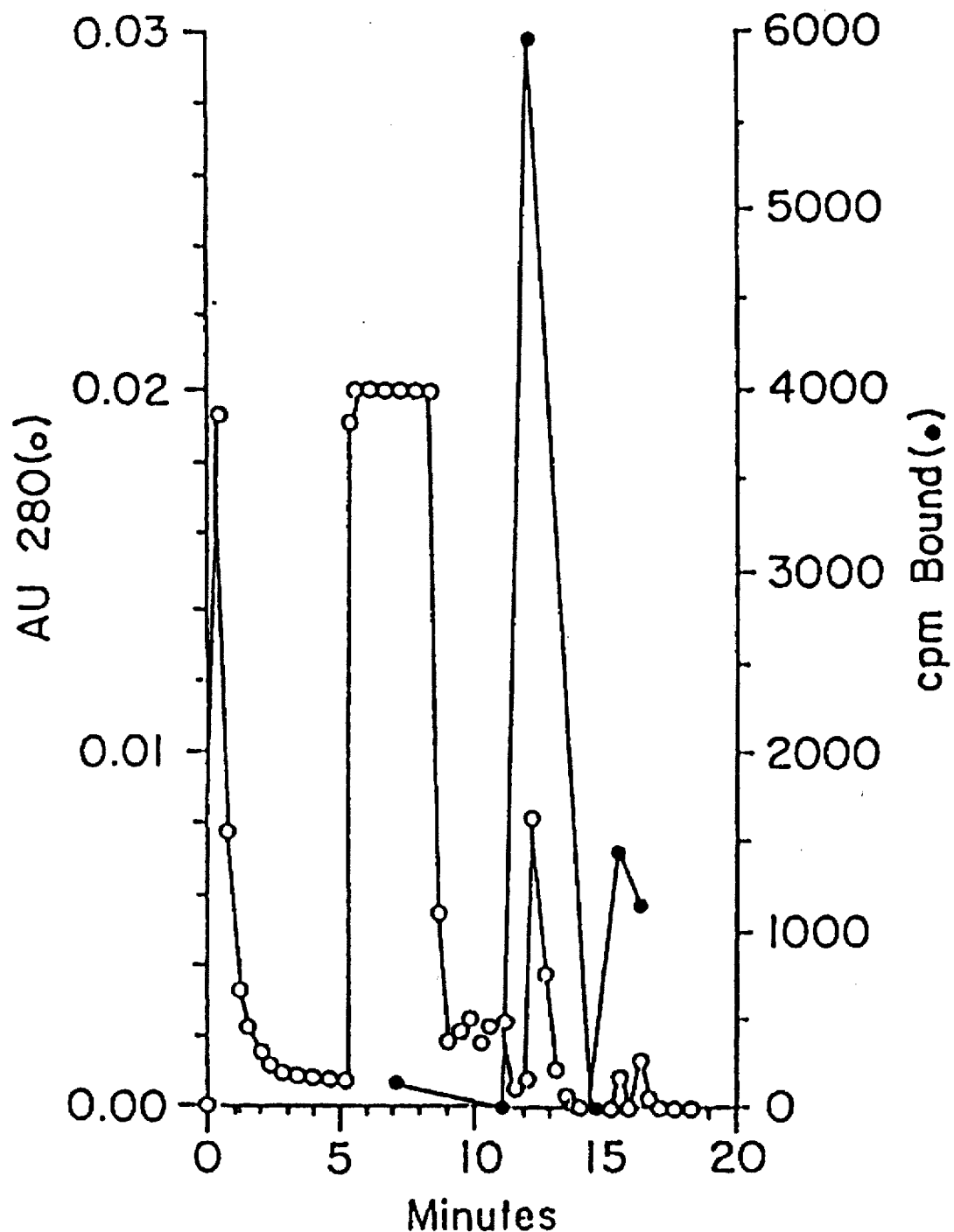
FIG. 18 shows the specific binding of CsA to a purified JURKAT cell 50–54 kDa immunophilin.
Figure 19:
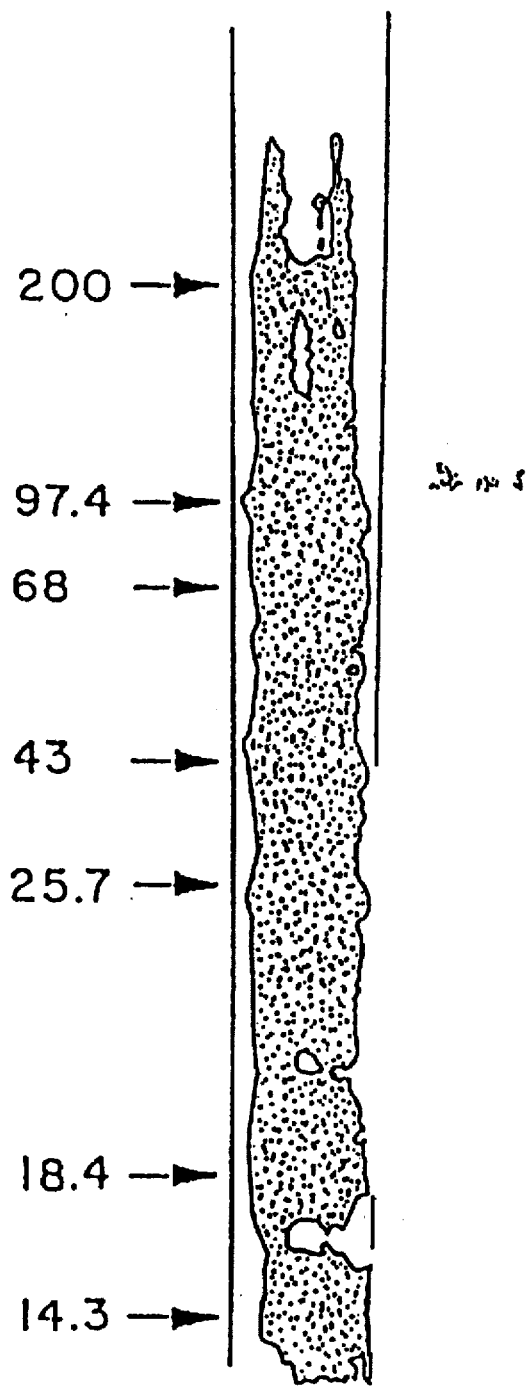
FIG. 19 shows analytical SDS-PAGE of a purified 10–12 kDa immunophilin.

Pooled fractions from the HPLC procedure (100–300 µg protein/mL) were filtered as above and injected into a Beckman TSK CM 2SW Spherogel weak cation exchange HPLC column (26×4.6 mm), and fractionated with 5 mm potassium phosphate buffer, pH 6.8, at a flow rate of 0.5 mi/minute. For the 16–18 kDa protein fraction, this procedure produced a single protein peak (eluted at 9–10 minutes) that bound [$^3$H]-CsA (FIG. 16). For the 10–12 kDa protein fraction, this procedure also produced a single protein peak (eluted at 7–8 minutes) which bound [$^3$H-dihydro]-FK-506 (FIG. 17). For the 5054 kDa binding protein, this procedure produced a single protein peak (eluted at 12–14 minutes) that was coincident with all of the binding activity (FIG. 18).

Purity of the isolated proteins was tested by SDS-PAGE electrophoresis as described above. Briefly, protein samples (3–5 µg) were dissolved in an equal volume of Sample Preparation Buffer (0.125 Tris buffer, pH 6.8, 3% SDS, 20% glycerol and 10% β-mercaptoethanol) and boiled for 3 minutes. Samples were loaded onto a 10–20% gradient gel (Integrated Separation Science, Boston, Mass.), and were separated at 30 mA; gels were fixed and stained by the Daiichi silver staining procedure. The results are shown in Figure. Lane 1 contains the molecular weight standards. Lane 2 contains the 10–12 kDa protein purified through the BioSil SEC 125 molecular weight exclusion step above. Lane 3 contains the same material purified through the final weak cation exchange separation step (TSK CM-2 SW Spherogel above). By this criterion, 10–12 kDa binding protein was purified to homogeneity. Table 5 below summarizes the purification of the 10–12 kDa protein by this scheme, and Table 6 is the counterpart for the 50–54 kDa binding protein.

TABLE 5

Purification Summary of the 10–12 kDa Binding Protein

| Step | Volume (mL) | Protein (mg/mL) | Binding (CPM/mg) | Recovery (%) |
|---|---|---|---|---|
| S100 | 13 | 57 | $1.0 \times 10^3$ | 100 |
| Matrex Blue | 3 | 10 | $15.4 \times 10^3$ | 17.5 |
| Size exclusion | 2 | 0.25 | $48.3 \times 10^3$ | 0.4 |
| Cation exchange* | 1 | 0.02 | $1.25 \times 10^{6\,6}$ | 0.04 |

*1250-fold purification over S100

TABLE 6

Purification Summary of the 50–54 kDa Binding Protein

| Step | Volume (mL) | Protein (mg/mL) | Binding (CPM/mg) | Recovery (%) |
|---|---|---|---|---|
| S100 | 20.0 | 4.46 | $3.0 \times 10^5$ | 100 |
| Matrex Blue | 2.5 | 15.7 | $1.1 \times 10^5$ | 43.9 |
| Size exclusion | 1.5 | 1.24 | $7.7 \times 10^5$ | 2.1 |
| Matrex Blue | 1.0 | 0.68 | $1.26 \times 10^7$ | 0.71 |
| Cation exchange* | 3.2 | 0.013 | $7.7 \times 10^7$ | 0.03 |

*250-fold purification over S100

Scatchard analyses of the 50–54 kDa binding protein revealed a single class of non-interacting binding sites with a binding constant, Kd, for the interaction of CsA with this protein of about 64 nM, and a binding capacity of about 3.2 nmol/mg. The interaction of FK-506 with this protein revealed a Kd of about 2 nM, a binding capacity of about 0.3 nmol/mg, and a single class of non-interactive binding sites.

Scatchard analyses of the binding of labeled FK506 to the purified 10–12 kDa protein revealed that the 5 Kd was about 1.3 nM, and the binding capacity was about 0.5 nmol/mg.

No cooperativity was observed for the binding of CsA or FK-506 to the 50–54 kDa protein, nor for the interaction of FK-506 with the 10–12 kDa binding protein.

EXAMPLE 14

Purification of an About 80–100 kDa Binding Protein from Human Spleen

Figure 6:
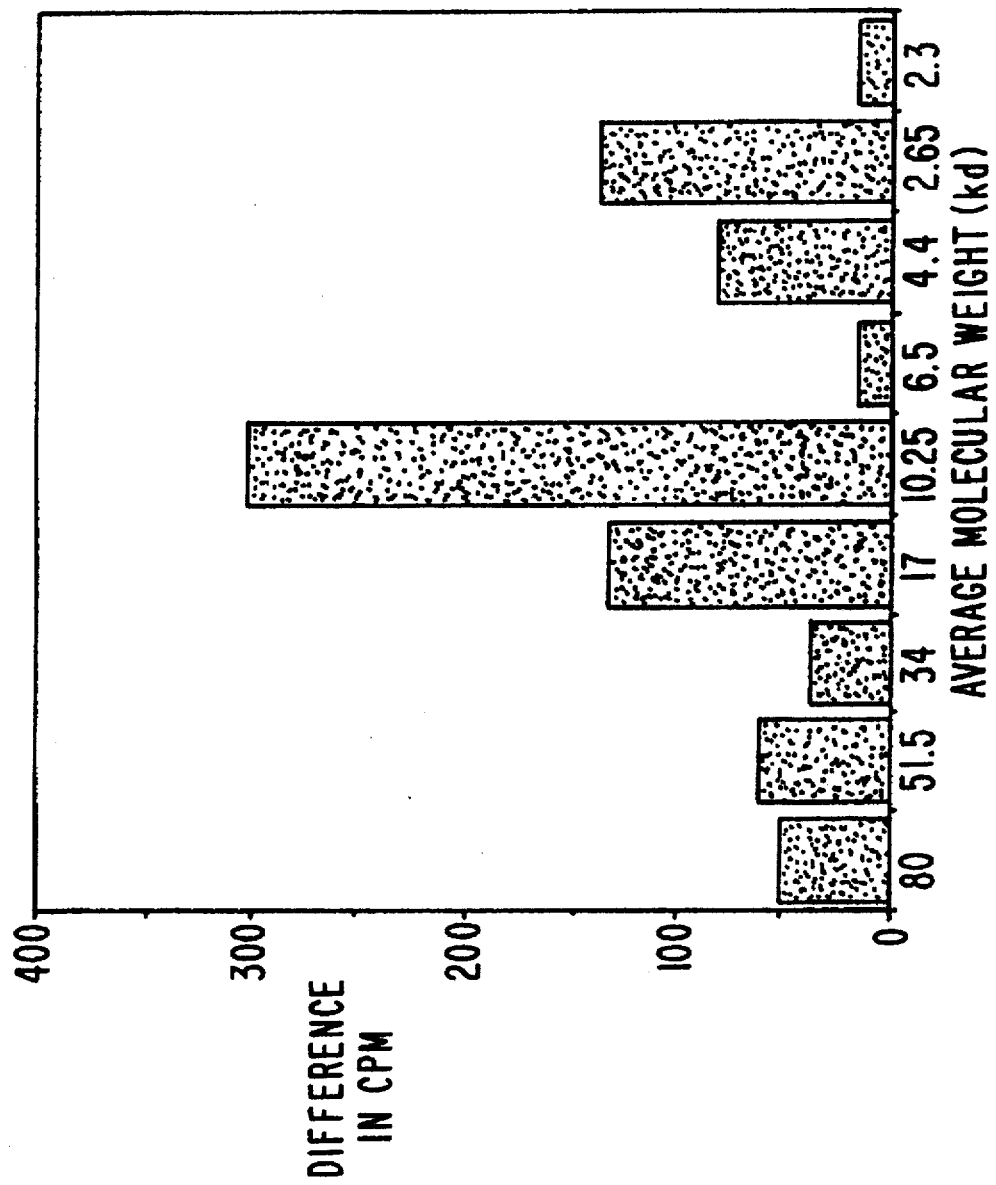
FIG. 6 shows the cyclosporine binding activities of the column fractions from FIG. 5.

The protocol of EXAMPLE 11 was used further to purify the 80–100 kDa CsA binding protein described in Example 4, FIGS. 5 and 6, from human spleen. A summary of the purifications obtained are presented in Table 7.

TABLE 7

| Step | Protein (mg) | Total (mL) | Binding (DPM/mg) | Yield (%) | Purification (fold) |
|---|---|---|---|---|---|
| S100 | 2195 | 35 | 477 | 100 | 1 |
| Rotofor PI (4.5–5.1) | 258 | 10 | 886 | 11.8 | 1.9 |
| Size exclusion | 3.2 | 4 | 48,150 | 0.15 | 101 |
| CM 5/10 mM phosphate | 0.68 | 4 | 163,882 | 0.03 | 344 |

This procedure purified the 80–100 kDa protein about three hundred and fifty fold.

EXAMPLE 15

Purification of Calf Thymus 50–54 kDa Immunophilin to Homogeneity

Figure 20:
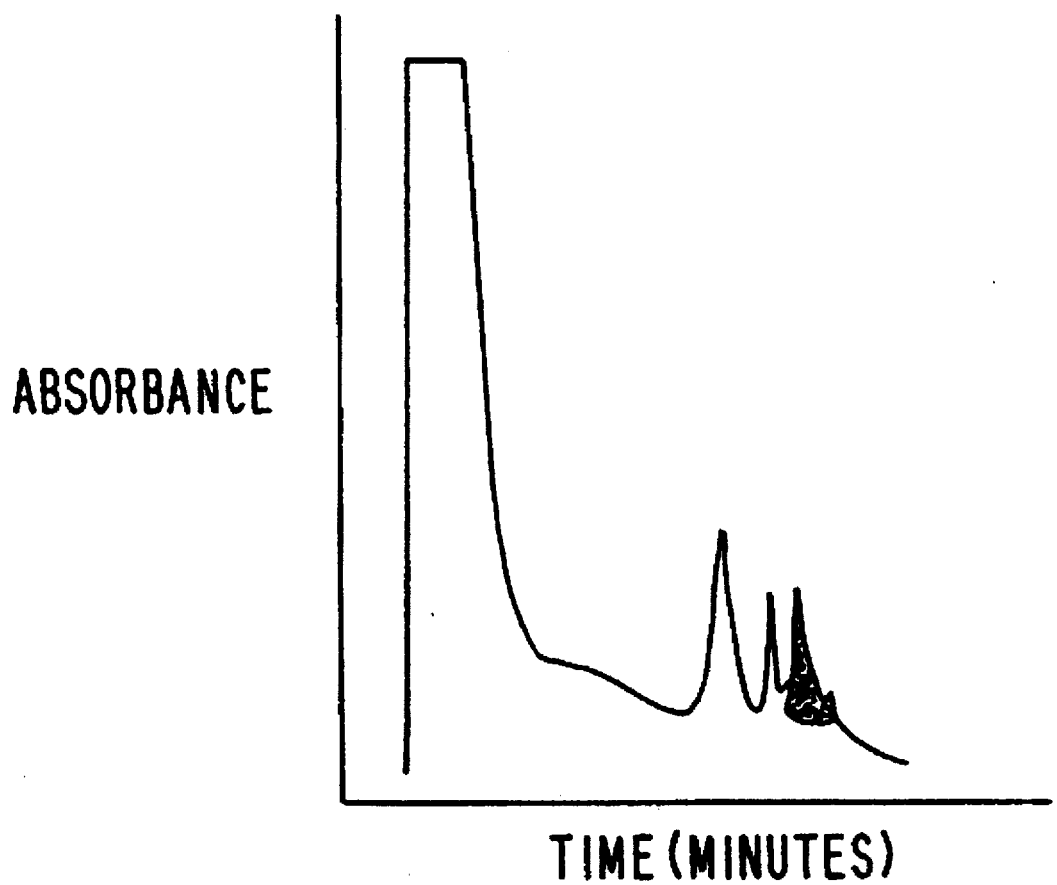
FIG. 20 shows ion exchange chromatography of a purified calf thymus 50–54 kDa immunophilin.
Figure 21:
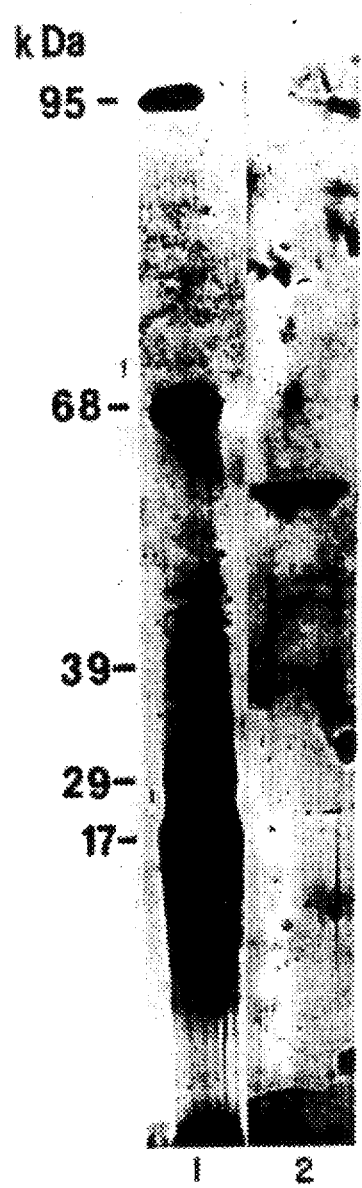
FIG. 21 shows analytical SDS-PAGE of a purified calf thymus 50–54 kDa immunophilin.

The ROTOFOR™ isoelectric focusing—size exclusion chromatography—ion exchange chromatography preparative-scale protocol employed in Example 11 to purify to homogeneity human spleen 50–54 kDa immunophilin was adapted to calf thymus tissue. At the ion exchange step, the purified protein was passed 10 through a weak cation exchange CM 250×4.6 nm cartridge that had been preequilibrated with 5 mM potassium phosphate buffer, pH 6.8 using a linear gradient of from 5–500 mM of phosphate buffer. The [$^3$H]-CsA binding fraction (a single peak at 200 mM phosphate buffer, pH 6.8, at 23 mins.) was obtained (FIG. 20), and analyzed by SDS-PAGE using a 10% acrylamide gel, using the Laemlli (1970) procedure (FIG. 21). In FIG. 21, Lane 1 contains molecular weight markers, and Lane 2 the purified 50–54 kDa protein (shown with a bar). The specific binding activity for [$^3$H]-CSA for this calf thymus preparation was about 5.0 pmol/mg protein. The corresponding human spleen immunophilin showed a specific binding activity of about 140 pmol/mg.

As the purified 50–54 kDa calf thymus immunophilin was unstable in dilute solutions at −20° to −70° C., it was preferred to store the protein at 4° C.

Homogeneity was confirmed by 2-D electrophoresis which demonstrated a single spot in the neutral to acidic region (pI 6.3-6-8). In the same system, the pI for the 10–12 kDa immunophilin was about 8.5–9.0.

EXAMPLE 16

Figure 22:
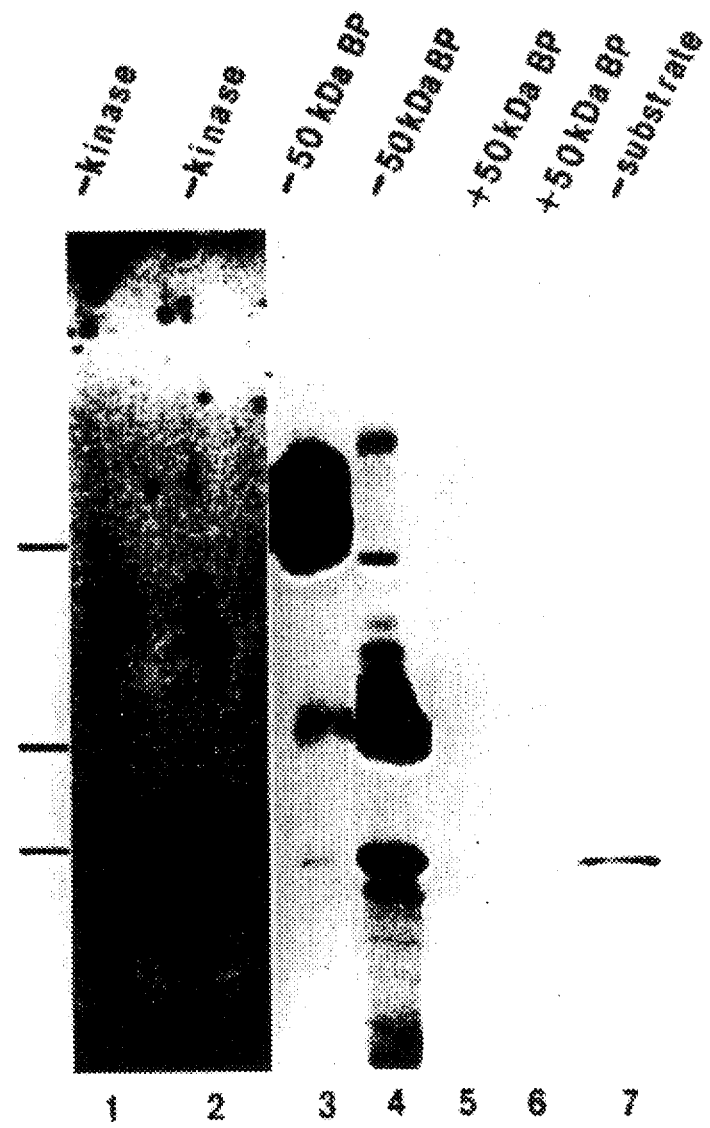
FIG. 22 shows the radioautographic results of a cAMP dependent protein kinase assay in the presence of purified calf thymus 50–54 kDa immunophilin.

Effects of the 50–54 kDa Immunophilin on cAMP-Dependent Protein Kinase cAMP-dependent rabbit muscle protein kinase (7.0 µg) or buffer control was incubated with 2 mg of histone or partially dephosphorylated casein partial hydrolysate and 0.7, 1.4 and 2.1 µg of a homogeneous preparation of 50–54 kDa immunophilin isolated from calf thymus in 5 mM potassium phosphate buffer (pH 6.8) containing 4 mM $MgCl_2$ and 1.5 mM cAMP (Sigma Chem. Co.) in a total volume of 70 µL. γ-$^{32}$P-ATP (2.5 µCi, 3000–6000 Ci/mmol) was added to start the reaction. The reaction was terminated after 15 minutes by the addition of EGTA (86 mM) and of SDS-PAGE sample treatment buffer, followed by heating at 100° C. for 2 minutes. One third of the mixture was loaded on an SDS-PAGE gel, and electrophoresis carried out by standard methods. After migration of the dye front and buffer front from the gel was complete, gels were dissembled and dried in vacuo against filter paper. The dried gels were autoradiographed against X-ray film (FIG. 22). In FIG. 22. Lane 1 contains the immunophilin and histones, but no protein kinase. Lane 2 contains the immunophilin and casein, but no protein kinase. Lane 3 contains histones and protein kinase, but no immunophilin. Lane 4 contains casein and protein kinase, but no immunophilin. Lane 5 contains immunophilin, protein kinase and histones. Lane 6 contains immunophilin, protein kinase and casein. Lane 7 contains immunophilin and protein kinase. To quantify the radioactive bands, films were read by a densitometer scanning at 600 nm. As shown by the radioautogram data of FIG. 22, the activity of the protein kinase with either histone or casein as substrate was abolished by as little as 0.7 µg of the 50–54 kDa immunophilin (Lanes 6 and 7). The 50–54 kDa immunophilin exhibited no endogenous protein kinase activity (Lanes 1 and 2), nor was it a substrate for kinase activity (Lanes 5 and 6).

In an experiment (data not shown) similar to that shown in FIG. 22, Lane 6 using 0.7 µg of the immunophilin, neither CsA (600 nM), FK-506 (60 nM) nor rapamycin (60 nM) influenced the inhibitory effect of the immunophilin on cAMP-activated protein kinase activity.

EXAMPLE 18

Rotamase Activity of 50–54 kDa Immunophilin

The homogeneous calf thymus about 50–54 kDa immunophilin (3.5–17.5 µg) was assayed for rotamase activity as described above using as substrate the peptides shown in Table 8. The about 50–54 kDa immunophilin was devoid of significant rotamase activity using peptide substrates with which the homogeneous 10–12 kDa immunophilin which specifically binds FK-506 and rapamycin, but not CsA, demonstrates rotamase activity. The highest apparent rotamase activity for the 50–54 kDa protein was 0.45 $k_{obs}$ ($m^{-1}$), but this rate did not increase when the protein concentration was increased 5-fold. Only peptidyl propyl cis-trans isomerase activity to $k_{obs}$ values of greater than about 0.5 $min^{-1}$ are considered significant. Values below this are not considered to be due to the catalytic properties of the protein being analyzed.

TABLE 8

Rotamase Activity of the 10–12 kDa and 50–54 kDa Immunophilins

| | $k_{obs}$ ($min^{-1}$) | |
|---|---|---|
| SUBSTRATE (SEQ ID NOS: 4–14 respectively) | 50–54 kDa | 10–12 kDa |
| Suc—Ala—Gly—Pro—Phe—pNA | 0.40 | a |
| Suc—Ala—Glu—Pro—Phe—pNA | a | a |
| Suc—Ala—Lys—Pro—Phe—pNA | 0.24 (0.1b) | 0.36 |
| Suc—Ala—Phe—Pro—Phe—pNA | 0.18 | 3.0 |
| Suc—Ala—Leu—Pro—Phe—pNA | 0.16 | 1.61 |
| Suc—Ala—Ala—Pro—Leu—pNA | 0.45 (0.24) | 0.93 |
| Suc—Ala—Gln—Pro—Phe—pNA | 0.22 (0.17) | 0.23 |
| Suc—Ala—His—Pro—Phe—pNA | 0.06 | a |
| Suc—Ala—Ile—Pro—Phe—pNA | 0.02 | 0.69 |
| Suc—Ala—Nle—Pro—Phe—pNA | 0.25 (0.17) | 0.58 |
| Suc—Ala—Trp—Pro—Phe—pNA | 0.14 | 0.21 |
| Suc—Phe—Pro—Phe—pNA | 0.06 | 0.63 | a: no activity observed
b: uncatalyzed rate

EXAMPLE 17

Effects of Purified Calf Thymus Immunophilins on Lck Tyrosine Kinase and Protein Kinase C Activities The 50–54 kDa immunophilin (0.7 µg) failed to influence the autophosphorylation of either lck tyrosine kinase or a mutant thereof in experiments conducted in collaboration with Dr. O. Sartor of the NIH.

The same amount of the same immunophilin failed to influence the protein kinase C activity of a rat brain preparation (the supernatant fluid from a 9,000×g×15 minutes centrifugation of a homogenate prepared by homogenizing 3.5 g of rat brain in 1 mL of Tris buffer, pH 7.5, using a probe sonicator) incubated in the presence of Amersham peptide substrate, calcium acetate (1.3 mM), L-α-phosphatidyl-L-serine (0.9 mole %), phorbol ester (2.7 µg/mL), DTT (3.3 mM), γ-$^{32}$P-ATP (0.25 µCi), ATP (15 pM) and magnesium acetate (5 mM) in 50 mM Tris buffer, pH 7.5 for 15 minutes at 25° C., stopping the reaction with 5% (v/v) HAc at 4° C., absorbing aliquots on filter papers, washing the papers with 5% (w/v) HAc and quantifying the radioactivity by LSC.

EXAMPLE 19

Amino Acid Composition, Molecular Weight and Partial Amino Acid Sequences of Purified Homogeneous Calf Thymus 50–54 kDa Immunophilin This analysis was carried out by K. Jarnigan et al., Syntex, Inc., under our direction. The 50–54 kDa immunophilin (36 µg by Lowry et al., 82 µg by Bradford et al.) was passed onto a 7% SDS-PAGE gel, and then transferred to PVDF film using CAPS-NaOH, pH 11, with 20% MeOH.

An approximately 0.7 µg sample of the protein immobilized on Immobilon film was hydrolyzed in gaseous HCl at 110° C. for 24 hours to hydrolyze the protein. The hydrolyzed amino acids were dissolved in 5 µL of $CH_2OH$ followed by 10 AL of borate buffer. An aliquot (1.0 µL) of the mixture was derivatized with the fluorescent reagents, orthophthalaldehyde (OPA) and fluorenylchloroformate (FCF), using a Hewlitt-Packard Amino Quant amino acid analyzer. Detection and quantitation after the HPLC resolution step used the fluorescence of the OPA and FCF derivatives of the amino acids. The peak area for each amino acid was corrected for the recovery of internal standards (norval and Sar) and compared to a three-point standard curve. Data was corrected for the "amino acids" present in the no-protein control.

In Table 9 there is shown the amino acid composition of the 50–54 kDa immunophilin in terms of mole % and residues/mole. Cys and Trp are not accounted for by this method of analysis. However, in a common protein such as a human serum albumin, cys and Trp account about 6% (w/w).

TABLE 9

|  | Mole % | Residues/mole | Relative to PHE |
|---|---|---|---|
| ASX | 11.66 | 53.8 | 55.8 |
| GLX | 12.82 | 58.8 | 51.5 |
| SER | 7.79 | 35.8 | 37.3 |
| HIS | 0.99 | 4.6 | 4.8 |
| GLY | 11.31 | 52.0 | 54.2 |
| THR | 5.30 | 24.4 | 25.4 |
| ALA | 6.34 | 28.1 | 30.4 |
| ARG | 3.96 | 18.2 | 15.0 |
| TYR | 4.66 | 21.4 | 22.3 |
| VAL | 4.97 | 22.3 | 23.9 |
| MET | 1.46 | 8.7 | 7.0 |
| PHE | 4.17 | 18.2 | 20.0 |
| ILE | 5.85 | 27.4 | 28.5 |
| LEU | 8.97 | 41.2 | 43.0 |
| LYS | 4.71 | 21.6 | 22.6 |
| PRO | 4.94 | 22.7 | 23.7 |

Thirteen tryptic peptides were resolved by RP-HPLC and sequenced. The C-terminal dodecameric peptide (SEQ ID NO:1) was identified as: Asp-Gln-Ile-Val-Glu-Leu-Thr-Val-Gly-Asn-Asn-Asn. This sequence was without homology in the Gene Bank database. Other nonhomologous internal partial tryptic peptides identified include (SEQ ID NO:2 and 3 respectively): Asn-Asn-Asp-Leu-Glu-Asn-Lys; and Ala-Glu-Asp-Glu-Phe-Asn-Phe.

EXAMPLE 20

Binding of CsA and FK-506 to Cytosolic Protein

Binding of $^3$H-CsA to proteins in a 100,000×g cytosol derived from CEM cells was determined using Method E (LH-20) for separating protein bound from unbound ligands.

Figure 23:
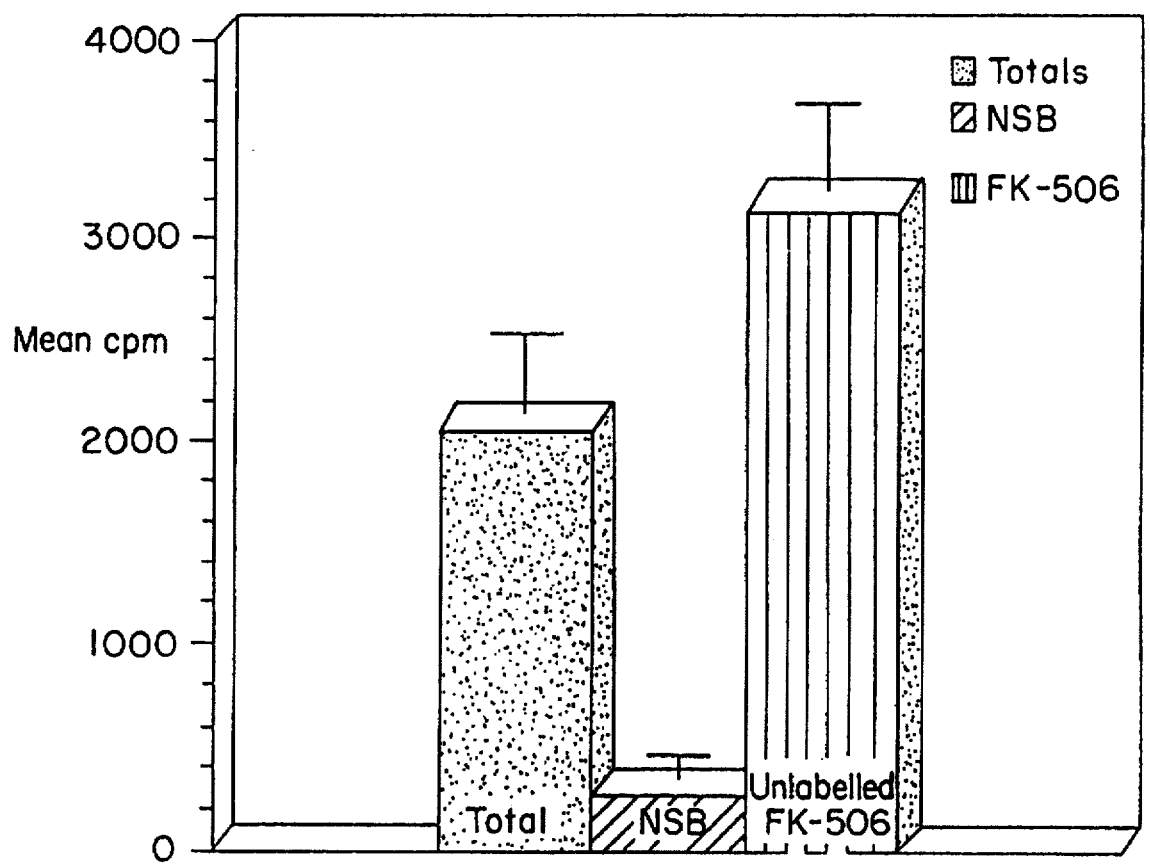
FIG. 23 shows the binding of CsA and of FK506 to binding proteins in CEM lymphocyte cytosol.

Whole cytosol (1 mg protein/mL) was incubated with [$^3$H]-CsA (60,000 cpm) in the absence and presence of unlabeled CsA and FK-506 (each 10 μg/mL). Unlabeled CsA, but not FK-506, competed against labeled CsA for binding to cytosolic proteins (FIG. 23).

EXAMPLE 21

A Specific Binding Protein for FK-506 in CEM Cytosol

Figure 24:
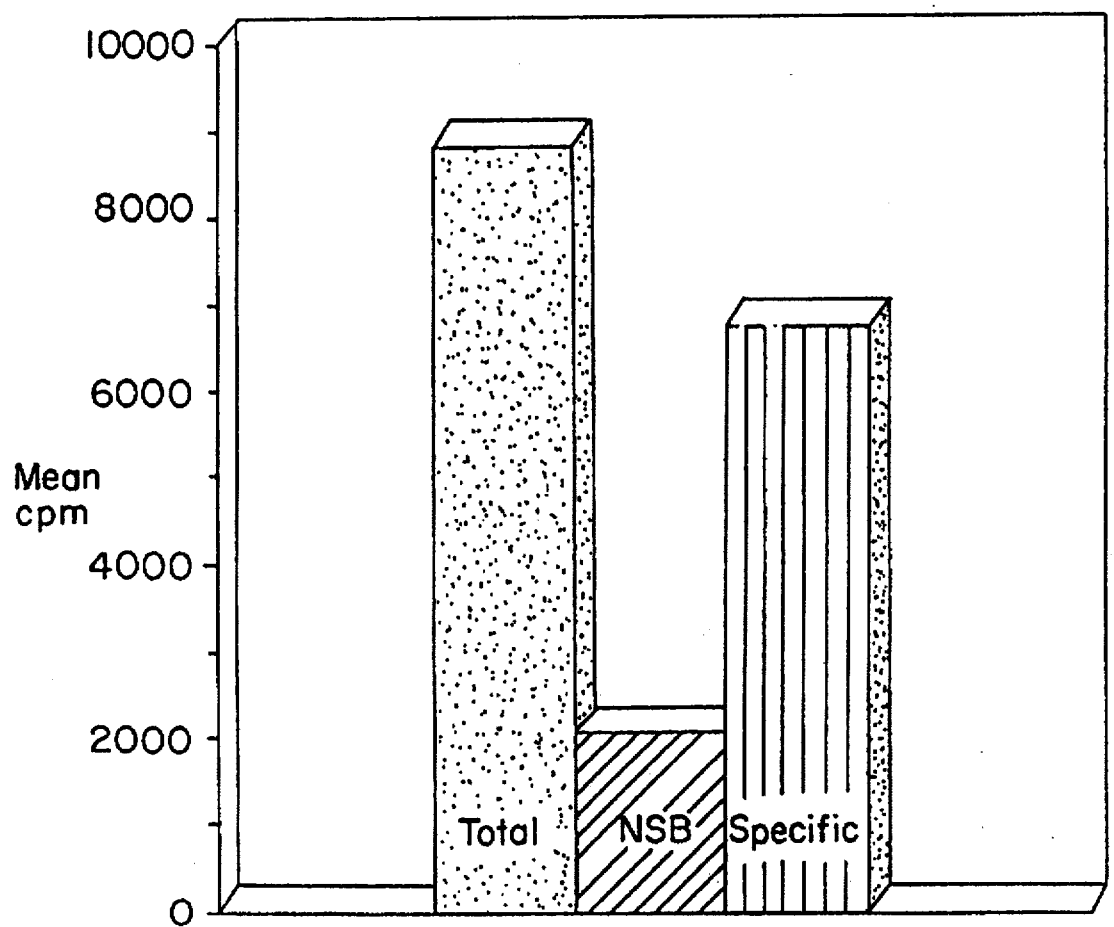
FIG. 24 shows specific binding of FK506 to a CEM lymphocyte cytosol binding protein.

Cytosol from CEM cells (1 mg protein/mL) was incubated with $^3$H-FK-506 (60,000 cpm) in the absence and presence of unlabeled FK-506 (10 μg/mL), and protein-bound and free labeled FK-506 separated by the Method E (LH-20). The results (FIG. 24) show that crude cytosol from CEM lymphocytes contains a specific binding protein for FK-506.

EXAMPLE 22

Purification of a FK-506 Binding Protein from CEM Cytosol

Figure 25:
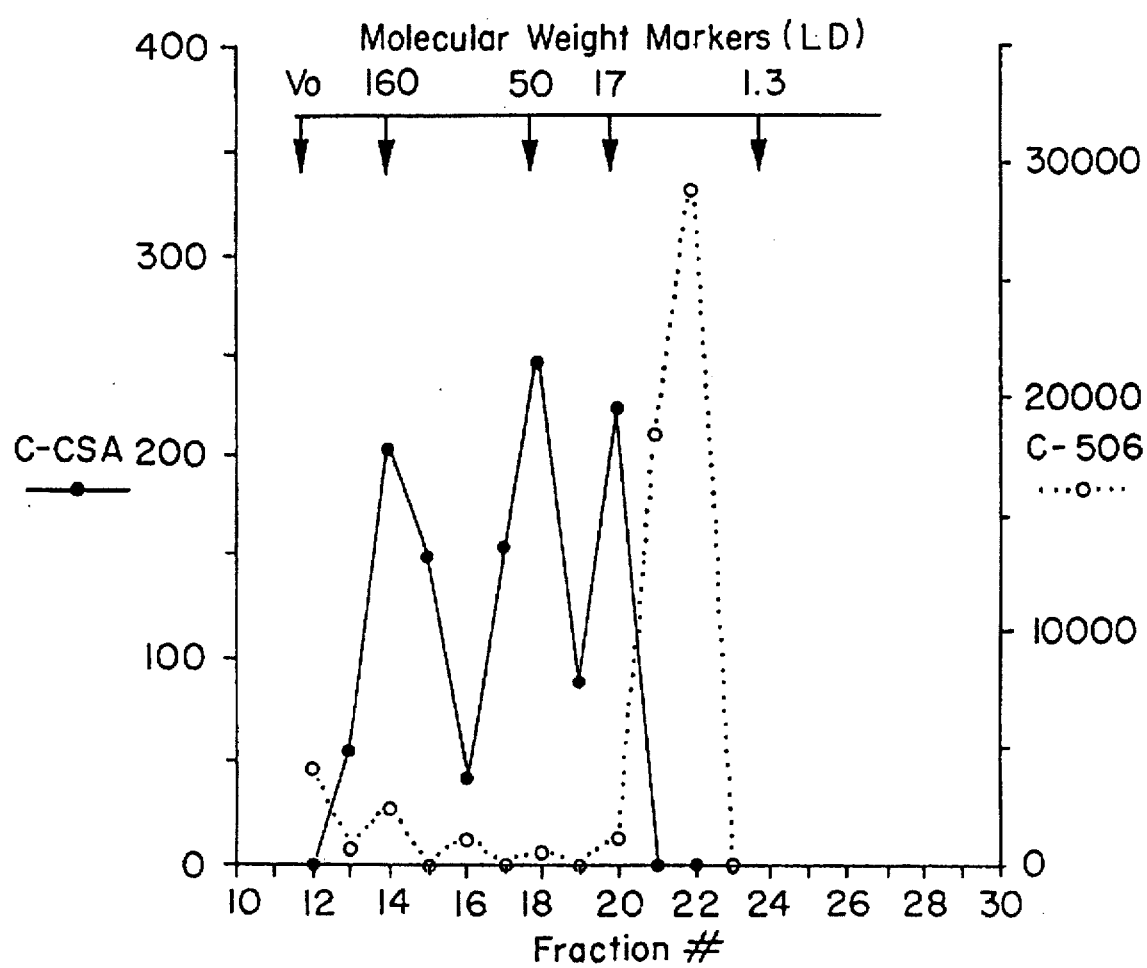
FIG. 25 shows the elution profile of FK506 binding proteins from CEM lymphocyte cytosolic fractions on a HPLC column.

CEM cytosol samples were filtered and injected using either a 250 μL or 500 μL loop with a Beckman HPLC instrument using a 7.5×300 mm Bio-Rad BioSil SEC 125 TSK column, a buffer consisting of 20 mM sodium phosphate, pH 6.8, and a flow rate of 1.0 mL/min. Fractions were collected, pooled, concentrated by rotary evaporation, assayed for protein by the BCA method, and assayed for binding to $^3$H-CSA (C-CsA in FIG. 25) or [$^3$H]-dihydro FK-506 (C-506 in FIG. 25). While CsA bound to fractions representing protein molecular weights of about 160 kDa, 50 kDa and 17 kDa, FK-506 bound primarily to a single peak at about 8–12 kDa, and secondarily to proteins eluting in fractions 14 (about 160 kDa) and 16 (about 100 kDa). The specific binding activity for FK-506 in the 8–12 kDa fraction was substantially greater than that for CsA in any of its individual binding protein fractions.

EXAMPLE 23

Direct Binding Profile for FK-506 in JURKAT Cytosol

The JURKAT cell line was maintained in RPMI 1640 medium (MA Bioproducts, Walkersville, Md.) with 10% FCS supplemented with L-glutamine and antibiotics (Life Technologies, Gaithersburg, Md.) at 37° C. and 5% $CO_2$. Cells (5×10$^9$) were collected, pelleted and washed with medium three times, and either used immediately as a source for cytosolic proteins or were frozen as a cell pellet at −70° C. Cells for extraction of proteins were homogenized with either a Teflon or ground glass homogenizer, using 0.02M sodium phosphate pH 6.8 with 0.5% sodium azide on ice. Completeness of cellular disruption was monitored with trypan blue exclusion. The crude homogenates were spun at 100,00×g for 1 hour, using a Beckman L5-65 ultracentrifuge and a 40.1 rotor and the supernatant fluid (S-100) isolated. The S-100 supernatant fluid (cytosol) was removed and the pellet discarded. Protein determinations were performed using either the Bradford procedure or binding to Coomasie blue using a Cobas Bios instrument (Roche Co., Nutley, N.J.). The S-100 supernatants were aliquoted and stored at −70° C.

Figure 26:
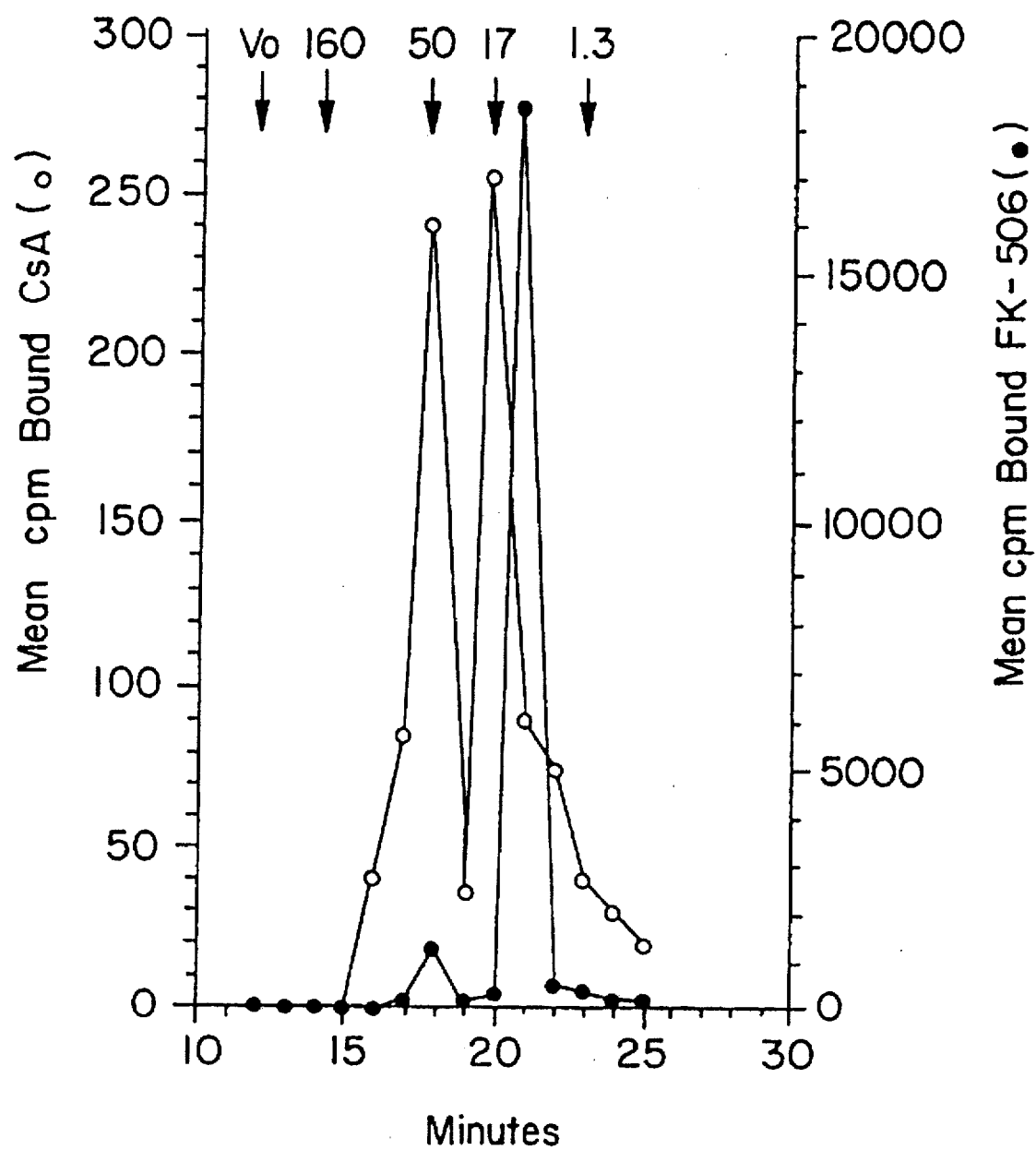
FIG. 26 shows HPLC fractionation of FK506 (●—●) and CsA (○—○) binding proteins derived from a JURKAT lymphocyte cytosol.

A sample of cytosol derived from JURKAT lymphocytes was equilibrated with [$^3$H]-dihydro FK-506 or [$^3$H]-CsA (each, 11.8 mol), and the solution passed through a molecular weight calibrated Bio-Rad Bio-Sil SEC 125 HPLC column at 1.0 mL/min. Fractions were collected and counted by liquid scintillation spectrometry in Packard Gold scintillation fluid. The binding profile shown in FIG. 26 demonstrates that FK-506 was bound primarily to a protein eluting in the 8–12 kDa molecular weight region, but also to a binding protein eluting in the 50–54 kDa region. CsA binding proteins eluted primarily in two molecular weight ranges, one at about 15–17 kDa and the other at about 50–54 kDa. Binding of CsA also occurred in the 8–12 kDa range, as a shoulder on the 17 kDa curve. Because of resolution limitations of this column, the 34–37 kDa immunophilin appears as a shoulder of the 50–54 kDa peak.

EXAMPLE 24

Scatchard Analyses of Binding Proteins

The binding proteins purified in Example 5 were incubated with increasing amounts of labeled ligand and the binding data analyzed according to Scatchard. Scatchard plots are shown in FIGS. 27A–C.

Figure 27A:
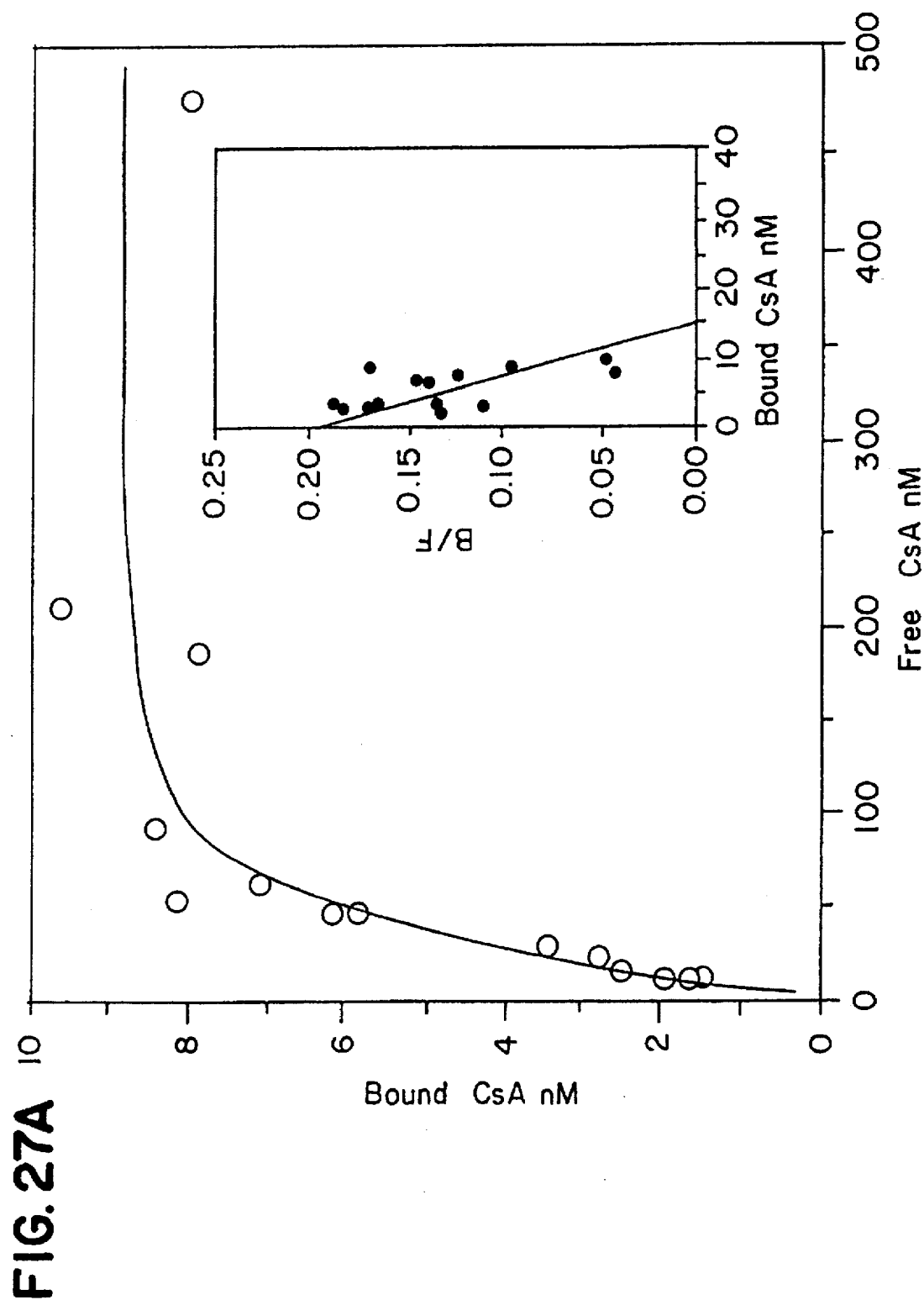
FIGS. 27(a-c) show Scatchard plots for CsA binding to the 50–54 kDa immunophilin (A), for FK506 binding to the same protein (B), and for the binding of FK506 to the about 10–12 kDa immunophilin.

FIG. 27A represents the direct binding of labeled CsA to the about 50 kDa protein preparation. The Kd of this interaction was about 64 nM, with a binding capacity of about 3.2 nmoles/mg protein. Cooperative binding was not observed.

Figure 27B:
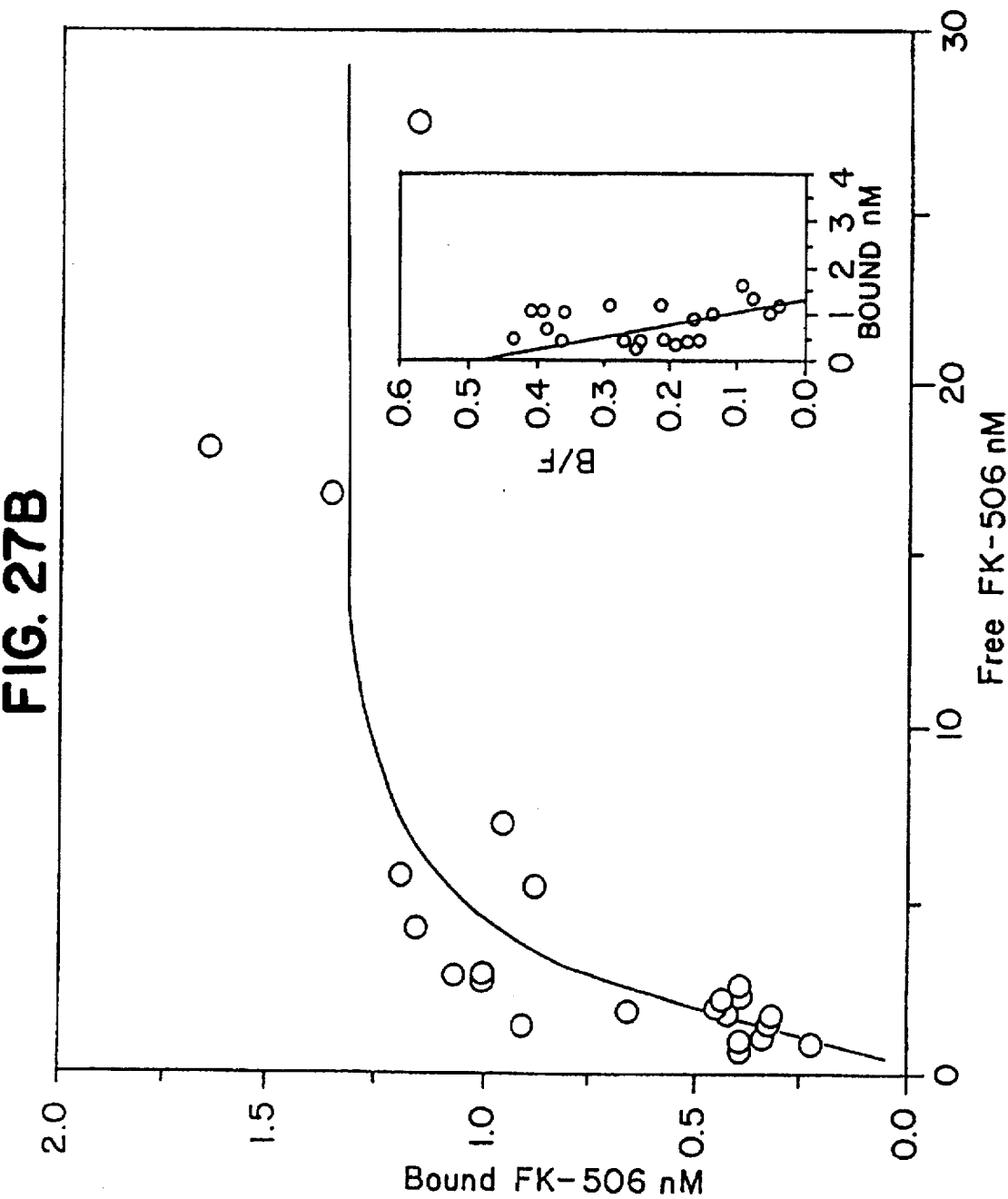

FIG. 27B represents the direct binding of labeled FK-506 to the same about 50 kDa protein preparation. This interaction yielded a Kd of about 2 nM, and a binding capacity of about 0.3 nmoles/mg protein.

When the binding of labeled FK-506 to about 8–12 kDa protein was analyzed (C), the Kd was about 1.3 nM and the binding capacity was about 0.5 nmoles/mg protein.

Kd values between about 1 and 10 nM were observed for purified preparations of the 15–20 kDa, 80–100 kDa and 150–200 kDa binding proteins.

No cooperativity was observed for the interaction of FK-506 with any of its binding proteins.

EXAMPLE 25

Purification of 50–54 kDa Binding Protein By Isoelectric Focusing from Jurkat Cells S-100 ($1.4\times10^9$ cells, 10 mL), prepared as in Example 4, was concentrated by centrifugation (2500×g, 1 hour, 4° C.) in a 30-kDa cutoff centriprep concentrator (Amicon, Danvers, Mass.). The concentrate (1 mL) was diluted with 15 mL of 10 mM phosphate buffer, pH 6.8, then reconcentrated to a volume of 5 mL. This step removed substantially all of the 17 kDa and 12 kDa binding proteins from S-100. The filtrate, containing proteins of over 30 kDa molecular mass, was then fractionated by isoelectric focusing at 4° C. in an instrument (Rotofor, BioRad, Richmond, Calif.) containing a prefocused solution of ampholytes (0.73% solids/vol. of pH 4–6, pH 6–8, and 0.37% solids/vol. of pH 8–10; total volume 50 mL). The cathodal solution was 0.1M $H_3PO_4$ and the anodal solution was 0.1M NaOH. The unit was focused until constant voltage (450 V) was achieved. The solution was separated into 20 fractions which were immediately tested for pH and for binding of $^3$H-dihydro FK-506 using the aforementioned LH-20 assay. The fraction binding to FK-506 (pH 6.19) was refocused under the same conditions using only the ampholytes contained in the 2.7 mL fraction (diluted to 55 mL with deionized water). Focusing was complete when a constant voltage of 2200 V was reached. Fractions (20) were tested for pH and binding as above.

The pH 6.29 fraction that bound FK-506 was then passed through a Bio-Sil-125 HPLC column at a flow rate of 1 mL/minute in 10 mM phosphate buffer, pH 6.8. Fractions obtained around the expected molecular mass of 50 kDa were pooled and passed through a Beckman TSK CM-2SW Spherogel column (26×4.6 mm) at a flow rate of 0.5 mL/minute in 10 mM phosphate buffer, pH 7.2. Fractions that contained the purified 50 kDa binding protein were pooled and used for binding assays.

The 50–54 kDa immunophilin was incubated for 15 minutes at 25° C. with varying concentrations of unlabeled FK-506 and 1.8 pmole of $^3$H-dihydro FK-506 in 20 mM Tris buffer, pH 7.4, containing 5 mM β-mercaptoethanol. Bound was separated from free using the LH assay. A plot of % Bound against the concentration of unlabeled FK-506 was linear between 0.0001 and about 10 nmol.

As determined by isoelectric focusing, the isolectric pH for the purified 50–54 kDa binding protein was about 6.3–6.8 Parallel testing with the 12 kDa, 17 kDa and 80–100 kDa binding proteins revealed isoelectric pH values of about 8.8, 9.1 and 4.5–5.0, respectively.

EXAMPLE 26

Protein Binding Assay for FK-506 in Whole Blood

Binding Assay

Figure 28A:
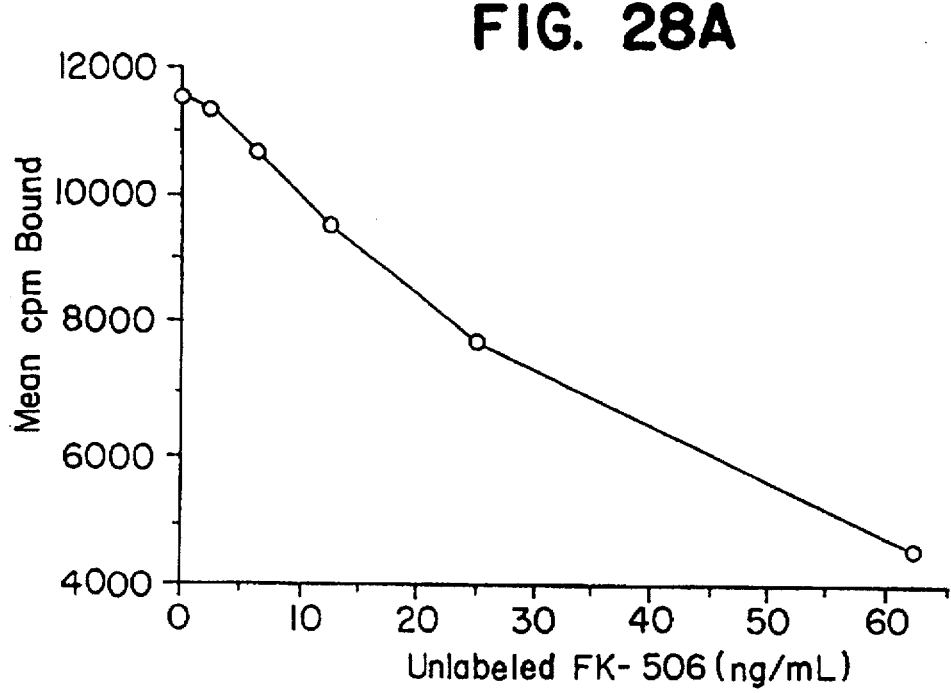
FIGS. 28(a-b) shows the protein binding assay of the invention using a purified about 10–12 kDa JURKAT lymphocyte immunophilin as the binding agent applied to FK506 in water (A) or in whole blood (B).

Binding of $^3$H-FK-506 to the purified 8–12 kDa JURKAT cell binding protein from Example 13 was performed as in Example 21, wherein protein-bound FK-506 was separated by the LH-20 method [cf., separation Method E of the specification]. The Binding Buffer consisted of 20 mM Tris buffer, pH 7.2, containing 5 mM 2-mercapto-ethanol, 0.05% $NaN_3$ and 7.5% FCS. Binding protein solutions (100 µL of 15 µg/mL protein) were mixed with 50 µL of $^3$H-FK-506 (about 2 nM, 25,000 CPM) plus 0 to 70 µg/mL unlabeled FK-506 in 12×75 mm glass tubes for 20 mins. at room temperature, then placed in ice. Bound and free ligand were separated by loading 100 µL of the cold reaction mixture onto a 7.0 cm×0.8 cm column of LH-20 equilibrated in Binding Buffer. The first 2 mL of eluate, containing protein-bound ligand, were collected and placed in scintillation vials for counting. The CPM were corrected back to the total volume of reaction mixture and expressed as the mean of at least two replicates. The thus-obtained standard curve is shown in FIG. 28A, and is seen to be usable over the entire 0–70 ng/mL concentration range.

Assay of FK-506 in Whole Blood

Unlabeled FK-506 was added to whole human blood in the concentration range of 0.5 to 5 ng/mL. FK-506 was extracted from blood by extracting 1.0 mL aliquots of the blood with 3 mL of acetonitrile (100%) by vigorous mixing for 30 seconds; precipitated proteins were removed by centrifugation at 2000 × g. Supernatant fluids were transferred to 16×100 mm test tubes, and the solvent evaporated by a stream of air at 40° C. Residues were dissolved in 100 µL of Binding Buffer, and the competition-type PBA using the 8–12 kDa protein carried out as above.

Figure 28B:
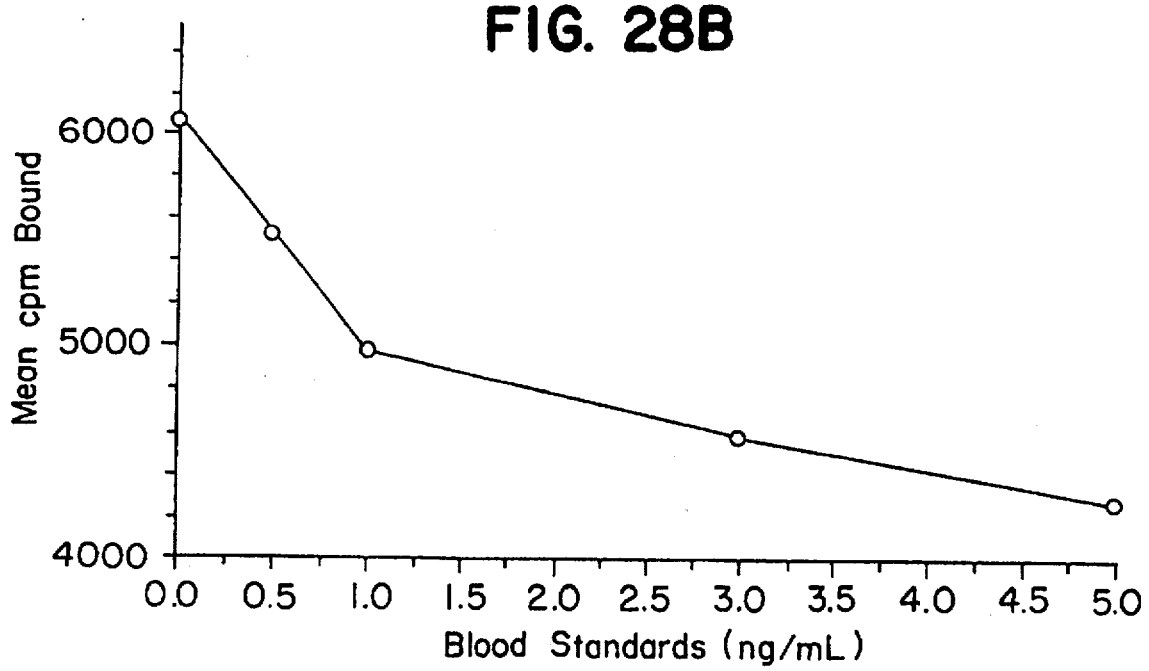

The results are shown in FIG. 28B. The assay is seen to be useful over the entire concentration range, i.e., 0 to 5.0 ng/mL FK-506 in whole blood, tested . It should be noted that this concentration range falls within the first 10% of the standard curve shown in FIG. 28A, suggesting that the useful range for assays of FK-506 in blood will extend beyond that shown by the data in FIG. 28B.

EXAMPLE 27

Assay of FK-506 in Patient Blood by Competition-Type PBA and ELISA

An FK-506 binding protein fraction was isolated from calf thymus gland by a modification of a method developed by us for JURKAT cell lines. (Palaszynski, et al., *Clin. Biochem.*, 24:63–70 (1991), which is incorporated herein by reference.) Briefly, frozen calf thymus (Pel-Freeze, Rogers, AR), stored at −70° C., was homogenized using a Polytron at medium speed and a glass homogenizer for 60 seconds, in 5 volumes of cold (4° C.) 5 mM potassium phosphate buffer, pH 6.8. The homogenate was treated with 3 mM EDTA, 1.2 mM EGTA and 20 µM PMSF to inhibit endogenous protease activity. After centrifuging the homogenate at 100,000×g for 60 minutes, the cytosol was ultrafiltered through Centriprep-30 and Centriprep-10 microconcentrators. The less-than-30 kDa and greater-than-10 kDa fraction was used as the source of the protein for the PBA.

FK-506 was extracted from patient blood as follows. One mL of water/acetonitrile (50:50) was added to 200 µl of whole blood, and hemolysis allowed to proceed over 5 minutes. After centrifugation of the hemolysate in a microfuge for 1 minute, the supernatant fluid was passed through a Bond Elut CH column (100 mg, 1 mL capacity) preconditioned by two washes with 1 mL of acetonitrile, 1 mL of $H_2O$, and 1 mL of water/acetonitrile (50%:50%). Charged columns were washed twice with distilled $H_2O$ (1 mL) and three times with 1 mL of water/acetonitrile (70:30). FK-506 was then eluted with 2×1 mL acetonitrile, and the eluate taken to dryness under $N_2$. The dried samples were used directly in the PBA of the invention. Recovery experiments using blood samples spiked with $^3$H-dihydroFK-506 showed greater than 90% recovery by this combination method. The CH sorbent column also completely removed from FK-506 contaminating prednisolone, CsA, theophylline, procaneamide, digoxin, phenobarbital, diphenylhydantoin, valproic acid or carbamazepine present in patient blood.

The competition-type PBA was conducted as follows. Whole blood standards (0–25 µg/L FK-506) and patient blood were extracted as described above. Dried residues containing FK-506 were taken up in 250 µL of Binding Buffer composed of 20 mM Tris buffer, pH 7.2–5 mM 2-mercaptoethanol-0.05% $NaN_3$ buffer containing 25 µL of $^3$H-dihydroFK-506 (5.35 nM in EtOH), 200 µL of binding protein (0.4–0.5 µg/mL) and 25 µL of fetal calf serum (FCS). FCS (10%) in the reaction mixture greatly reduced nonspecific binding of labeled FK-506 to glass surfaces, but did not interfere in the PBA. Following a 20-minute incubation at 25° C., 100 µL of a reaction mixture was added to a 1.8 mL bed volume Sephadex LH-20 column preequilibrated with 20 mM Tris buffer, pH 7.2–5 mM 2-mercaptoethanol-0.05% $NaN_3$. Elution with five 250 µL portions of this buffer completely separated free from protein-bound radioligand. The protein-bound radioactivity in the 1.25 mL of eluate was measured in 10 mL Optima Gold Scintillation Cocktail (Packard Chemicals, Meriden, Conn.) in a liquid scintillation spectrometer operating at 59% counting efficiency. NSB was estimated using a 1 µg/mL concentration of unlabeled FK-506. All analyses were performed in duplicate. For between-day precision studies, two blood samples (8 µg/L and 17 µg/L FK-506) were included with each analytical run. Linearity was evaluated with unlabeled FK-506 (0–25 µg/L) added to human blood.

Results

The % coefficient of variations in between-day precision studies at 8 µg/L and 17 µg/L FK-506 were 9.2% and 8.2% respectively.

Figure 29:
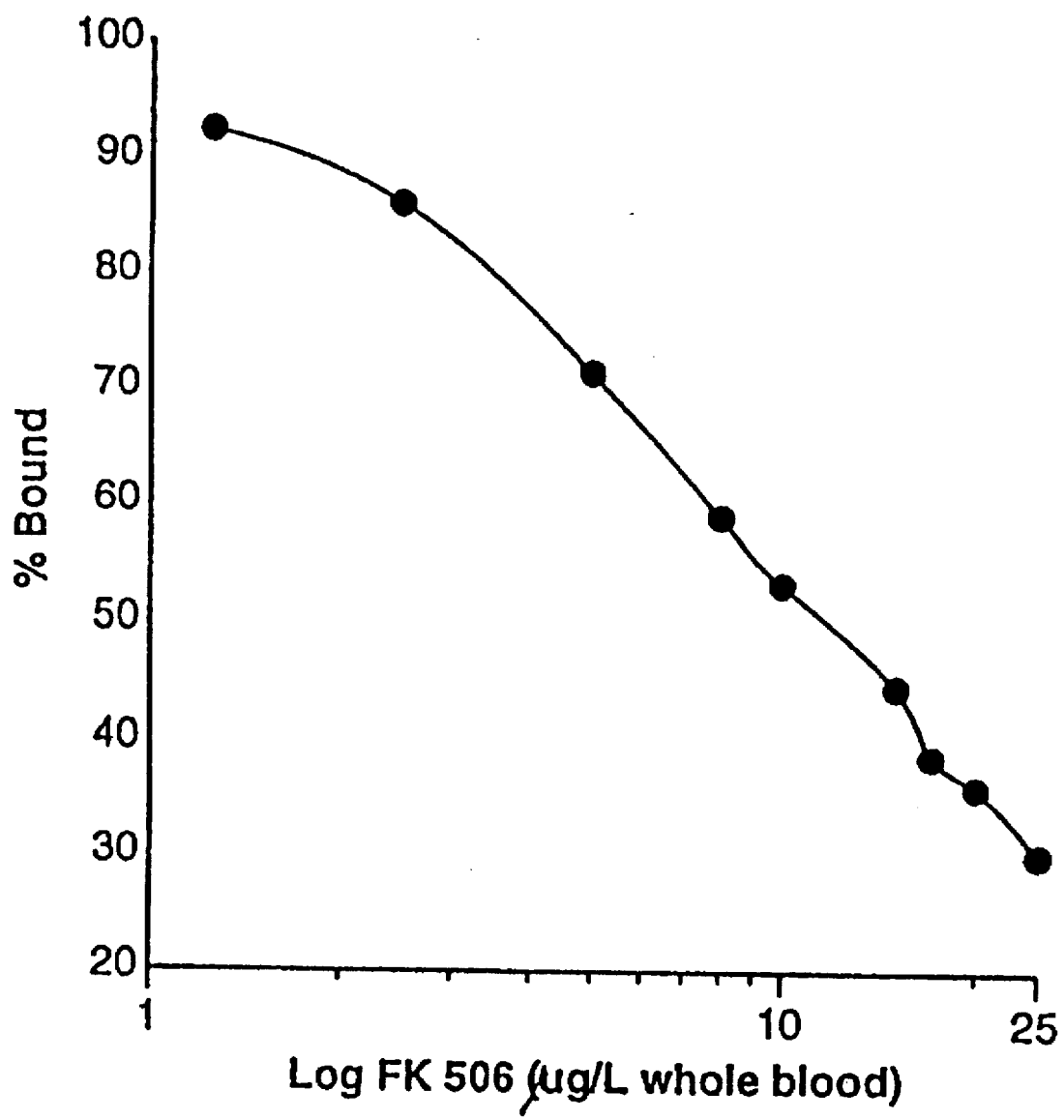
FIG. 29 shows a composite calibration curve for FK506 in whole human blood generated from 9 repetitive analyses in which FK506 was extracted from blood using the cyclohexyl sorbent column method.

FIG. 29 shows a calibration curve with FK-506 standards of 1.0, 2.5, 5.0, 8.0, 10.0, 15.0, 17.0, 20.0 and 25.0 µg/L for 9 repetitive analyses. Substantial linearity was achieved at concentrations as low as 1 µg/L FK-506.

Repetitive assays of an FK-506 sample stored in frozen (−20° C.) blood showed no variability in the assay results for at least 30 days.

Patient blood samples containing therapeutic concentrations of a variety of drugs were tested for interference in the aforedescribed assay. No drug tested (prednisolone, CsA, theophylline, procaneamide, digoxin, phenobarbital, diphenylhydantoin, valproic acid and carbamazepine) produced an ostensible FK-506 concentration of greater than 1 µg/L.

Figure 30:
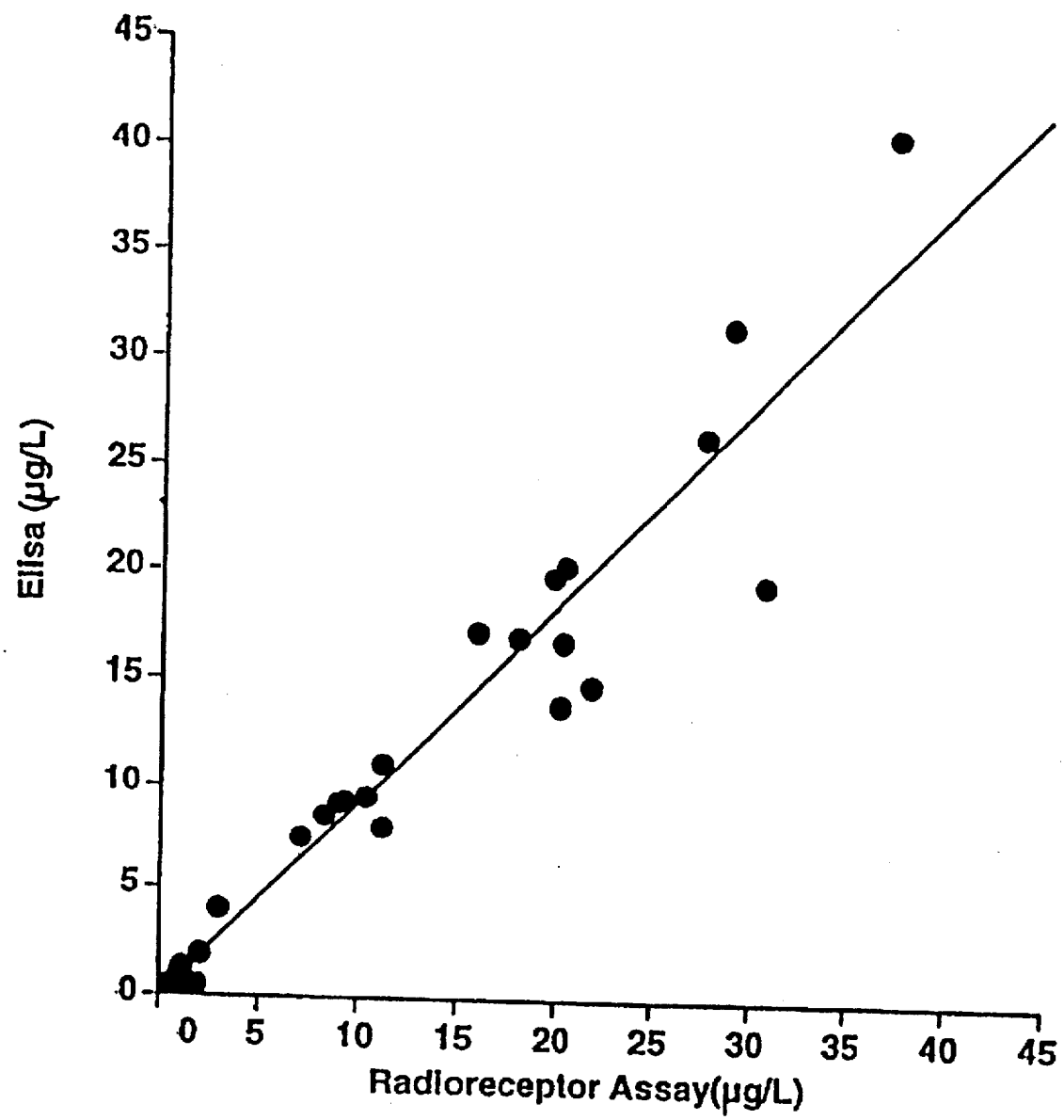
FIG. 30 shows a comparison of assays for FK506 in human patient blood by an ELISA method and by a binding assay of the invention applied to extracts of blood prepared by the cyclohexyl sorbent column method.

FIG. 30 shows a comparison of results obtained with a competition-type PBA of the invention and an ELISA procedure (Warty, Transplantation Proc., 23:2732 (1991)). The present assay can be carried out in several hours, whereas the ELISA assay requires over 24 hours. A regression coefficient of y=0.925X−0.764 and a correlation coefficient of 0.97 was obtained with concentrations of FK-506 up to about 40 µg/L. Assays are most precise at FK-506 concentrations of between 1 and about 30 µg/L.

This embodiment of the assay method of the invention is more sensitive, less time consuming and requires a smaller sample size than previously-described HPLC procedures (Christians, 1991, above; Warty 1991, above. Use of hydrophobic minisorbent columns eliminated the interferences found when studies were performed directly on whole blood (200 µl) extracted with methanol (2 mL). This embodiment is also far less time consuming, simpler to perform (fewer analytic steps), and gives more clinically significant results, than standard ELISA procedures (Tamura et al., 1987 above; Jusko, W. et al., First Internt'l FK-506 Congress, Pittsburgh, 1991, Abs. p. 7).

EXAMPLE 28

Purification of a 34–37 kDa Immunophilin from Jurkat Cells

Source: Jurkat cells were grown in bulk in RPMI 1640 with L-glutamine, 50 U/mL penicillin, 50 µg/mL streptomycin (Bio-Whittaker, Walkersville, Md., U.S.A.) and 10% fetal bovine serum (GIBCO-BRL, Gaithersburg, Md., U.S.A.). Cells were harvested weekly and the pellets stored at −20° C. A 50 mL volume of cell pellet was used. To disrupt the cell wall, the cells were subjected to three freeze-thaw cycles. The disrupted cells were suspended in 4 volumes of ice-cold 5 mM potassium phosphate buffer, pH 6.8, containing 3 mM ethylenediaminetetraacidic acid (EDTA), 1.2 mM ethyleneglycol-bis (B-aminoethyl ether) N,N,N'N'-tetraacidic acid (EGTA), 0.1 % Triton X100 and 0.5% β-mercaptoethanol (Sigma Chemical Co., St. Louis, Mo., U.S.A.). Two or three mL of the cell suspension were sonicated for 2–3 minutes using a high intensity ultrasonic processor (Sonics & Materials, Danbury, Conn., U.S.A.), a 2 mm microtip and a 50 watt setting. The homogenate was treated with the protease inhibitors pepstatin (0.05 mg/L, Boehringer Mannheim, Indianapolis, Ind., U.S.A.) and phenylmethylsulfonyl fluoride (PMSF, 0.02 mM, Sigma) and centrifuged in an ultracentrifuge at 100,000×g for 60 min (Beckman Instruments, Palo Alto, Calif., U.S.A.) to obtain a cytosol fraction which was then subjected to preparative isoelectric focussing.

Isoelectric focusing: Preparative free solution isoelectric focusing was performed using a rotofor cell (Bio-Rad Laboratories, Hercules, Calif., U.S.A.). Fifty mL of cytosol was mixed with 2.0 mL of 40% ampholytes (pH range 5–7). The mixture was loaded onto the rotofor cell and focused for 5–6 h at a constant 12 W. The initial voltage was 200–250 V and the final voltage at the end of the run was 500–550 V. After focussing, the pH and protein concentrations were measured in 20 fractions. Samples between pH 6.5 and 7.8 were pooled and refractionated for 6h to improve the separation from the major immunophilins, cyclophilin (pI 9.3) and FKBP12 (pI 8.9) (6). Fractions from pH 6.5 to 7.5 were pooled. Since ampholytes interfere in later chromatographic steps, they were first dissociated from the protein fraction by the addition of NaCl (final concentration, 1M) and incubated for 1 h at 4° C. The stripped ampholytes were removed by overnight dialysis against 5 mM phosphate buffer, pH 6.8, using dialysis tubing with an exclusion of 12 kDa (Sigma). The rotofor fraction was subjected to a simple molecular weight fractionation using Filtron Macrosep concentrators (Filtron, Northborough, Mass., U.S.A.) to obtain the greater than 30 kDa protein fraction. This fraction was diluted to four times the original volume and again passed through the 30 kDa filters. This step eliminates contamination from other major and minor immunophilins.

Ion Exchange Chromatography: Gradient cation exchange chromatography was performed using the System Gold 126 programmable HPLC (Beckman Instruments). The greater than 30 kDa fraction (10 mL, pH 7.0) was injected onto an Alltech Macrosphere weak cation exchange column (WCX7, 5 μ, 0.46×25 cm, injection volume 0.5 mL, Alltech, Deerfield, Ill., U.S.A.) which was equilibrated with 5 mM phosphate buffer, pH 6.8, at a flow rate of 0.5 mL/min. Three to five 0.5 mL injections were made before eluting the 37 kDa immunophilin. For elution, a gradient of phosphate buffer ranging from 5–1000 mM over a period of 60 minutes was used. The elution of the 37 kDa immunophilin occurred between 180–220 mM phosphate concentration. The effluent was monitored for absorbance at 280 nm and the eluted peak was collected, pooled and concentrated using Filtron 3 kDa cut off concentrators. The eluted CM peak was checked for purity and homogeneity by SDS-PAGE electrophoresis and visualized by silver staining. Protein estimations were done using a Bio-Rad protein assay kit. The ability to displace tritiated dihydro FK506 by cold FK506 ligand was measured at various stages of purification. Protein Sequence: The protein sequence analysis was performed at the W. M. Keck Foundation Biotechnology Resource Laboratory, New Haven, Conn., U.S.A. The protein was digested and subjected to amino acid analysis and matrix assisted laser desorption/ionization mass spectrometry (MALDI-MS) and internal peptide sequencing. The MALDI-MS is useful for identifying peak purity and reagent peaks derived from coomassie blue.

Properties: Scatchard analysis was performed on the isolated protein fraction using tritiated dihydro FK506. Receptor density ($B_{max}$), affinity ($K_d$) and Hill coefficients ($n_H$) were obtained using EBDA and Ligand computer programs. Radioreceptor assay: The radioreceptor assay was done in a final volume of 250 μl. To 25 μL of [$^3$H]dihydro FK506 tracer in methanol (specific activity, 51 Ci/mmol, 150–200,000 DPM), 25 μL of the cold ligand in 50% ethanol was added. To assess total binding, 25 μL of 50 % ethanol alone was added to maintain a constant level of ethanol in the reaction. 100–150 μL of 5 mM phosphate buffer, pH 6.8, containing 0.2% Tween 20, was added. 2–5 μg protein solution in 50–100 μL was added to obtain a final reaction volume of 250 μL. Following a 20 minute incubation at 25° C. on a shaker, 200 μL of the reaction mixture was added to Sephadex LH-20 columns (Pharmacia Biotech, Piscataway, N.J., U.S.A.,1.8 mL bed volume) equilibrated with LH-20 assay buffer (20 mM Tris buffer, pH 7.2, 5 mM β-mercaptoethanol and 0.05% sodium azide). Elution with 1250 μL of LH-20 assay buffer separated bound [$^3$H]dihydro FK506 from free. The bound radioactivity in the 1.25 ml eluate was measured in 10 mL of Optima™ Gold Scintillation cocktail (Packard Chemicals, Meriden, Conn., U.S.A.) with a counting efficiency of 59%. Non-specific binding was estimated using a 1 μM concentration of unlabelled FK506 which displaced>95% of the bound radioligand from the binding sites.

Results

SDS-PAGE electrophoresis: The protein from the gel filtration fraction was analyzed for purity using 10% SDS-PAGE electrophoresis in the presence and absence of mercaptoethanol and visualized using DAIICHI-II silver staining. The SDS-PAGE electrophoresis showed a single band which corresponded to a molecular weight of about 34–37 kDa (FIG. 31). Saturation experiments: Scatchard plots were obtained by performing saturation experiments using 10 concentrations of tritiated dihydro FK506 (0.25 to 20 nM). The data were analyzed using EBDA and Ligand computer programs. The data revealed linear binding with Hill coefficients near unity suggesting a single population of binding sites. Analysis gave a $K_d$ value of 4.5 nM with a $B_{max}$ of 117 nmoles/mg protein (FIG. 32). The saturation isotherm is shown in FIG. 33. Protein sequence: The protein internal sequence data are shown in Table 10.

TABLE 10

Amino acid sequences from 34–37 kDa immunophilin

| | | | | Amino acids | | | | | | |
|---|---|---|---|---|---|---|---|---|---|---|
| | 1 | 2 | 3 | 4 | 5 | 6 | 7 | 8 | 9 | 10 |
| | | | | | Internal sequence | | | | | |
| (a) | Leu | Leu | Ala | Ala | Val | Tyr | | | | |
| (b) | Val | Val | Asp | Leu | Met | Ala | Lys | | | |
| (c) | Ala | Gly | Ala | His | Leu | Gln | Gly | Gly | Ala | Lys |

The protein sequence analysis yielded three peptides from two HPLC peaks. One of the peaks contained a mixture of two peptides at a 6.5:1 ratio.

The amino acid composition of the 34–37 kDa immunophilin is shown in Table 11.

TABLE 11

Amino acid composition

| AMINO ACID | MOLE % |
|---|---|
| ASX | 14.09 |
| THR | 7.01 |
| SER | 9.07 |
| GLX | 10.64 |
| ALA | 11.46 |
| VAL | 7.87 |
| MET | 2.13 |
| ILE | 5.75 |
| LEU | 7.22 |
| TYR | 2.64 |
| PHE | 5.18 |
| HIS | 3.72 |
| LYS | 9.46 |
| ARG | 3.78 |

In addition, the pI of the 34–37 kDa immunophilin was about 6.5.

EXAMPLE 29

Abbreviated Direct Assay For Sirolimus (Rapamycin) By A Radioreceptor Assay

RAP blood standards (0–40 Mg/L) were prepared in whole blood for use in calibration curves. RAP was resuspended from the dried tubes with 25 μL methanol containing a tracer amount of labeled [$^3$H]-dihydro FK-506 (160,000 dpm). Five mM potassium phosphate buffer, pH 6.8, withy 0.25% Tween-20 (Sigma Chem. Co.) was added, followed by 20–100 μL of an immunophilin solution (5–25 μg protein of a semi-pure preparation) to yield a final volume of 250 μL. Following a 20-minute incubation period with shaking, 200 μL was put through a bed volume 1.8 mL Sephadex LH-20 column (Pharmacia Biotech, Piscataway, N.J.) equilibrated with LH-20 buffer (20 mmol/L Tris buffer, pH 7.2, 5 mmol/L β-mercaptoethanol, 0.5 g/L sodium azide preservative). Elution with 150 μL followed by 1.25 mL of LH-20 buffer separated free from bound labeled FK-506. The bound fraction was added to 10 mL of scintillation cocktail (Packard Instruments, Meriden, Conn.) and the radioactivity determined in a liquid scintillation spectromotor. Nonspecific binding was estimated using a 1 mg/L concentration of unlabeled RAP.

Comparison of the present RRA with an HPLC method produced a correlation coefficient of 0.977. Equivalent results were obtained on 5 patient samples ranging from 5–50 μg/L. Recoveries were 93% at 7.5 μg/L and 103% at 12.5 μg/L. CV's for between-run precision for 2.5, 7.5, 12.5 and 20 μg/L were 12.9, 9.2, 8.5 and 5.9%, respectively.

The HPLC method, because of its complexity, is limited to a maximum of 30 patients in a 48-hour period, whereas the present RRA permits one technician to analyze 30–50 patients during an 8-hour shift.

The partially purified immunophilin preparations are stable at refrigerator temperatures for several weeks.

What is claimed is:

1. An isolated purified cytosolic immunosuppressive drug binding protein ("immunophilin") of 34–37 kDa, said immunophilin being isolated by a process comprising the steps of:
   a. centrifuging a homogenized, disrupted normal or transformed mammalian lymphoid tissue so as to produce a water-soluble cytosolic fraction containing said immunophilin; and,
   b. fractionating said cytosolic fraction so as to produce said purified immunophilin, said isolated purified immunophilin exhibiting the properties of: specific binding to cyclosporine, FK506 or rapamycin; a molecular mass of 34–37 kDa by chromatography, SDS-PAGE or amino acid analyses; a pI of about 6.5–7.0 by isoelectric focusing; and homogeneity by SDS-PAGE.

2. A purified immunophilin according to claim 1 wherein said protein is derived from human or animal lymphoid tissue or cells.

3. A purified immunophilin according to claim 1 immobilized on a solid support.

4. A substantially pure immunophilin that specifically binds FK-506, rapamycin and cyclosporine A, and has a molecular mass of about 34–37 kDa by chromatography, SDS-PAGE or amino acid analysis and a pI of about 6.5–7.0.

5. An immunophilin according to claim 4 derived from human or animal lymphoid tissue or cells.

6. An immunophilin according to claim 4 having an approximate amino acid composition as shown in Table 11.

7. An immunophilin according to claim 4 having an internal partial amino acid sequence selected from the group consisting of: (a) Leu Leu Ala Ala Val Tyr; (b) Val Val Asp Leu Met Ala Lys and, (c) Ala Gly Ala His Leu Gln Gly Gly Ala Lys.

8. An immunophilin according to claim 4, wherein the binding capacity ($B_{max}$) of said immunophilin for FK-506 is about 117 nmoles/mg protein, and the Kd for FK-506 is about 4.5 nM.

9. An immunophilin according to claim 4 immobilized on a solid support.

10. A recombinantly produced immunophilin of molecular mass of about 34–37 kDa that specifically binds FK-506, rapamycin and CsA.

11. A protein binding assay method for an immunosuppression drug comprising cyclosporine, rapamycin or Fk-506, or a biologically active metabolite, derivative or analogue thereof, in a fluid sample, comprising the steps of:
   a) contacting said fluid sample with an isolated 34–37 kDa immunophilin, said immunophilin having a pI of about 6.5–7.0 and specifically binding cyclosporine, rapamycin or Fk-506, so that said drug forms a complex with said immunophilin;
   b) quantifying the amount of said drug specifically bound to said immunophilin in said complex; and,
   c) relating the amount of said drug specifically bound in said complex to the concentration of said drug in said fluid sample.

12. A method according to claim 11, wherein said immunophilin is immobilized on a solid support.

13. A method according to claim 11, wherein said immunophilin is in free solution.

14. A method according to claim 11, wherein said quantifying is by a competitive protein binding assay.

15. A method according to claim 13, wherein said drug is labeled with a fluorescing substance, and said relating is by fluorescence polarization.

16. A method according to claim 11 wherein said immunophilin is immobilized and wherein said drug is isolated from said complex.

17. A method according to claim 11, wherein said fluid sample is a human tissue or body fluid or an extract of a microorganism.

18. A mercantile kit comprising, in separate compartments: (a) an amount of a purified immunophilin of molecular weight 34–37 kDa optionally in free solution, immobilized on a solid support or lyophilized; (b) optionally, an amount of unlabeled FK-506, RAP or CsA; and, (c) optionally, an amount of labeled FK-506, RAP or CsA or combinations thereof.

* * * * *